US011683980B2

(12) United States Patent
Cha et al.

(10) Patent No.: US 11,683,980 B2
(45) Date of Patent: Jun. 20, 2023

(54) CONDENSED FLUORENE DERIVATIVE COMPRISING HETEROCYCLIC RING

(71) Applicant: SFC CO., LTD., Cheongju (KR)

(72) Inventors: Soon-Wook Cha, Goyang (KR); Ju-man Song, Mokpo (KR); Yu-rim Lee, Chuncheon (KR); Sang-Woo Park, Seoul (KR); Hee-Dae Kim, Miryang (KR); Seok-Bae Park, Geumsan-gun (KR)

(73) Assignee: SFC CO., LTD., Cheongju (KR)

( * ) Notice: Subject to any disclaimer, the term of this patent is extended or adjusted under 35 U.S.C. 154(b) by 493 days.

(21) Appl. No.: 15/325,001

(22) PCT Filed: Jun. 10, 2015

(86) PCT No.: PCT/KR2015/005801
§ 371 (c)(1),
(2) Date: Jan. 9, 2017

(87) PCT Pub. No.: WO2016/017919
PCT Pub. Date: Feb. 4, 2016

(65) Prior Publication Data
US 2017/0222155 A1   Aug. 3, 2017

(30) Foreign Application Priority Data
Jul. 28, 2014   (KR) .................. 10-2014-0095792

(51) Int. Cl.
*H10K 85/60*   (2023.01)
*C09K 11/06*   (2006.01)
(Continued)

(52) U.S. Cl.
CPC .......... *H10K 85/636* (2023.02); *C07C 211/61* (2013.01); *C07D 209/96* (2013.01);
(Continued)

(58) Field of Classification Search
CPC ............ H01L 51/50; C09K 2211/1092; C09K 2211/1088; C09K 2211/1029;
(Continued)

(56) References Cited

U.S. PATENT DOCUMENTS

2012/0112174 A1*  5/2012  Lee ...................... C07D 307/93
                                                         257/40
2012/0168734 A1*  7/2012  Park ...................... C09K 11/06
                                                         257/E51.026
(Continued)

FOREIGN PATENT DOCUMENTS

CN   102046598 A   5/2011
CN   102558121 A   7/2012
(Continued)

OTHER PUBLICATIONS

Extended European Search Report, European Patent Office, dated May 18, 2018.
(Continued)

*Primary Examiner* — Sean M DeGuire
(74) *Attorney, Agent, or Firm* — STIP Law Group, LLC

(57) ABSTRACT

The present invention relates to a condensed fluorene derivative comprising a hetero ring, and, more specifically, relates to an intermediate for producing a hetero-ring compound able to exhibit the outstanding element characteristic of a long life and outstanding luminance and light-emission efficiency when used as an organic light-emitting material.

10 Claims, 1 Drawing Sheet

(51) Int. Cl.
| | | |
|---|---|---|
| C07D 307/91 | (2006.01) | |
| H10K 50/00 | (2023.01) | |
| H10K 85/40 | (2023.01) | |
| C07C 211/61 | (2006.01) | |
| C07D 209/96 | (2006.01) | |
| C07D 307/77 | (2006.01) | |
| C07D 493/10 | (2006.01) | |
| C07D 495/10 | (2006.01) | |
| C07F 7/08 | (2006.01) | |

(52) U.S. Cl.
CPC ......... *C07D 307/77* (2013.01); *C07D 307/91* (2013.01); *C07D 493/10* (2013.01); *C07D 495/10* (2013.01); *C07F 7/0812* (2013.01); *C09K 11/06* (2013.01); *H10K 50/00* (2023.02); *H10K 85/40* (2023.02); *H10K 85/633* (2023.02); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H10K 85/624* (2023.02); *H10K 85/626* (2023.02); *H10K 85/657* (2023.02); *H10K 85/6572* (2023.02); *H10K 85/6574* (2023.02)

(58) Field of Classification Search
CPC .... C09K 2211/1014; C09K 2211/1011; C07D 495/10; C07C 211/61; H10K 50/00
See application file for complete search history.

(56) References Cited

U.S. PATENT DOCUMENTS

| | | | | |
|---|---|---|---|---|
| 2014/0332787 A1* | 11/2014 | Hong | .................. | H05B 33/14 257/40 |
| 2015/0105563 A1* | 4/2015 | Ahn | .................. | C07F 7/0812 548/418 |
| 2016/0093813 A1* | 3/2016 | Stoessel | .............. | H01L 51/0072 257/40 |
| 2017/0141322 A1* | 5/2017 | Cha | .................. | H01L 51/0061 |

FOREIGN PATENT DOCUMENTS

| | | |
|---|---|---|
| CN | 106458953 A | 2/2017 |
| EP | 3098873 A1 | 11/2016 |
| EP | 3144302 A1 | 3/2017 |
| EP | 3223330 A1 | 9/2017 |
| EP | 3229284 A1 | 10/2017 |
| EP | 3240057 A1 | 11/2017 |
| JP | 2008537948 A | 10/2008 |
| JP | 2009538839 A | 11/2009 |
| JP | 2012126673 A | 7/2012 |
| JP | 2013537556 A | 10/2013 |
| JP | 20140151402 | 7/2014 |
| JP | 2017515817 A | 6/2017 |
| JP | 2017529316 A | 10/2017 |
| KR | 1020120047706 A | 5/2012 |
| KR | 10-2013-0077470 A | 7/2013 |
| KR | 10-2013-0078439 A | 7/2013 |
| KR | 1020130077470 | 7/2013 |
| KR | 1020130078439 | 7/2013 |
| KR | 1020130078439 A | 7/2013 |
| KR | 20140000611 A | 1/2014 |
| KR | 1020140000611 A | 1/2014 |
| KR | 10-1429035 B | 8/2014 |
| KR | 10-2015-0009370 A | 1/2015 |
| KR | 10-2015-0130206 A | 11/2015 |
| KR | 20150124637 A | 11/2015 |
| KR | 1020150130206 | 11/2015 |
| KR | 1020150130206 A | 11/2015 |
| KR | 20170036743 A | 4/2017 |
| WO | 2013100464 A1 | 7/2013 |
| WO | 2013100467 A1 | 7/2013 |
| WO | 2013105747 A1 | 7/2013 |
| WO | WO2013151297 A1 | 10/2013 |
| WO | 2013165189 A1 | 11/2013 |
| WO | 2014010910 A1 | 1/2014 |
| WO | 2014030831 A1 | 2/2014 |
| WO | 2014058124 A1 | 4/2014 |
| WO | 2014094963 A1 | 6/2014 |
| WO | 2014104514 A1 | 7/2014 |
| WO | WO2014111269 A2 | 7/2014 |
| WO | 2015-022051 A | 2/2015 |
| WO | 2015090504 A2 | 6/2015 |
| WO | 2015124255 A1 | 8/2015 |
| WO | 2015174682 A1 | 11/2015 |
| WO | 2016079944 A1 | 5/2016 |
| WO | 2016088759 A1 | 6/2016 |
| WO | 2016104289 A1 | 6/2016 |
| WO | WO2016140497 A2 | 9/2016 |
| WO | WO2016171429 A2 | 10/2016 |

OTHER PUBLICATIONS

Chatterjea et al. Synthesis of Furano Compounds. Part XLV Syntheses of 1-Oxo-1H-Benzo[b]Furo[4,3-d]Indeno [2'1';5,6]Pyrans and Nitrogen Analogues, Journal of the Indian Chemical Society, vol. 57; No. 12; 1980; pp. 1163-1165; Indian Chemical Society, IN; ISSN: 0019-4522.

Office Action from Chinese Patent Office, dated Feb. 26, 2018, pp. 1-14.

International Search Report of PCT/KR2015/005801, dated Aug. 24, 2016.

Office Action from Korean Intellectual Property Office of 10-2014-0095792, dated Oct. 21, 2018.

Office Action from Japan Patent Office of 2019-030653, dated Jan. 21, 2020.

J.N.Chatterjea and Radhika Pati Sahai, Syntheses of Furano Compounds. Part XLV Syntheses of 1-Oxo-1H-Benzo[b]Furo[4,3-d]Indeno [2'1': 5,6]Pyrans and Nitrogen Analogues, Journal of the Indian Chemical Society, 1980, pp. 1163-1165, vol. 57, No. 12, Indian Chemical Society, Kolkata, India.

* cited by examiner

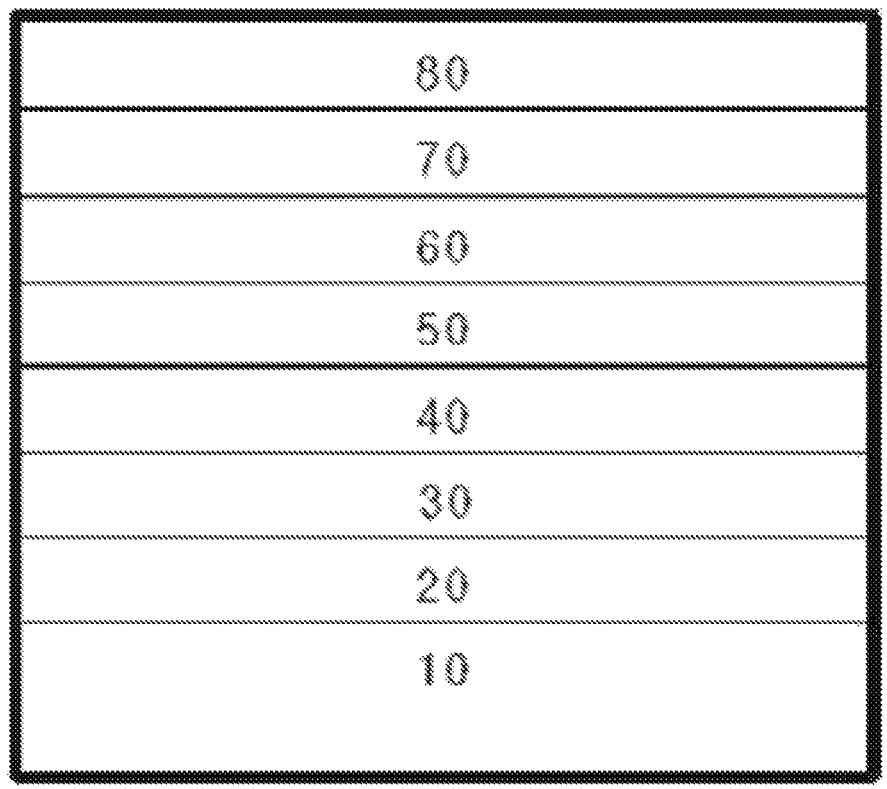

CONDENSED FLUORENE DERIVATIVE COMPRISING HETEROCYCLIC RING

CROSS-REFERENCE TO RELATED APPLICATIONS

This application is the U.S. National Phase under 35 U.S.C. § 371 of International Application No. PCT/KR2015/005801 filed on Jun. 10, 2015, which in turn claims the benefit of Korean Application No. 10-2014-0095792, filed on Jul. 28, 2014, the disclosures of which are incorporated by reference into the present application.

TECHNICAL FIELD

The present disclosure relates to a condensed fluorene derivative containing a heterocyclic ring. More particularly, the present disclosure relates to an intermediate of a heterocyclic compound that is superior in luminance and light emission efficiency when used as an organic luminescent material and that secures a long lifetime and excellent properties for organic light-emitting diodes.

BACKGROUND ART

Organic light-emitting diodes (OLEDs), based on self-luminescence, are used to create digital displays having the advantage of being able to be made thinner and lighter than liquid crystal displays (LCDs). In addition, an OLED display exhibits a much faster response time than an LCD. Accordingly, organic light-emitting diodes find applications in the illumination field as well as the full-color display field.

In general, the term "organic light-emitting phenomenon" refers to a phenomenon in which electrical energy is converted to light energy by means of an organic material. An organic light-emitting device using the organic light-emitting phenomenon has a structure usually comprising an anode, a cathode, and an organic material layer interposed therebetween. In this regard, the organic material layer may be of a multilayer structure consisting of different materials, for example, a hole injection layer, a hole transport layer, a light-emitting layer, an electron transport layer, and an electron injection layer, in order to improve the efficiency and stability of the organic light-emitting diode. In the organic light-emitting device having such a structure, when a voltage is applied between the two electrodes, a hole injected from the anode migrates to the organic layer while an electron is released from the cathode and moves toward the organic layer. In the luminescent, zone, the hole and the electron recombine to produce an exciton. When the exciton returns to the ground state from the excited state, the molecule of the organic layer emits light. Such an organic light-emitting diode is known to have characteristics such as self-luminescence, high luminance, high efficiency, low driving voltage, a wide viewing angle, high contrast and high-speed response.

The materials used as organic layers in organic light-emitting diodes may be divided into luminescent materials and charge-carrying materials, for example, a hole injection material, a hole transport material, an electron injection material, and an electron transport material. As for the luminescent materials, there are two main families, of OLED: those based on small molecules and those employing polymers. The light-emitting mechanism forms the basis for classification of the luminescent materials as fluorescent or phosphorescent materials, which use excitons in singlet and triplet states, respectively. Further, luminescent materials may be divided according to color into blue, green, and red light-emitting materials. Further, yellow and reddish yellow light-emitting materials have been developed in order to achieve more natural colors.

Meanwhile, when a single material is employed as the luminescent material, intermolecular actions cause the maximum luminescence wavelength to shift toward a longer wavelength, resulting in reduced color purity and light emission efficiency. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of dopant because the wavelength of the host moves to the wavelength range of the dopant.

With regard to related arts pertaining to dopant compounds in the light-emitting layer, reference may be made to Korean Unexamined Patent Application Publication No. 10-2008-0015865 (Feb. 20, 2008), which describes an organic light-emitting device using an arylamine-coupled indenofluorene derivative, and Korean Unexamined Patent Application Publication No. 10-2012-0047706 (May 14, 2012), which describes an organic photoelectric device using a compound in which dibenzofuran or dibenzothiophene coexists with fluorene or carbazole.

In spite of enormous efforts, there is still the continued need to develop novel organic luminescent materials and intermediate compounds thereof that exhibit excellent luminance, light emission efficiency, and lifetime compared to those developed based on conventional technology.

DISCLOSURE

Technical Problem

Therefore, it is an object of the present disclosure to provide a novel intermediate of a compound available as an organic luminescent material for use in an organic light emitting diode (OLED).

Technical Solution

In order to accomplish the object, the present disclosure provides a compound represented by the following Chemical Formula A or B.

[Chemical Formula A]

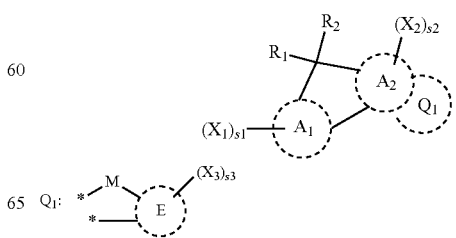

-continued

[Chemical Formula B]

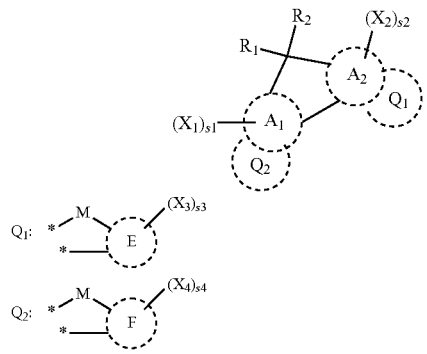

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

M is any one selected from among N—$R_3$, $CR_4R_5$, $SiR_6R_7$, $GeR_8R_9$, O, S, and Se;

$R_1$ to $R_9$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy to 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ together may form a mono- or polycyclic aliphatic or aromatic ring that may be heterocyclic ring containing at least one heteroatom selected from, among N, O, P, Si, S, Ge, Se, and Te as a ring member;

s1, s3, and s4 are each independently an integer of 0 to 3, and s2 is an integer of 1 to 3, with the proviso that, when any of s1 to s4 is 2 or greater, the corresponding $X_1$ to $X_4$ may be the same or different, $X_1$ to $X_4$ may be the same or different, and are each independently selected from among hydrogen, deuterium and a leaving group;

two adjacent carbon atoms of the $A_2$ ring moiety of Chemical Formula A may occupy respective positions * of Structural Formula $Q_1$ to form a fused ring; and two adjacent carbon atoms of the $A_1$ ring moiety of Chemical Formula B may occupy respective positions of structural Formula $Q_2$ to form a fused ring, and two adjacent carbon atoms of the $A_2$ ring moiety of Chemical Formula B may occupy respective positions * of Structural Formula $Q_1$ to form a fused ring.

Advantageous Effects

The compound represented by Chemical Formula A or B is used as an intermediate of an organic luminescent material, which exhibits excellent diode properties, including luminance, light emission efficiency and longevity, compared to conventional materials, thus being available for use in organic light-emitting diodes having improved properties.

DESCRIPTION OF DRAWING

FIG. 1 is a schematic cross-sectional view of the structure of an organic light-emitting diode fabricated according to some embodiments of the present disclosure.

BEST MODE

Below, a detailed description will be given of the present disclosure.

The present disclosure addresses an intermediate, represented by Chemical Formula A or B, which is available as an organic luminescent material for use in an organic light-emitting diode (OLED).

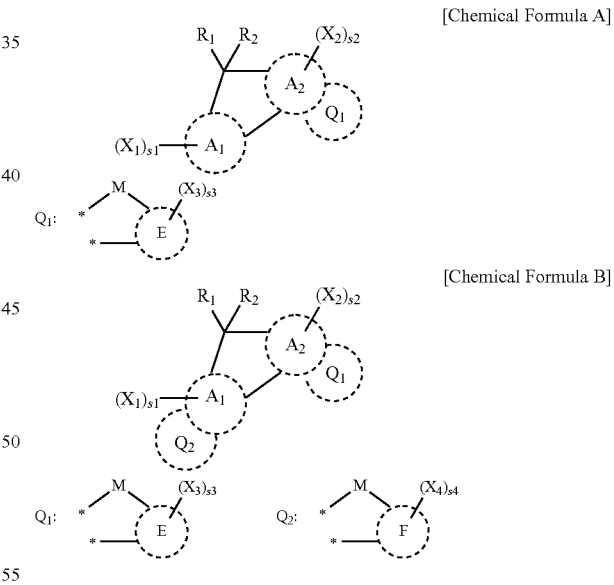

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

M is any one selected from among N—$R_3$, $CR_4R_5$, $SiR_6R_7$, $GeR_8R_9$, O, S, and Se;

$R_1$ to $R_9$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ together may form a mono- or polycyclic aliphatic or aromatic ring that may be a heterocyclic ring containing at least one heteroatom selected from, among N, O, Si, S, Ge, Se, and Te as a ring member;

s1, s3, and s4 are each independently an integer of 0 to 3, and s2 is an integer of 1 to 3, with the proviso that when any of s1 to s4 is 2 or greater, the corresponding $X_1$ to $X_4$ may be the same or different, $X_1$ to $X_4$ may be the same or different, and are each independently selected from among hydrogen, deuterium and a leaving group;

two adjacent carbon atoms of the $A_2$ ring moiety of Chemical Formula A may occupy respective positions of Structural Formula $Q_1$ to form a fused ring; and two adjacent carbon atoms of the $A_1$ ring moiety of Chemical Formula B may occupy respective positions of structural Formula $Q_2$ to form a fused ring, and two adjacent carbon atoms of the $A_2$ ring moiety of Chemical Formula B may occupy respective positions * of Structural Formula $Q_1$ to form a fused ring, wherein the term 'substituted' in the expression 'substituted or unsubstituted' means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

The compound represented by Chemical Formula A used in the present disclosure is characterized by structure in which the moiety of Chemical Formula $Q_1$ is connected to the ring $A_2$ while X2, which is hydrogen, deuterium or a leaving group, is bonded to the ring $A_2$.

In addition, the compound represented by Chemical Formula B used in the present disclosure is characterized by a structure in which the moieties of Chemical Formulas $Q_2$ and $Q_1$ are respectively connected to the rings $A_1$ and $A_2$ while X2, which is hydrogen, deuterium or a leaving group, is bonded to the ring $A_2$.

The expression for a number of carbon atoms, such as in "a substituted or unsubstituted alkyl of 1 to 30 carbon atoms", "a substituted or unsubstituted aryl of 6 to 50 carbon atoms", etc., means the total number of carbon atoms in, for example, the alkyl or aryl radical or moiety alone, exclusive of the number of carbon atoms of the substituent. For instance, a phenyl group with a butyl at the para position falls within the scope of an aryl of 6 carbon atoms, even if it is substituted with a butyl radical of 4 carbon atoms.

As used herein, the term "aryl" means an aromatic system composed of a hydrocarbon containing one or more rings. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, phenalenyl, pyrenyl, indenyl, fluorenyl, tetrahydronaphthyl, perylenyl, chrysenyl, naphthacenyl, acenaphthylenyl, indacenyl, and fluoranthenyl, at least one hydrogen atom of which may be substituted by a deuterium atom, a halogen atom, a hydroxy, a nitro, a cyano, a silyl, an amino (—$NH_2$, —NH(R), —N(R')(R'') wherein R' and R'' are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms containing one to three heteroatoms selected from among N, O, P, Si, S, Ge, Se, and Te. In the aromatic system, two or more rings may be fused. One or more hydrogen atoms on the heteroaryl may be substituted with the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. One or more hydrogen atoms of the silyl may be substituted by the same substituent as in the aryl.

According to one embodiment, $A_1$, $A_2$, E, and F in Chemical Formula A or B may be the same or different, and may each be independently a substituted or unsubstituted aromatic hydrocarbon ring of 6 to 50 carbon atoms.

When $A_1$, $A_2$, E, and F in Chemical Formula A or B are each independently a substituted or unsubstituted aromatic hydrocarbon ring of 6 to 50 carbon atoms, the aromatic hydrocarbon ring moieties may each be independently any one selected from among [Structural Formula 10] to [Structural Formula 21].

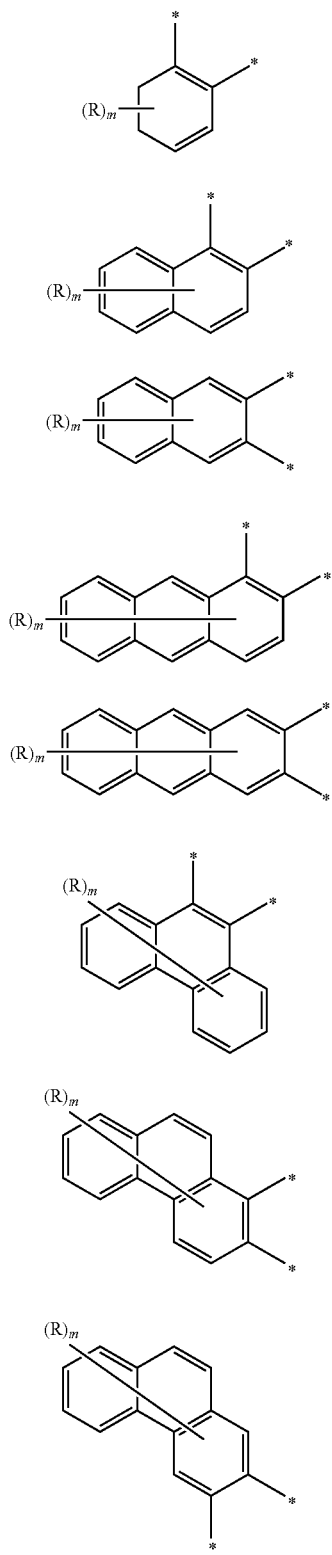

[Structural Formula 10]

[Structural Formula 11]

[Structural Formula 12]

[Structural Formula 13]

[Structural Formula 14]

[Structural Formula 15]

[Structural Formula 16]

[Structural Formula 17]

[Structural Formula 18]

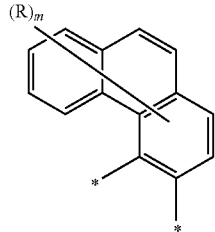

[Structural Formula 19]

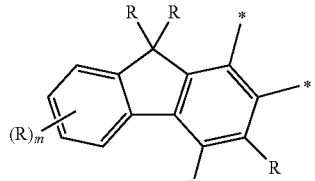

[Structural Formula 20]

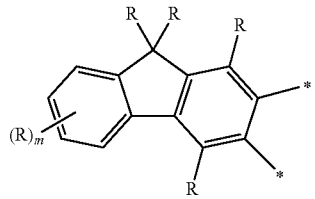

[Structural Formula 21]

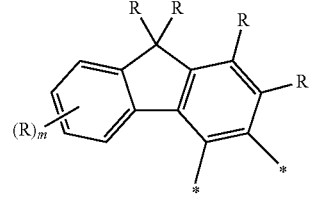

wherein,

"-*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$; and m is an integer of 1 to 8, with the proviso that, when m is 2 or greater or when two or more R's exist, the corresponding R's may be the same or different.

In the present disclosure, $X_1$ to $X_4$ may be the same or different, and are each independently hydrogen, deuterium, or leaving group.

Here, any radical may be used as the leaving group without limitation, so long as it is adapted to the design of a molecular structure applicable to an organic luminescent material by introducing a desired substituent in place thereof into the structure.

For example, the leaving group may leave upon reaction with a secondary amine, with the concomitant production of a tertiary amine. Another example may be the role of the leaving group in a Suzuki reaction, where an organoboron species (ex. containing an aryl or alkyl radical) is coupled with a halide (ex. containing an aryl radical, such as anthracene).

In some embodiments of the present disclosure, the leaving group may be selected from the group consisting of a halogen atom, an alkyl sulfonate of 1 to 30 carbon atoms, an aryl sulfonate of to 40 carbon atoms, an arylalkyl sulfonate of 7 to 40 carbon atoms, and a halogenated alkyl sulfonate of 1 to 30 carbon atoms, with preference for a halogen atom selected from among Cl, Br, F, and I.

When the leaving group is a halogen atom, s2 is 1 and s1, s3 and s4 may be the same or different, and are each independently 0 or 1. That is, one halogen atom is bound to the A2 ring moiety while no halogen atoms or one halogen atom is bound to the A1, E or F ring moiety in Chemical Formulas A and B.

In particular embodiments of the present disclosure, the substituents $R_1$ and $R_2$ of Chemical Formula A or Chemical Formula B, which may be the same or different, are each independently a substituted or unsubstituted aryl of 6 to 24 carbon atoms, and may or may not be connected to each other to form a ring.

According to a specific embodiment of the present disclosure, $R_1$ and $R_9$ may be the same or different, and are each independently any one selected from among hydrogen, deuterium, a substituted or unsubstituted aryl 6 to 20 carbon atoms, a substituted or unsubstituted cycloalkyl of 3 to 30 carbon atoms, a substituted or unsubstituted heteroaryl of 2 to 20 carbon atoms containing at least one heteroatom selected from among O, N, S, and Si, a cyano, and a halogen.

In the compound of Chemical Formula A or B according to some embodiments of the present disclosure, $A_1$, $A_2$, E, F, and $R_1$ to $R_2$ may have as a substituent any one selected from the group consisting of a cyano, a halogen, an alkyl of 1 to 6 carbon atoms, an aryl of 6 to 18 carbon atoms, an arylalkyl of 6 to 18 carbon atoms, a heteroaryl of 3 to 18 carbon atoms, an alkylsilyl of 1 to 12 carbon atoms, an arylsilyl of 6 to 18 carbon atoms, and a halogenated alkyl of 1 to 6 carbon atoms.

The compound of the present disclosure may be selected from compounds represented by the following [Chemical Formula 1] to

[Chemical Formula 108]

[Compound 1]

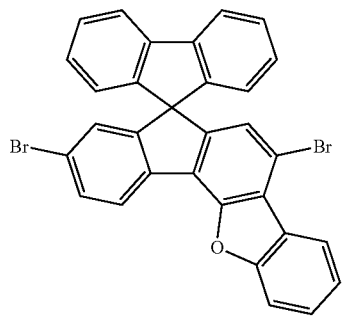

[Compound 2]

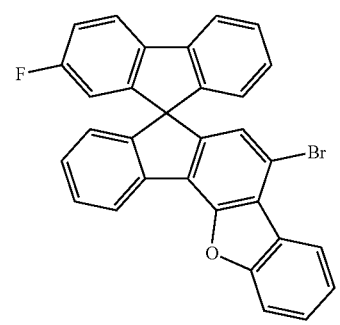

[Compound 3]

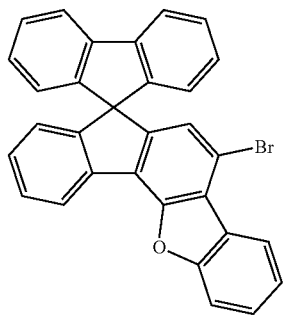

[Compound 4]

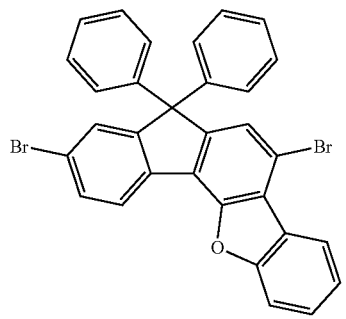

[Compound 5]

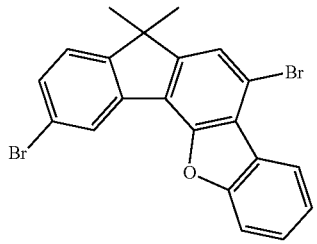

[Compound 6]

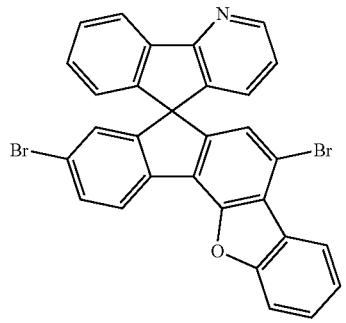

[Compound 7]

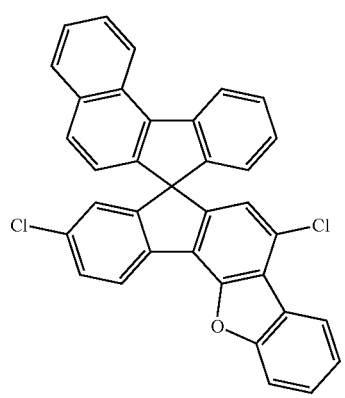

[Compound 8]
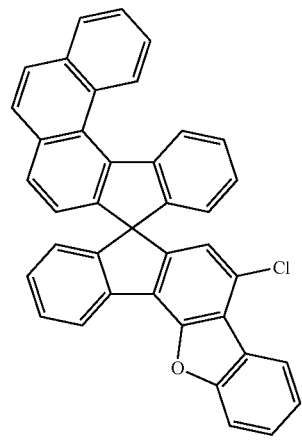
[Compound 9]
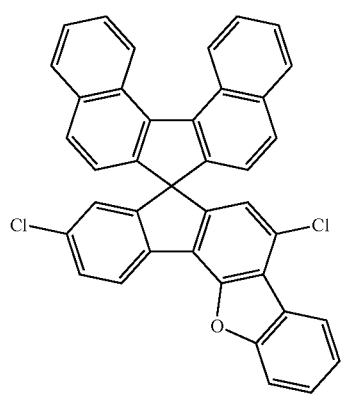
[Compound 10]
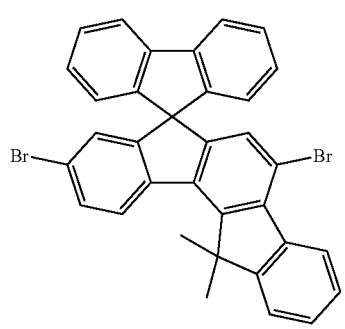
[Compound 11]
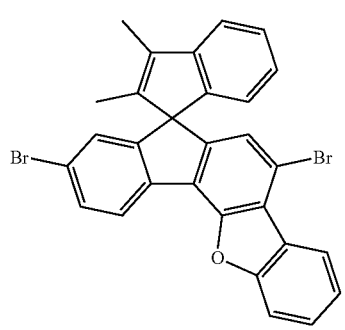
[Compound 12]
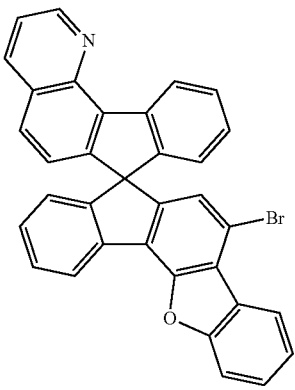
[Compound 13]
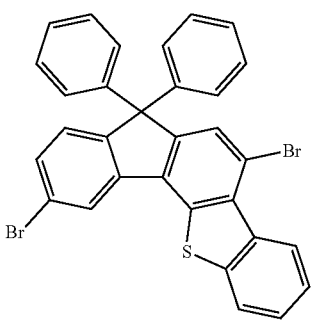
[Compound 14]
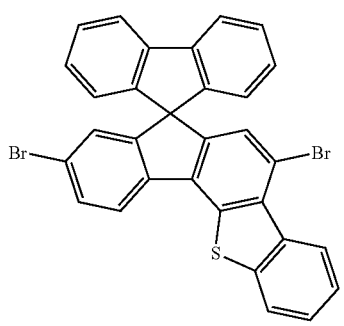
[Compound 15]
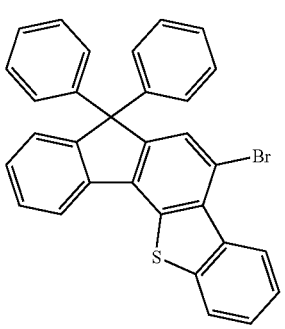

[Compound 16]
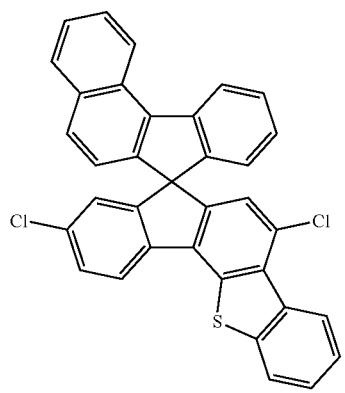
[Compound 17]
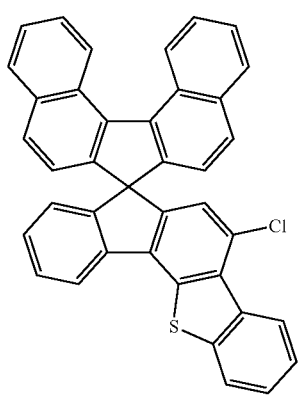
[Compound 18]
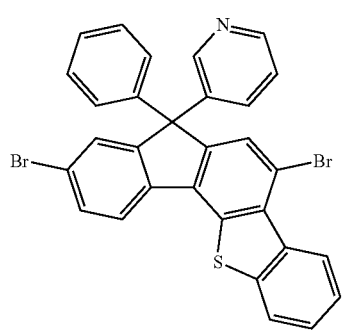
[Compound 19]
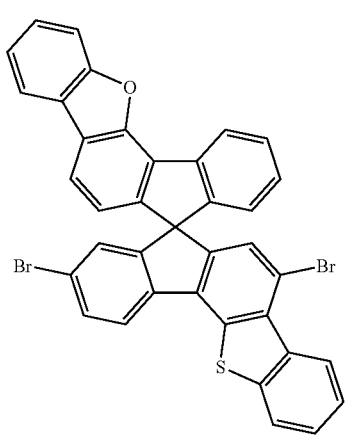
[Compound 20]
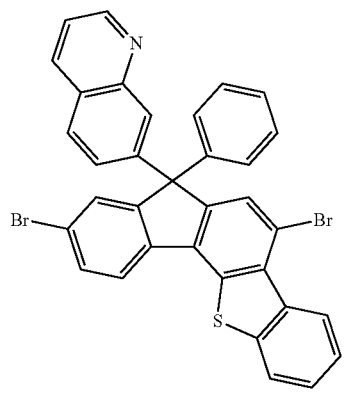
[Compound 21]
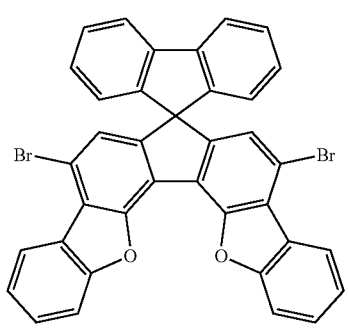
[Compound 22]
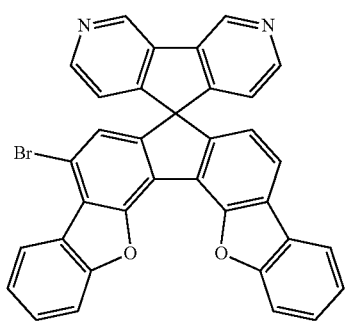
[Compound 23]
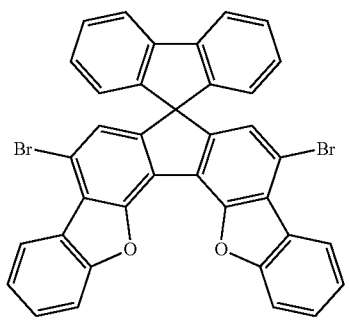

[Compound 24]
[Compound 25]
[Compound 26]
[Compound 27]
[Compound 28]
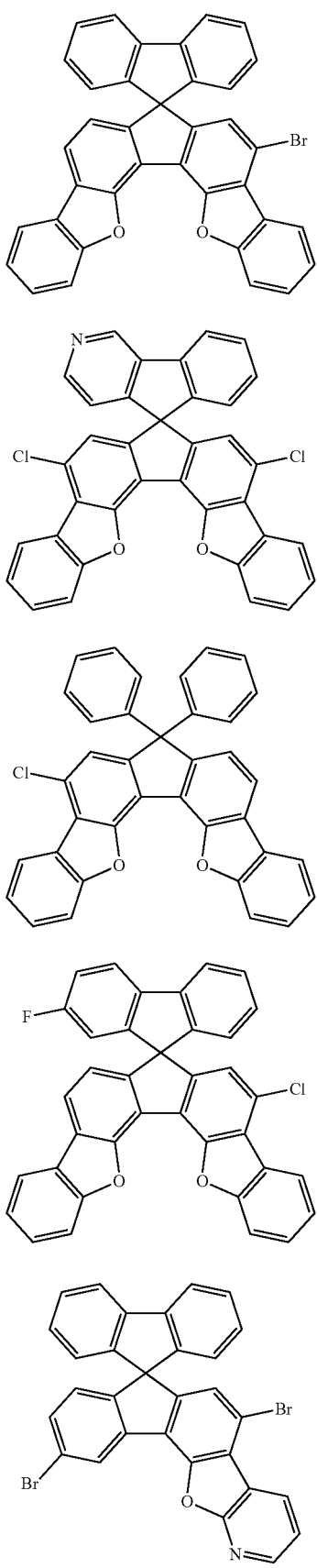
[Compound 29]
[Compound 30]
[Compound 31]
[Compound 32]
[Compound 33]
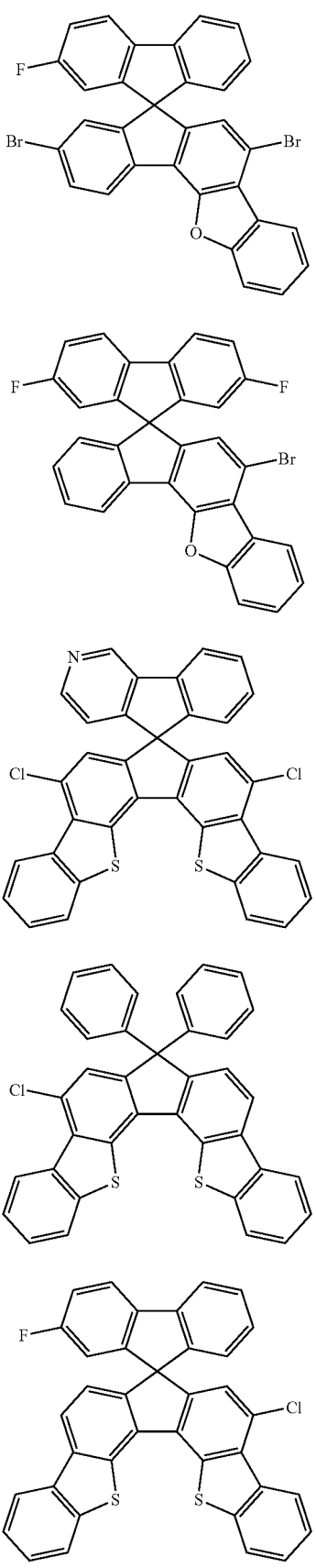

[Compound 34]
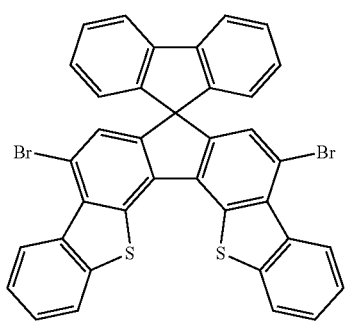
[Compound 35]
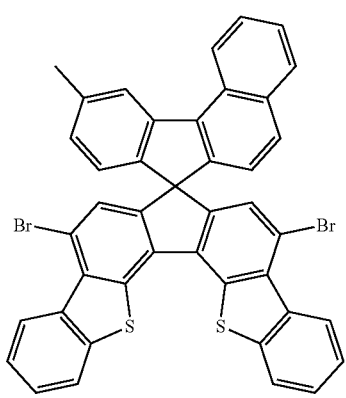
[Compound 36]
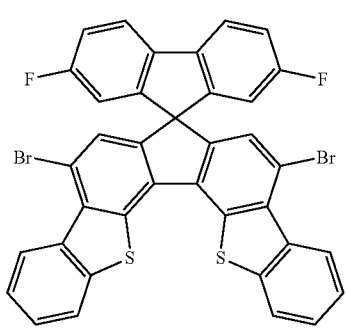
[Compound 37]
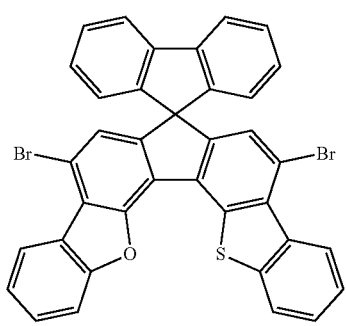
[Compound 38]
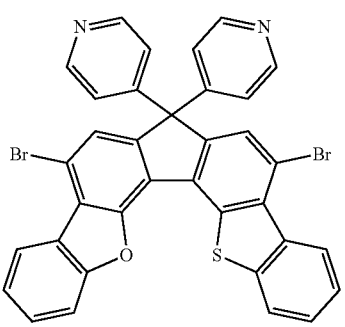
[Compound 39]
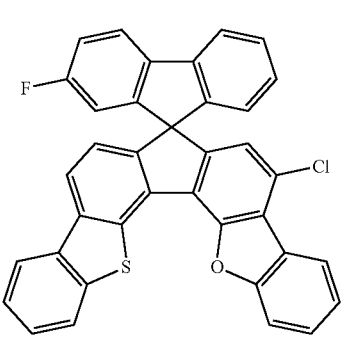
[Compound 40]
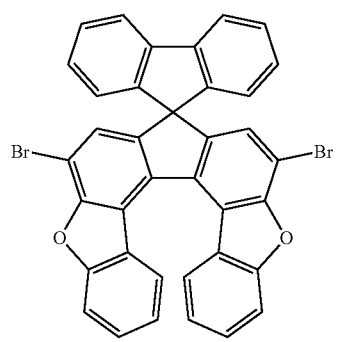
[Compound 41]
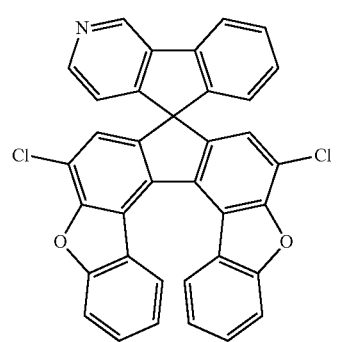

[Compound 42]
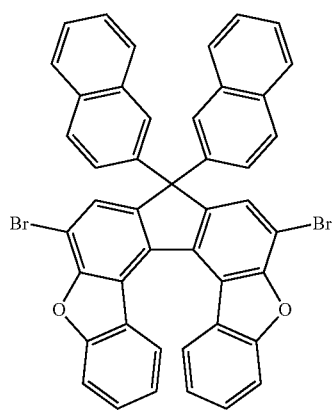
[Compound 43]
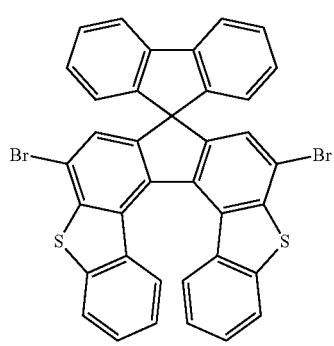
[Compound 44]
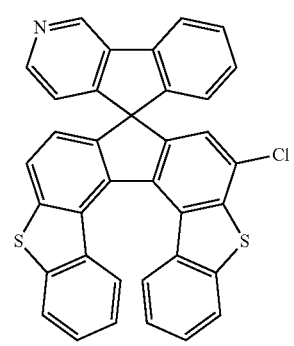
[Compound 45]
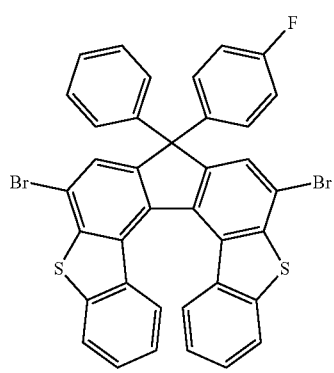
[Compound 46]
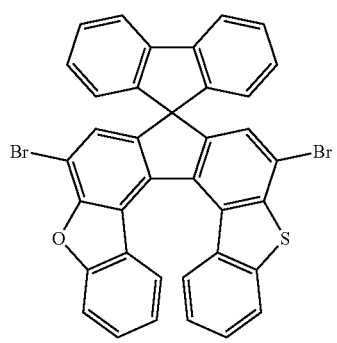
[Compound 47]
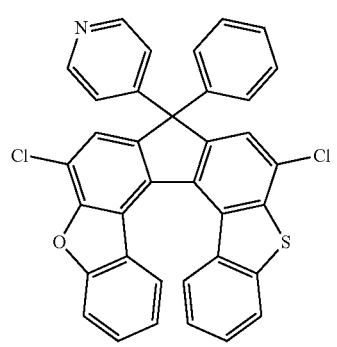
[Compound 48]
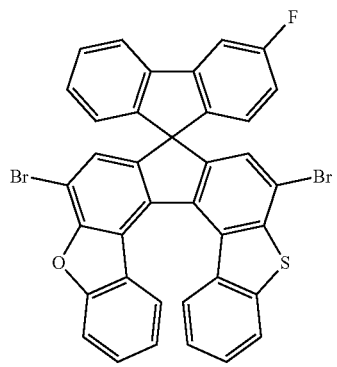
[Compound 49]
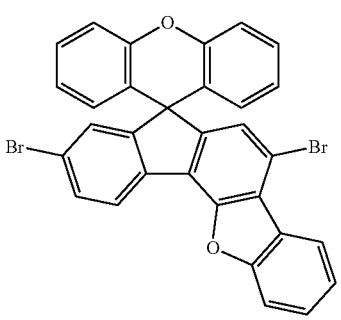

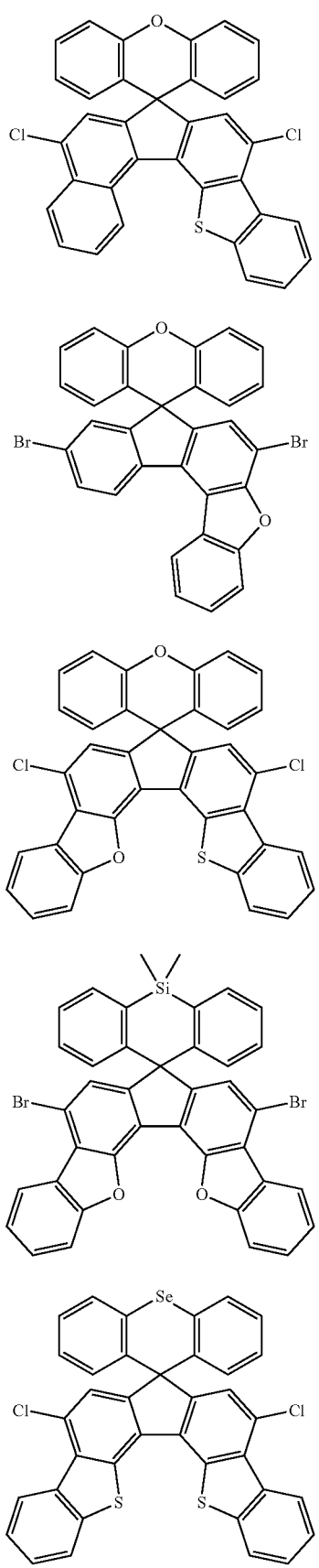
[Compound 50]
[Compound 51]
[Compound 52]
[Compound 53]
[Compound 54]
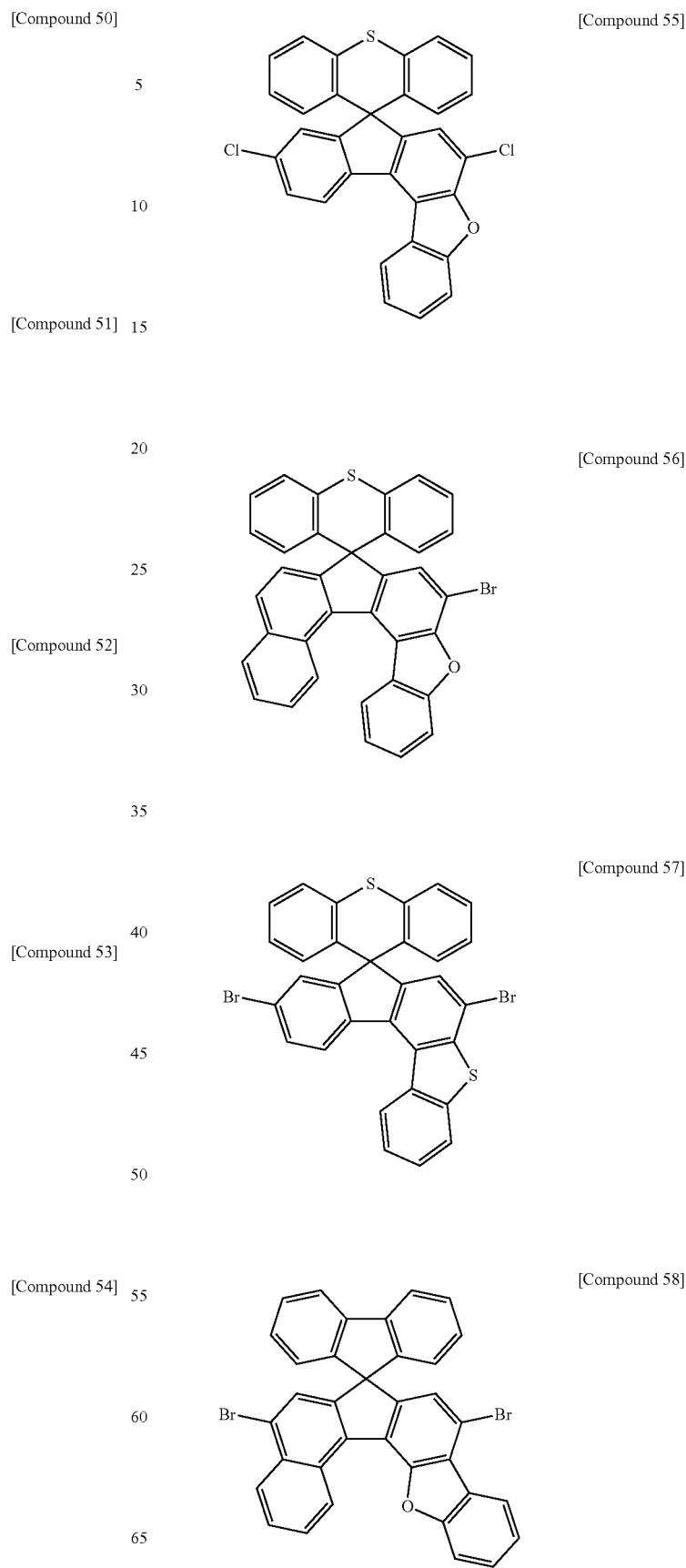
[Compound 55]
[Compound 56]
[Compound 57]
[Compound 58]

[Compound 59]
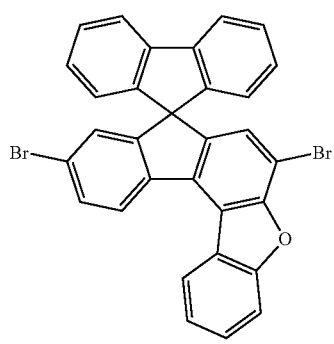
[Compound 60]
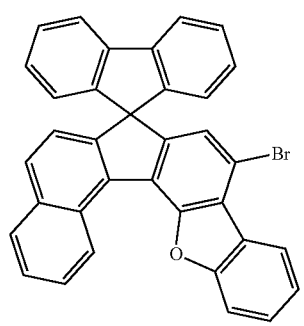
[Compound 61]
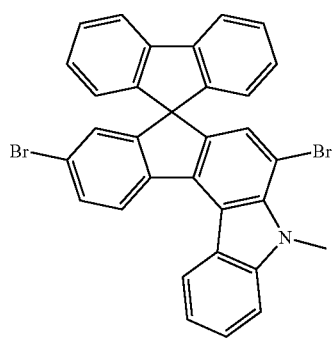
[Compound 62]
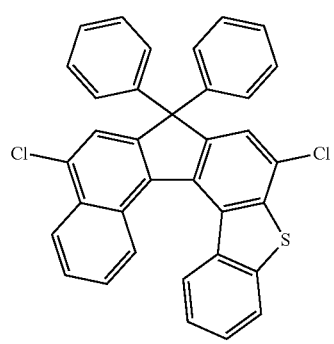
[Compound 63]
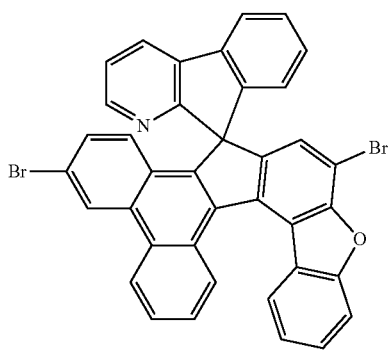
[Compound 64]
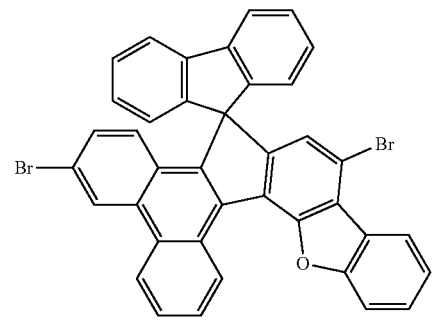
[Compound 65]
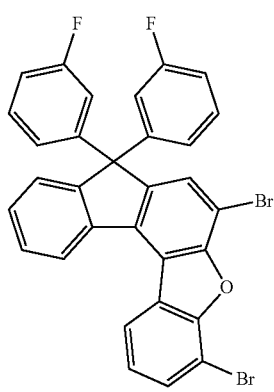
[Compound 66]
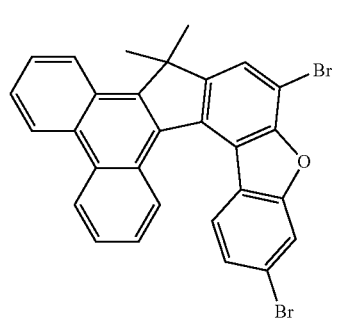

[Compound 67]
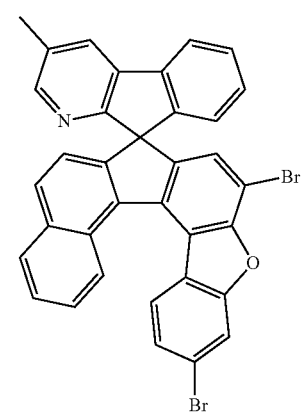
[Compound 68]
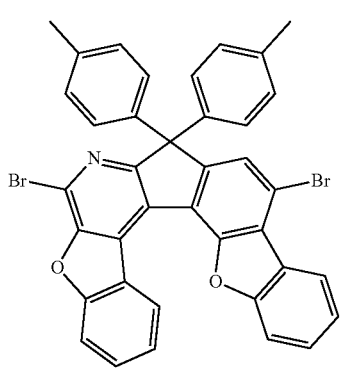
[Compound 69]
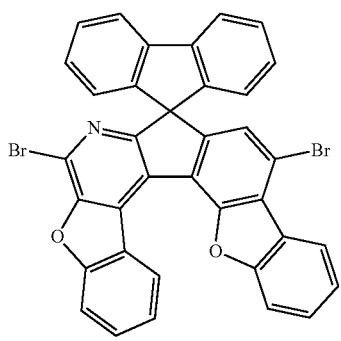
[Compound 70]
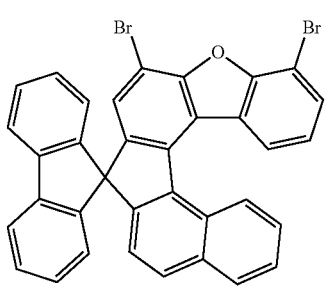
[Compound 71]
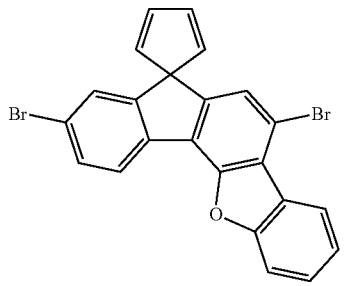
[Compound 72]
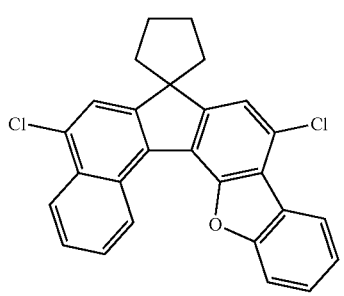
[Compound 73]
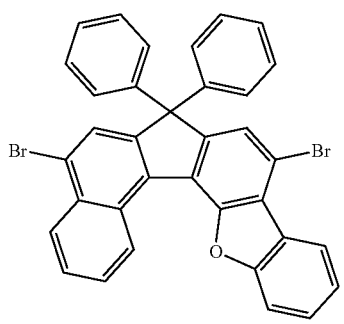
[Compound 74]
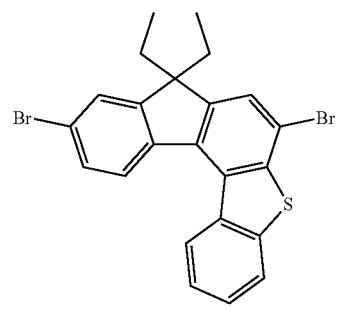
[Compound 75]
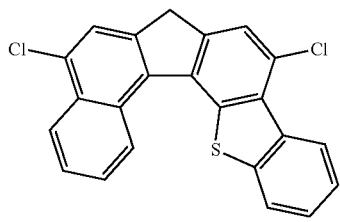

[Compound 76]
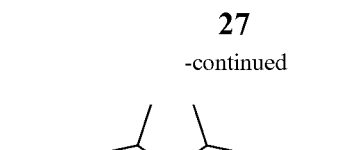
[Compound 77]
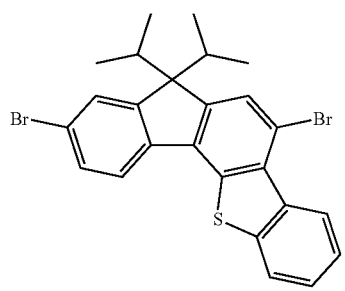
[Compound 78]
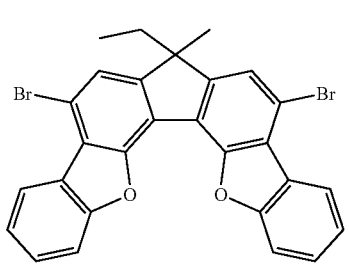
[Compound 79]
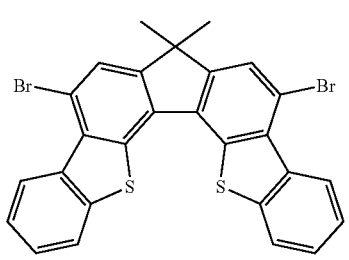
[Compound 80]
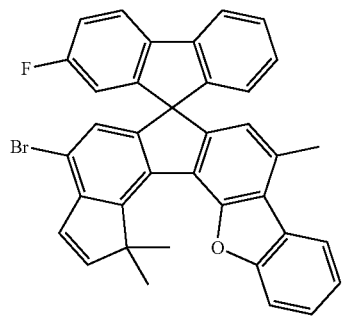
[Compound 81]
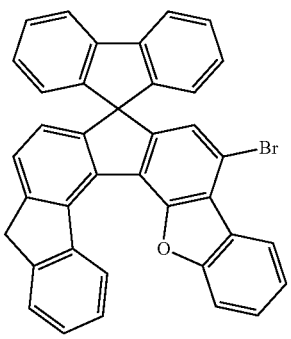
[Compound 82]
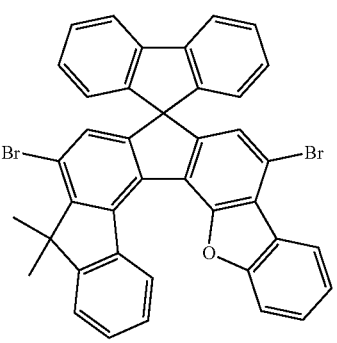
[Compound 83]
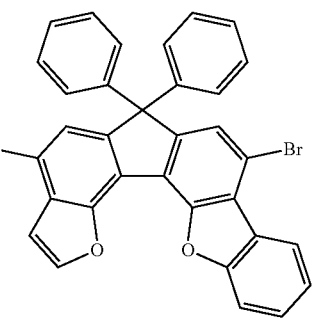
[Compound 84]
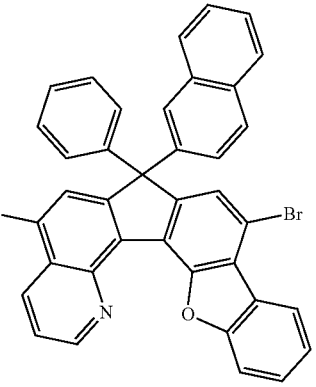

[Compound 85]
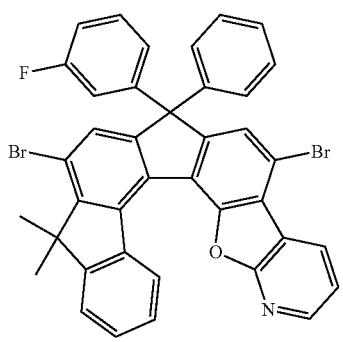
[Compound 90]
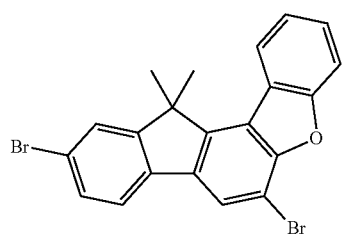
[Compound 86]
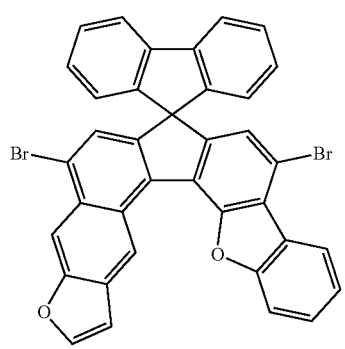
[Compound 91]
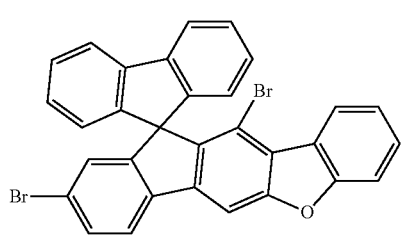
[Compound 87]
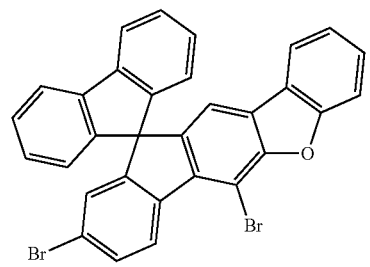
[Compound 92]
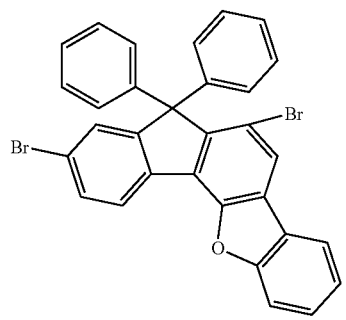
[Compound 88]
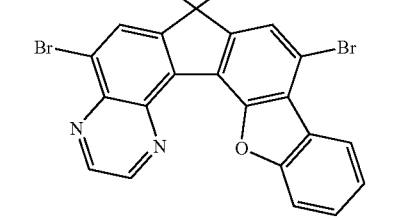
[Compound 93]
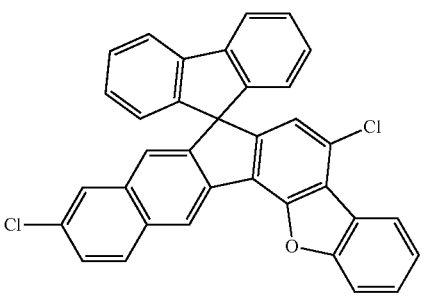
[Compound 89]
[Compound 94]

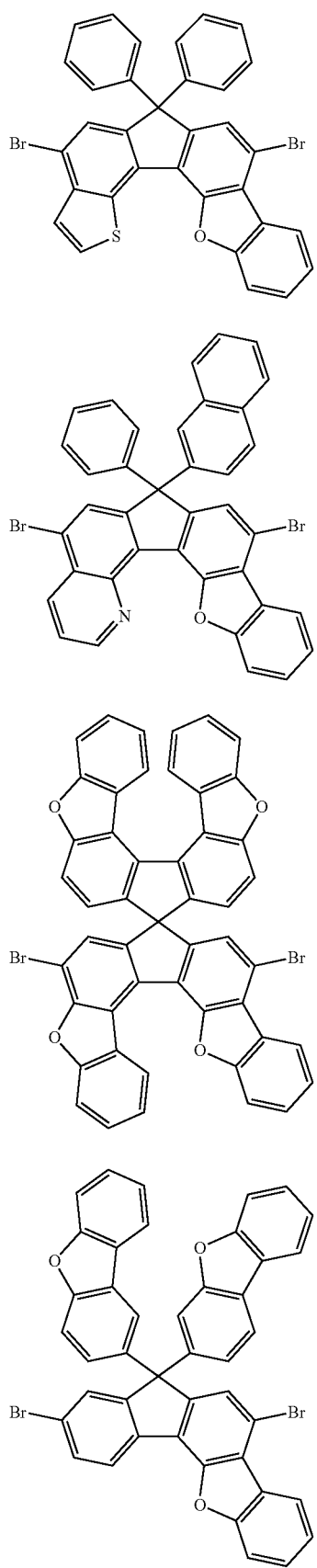
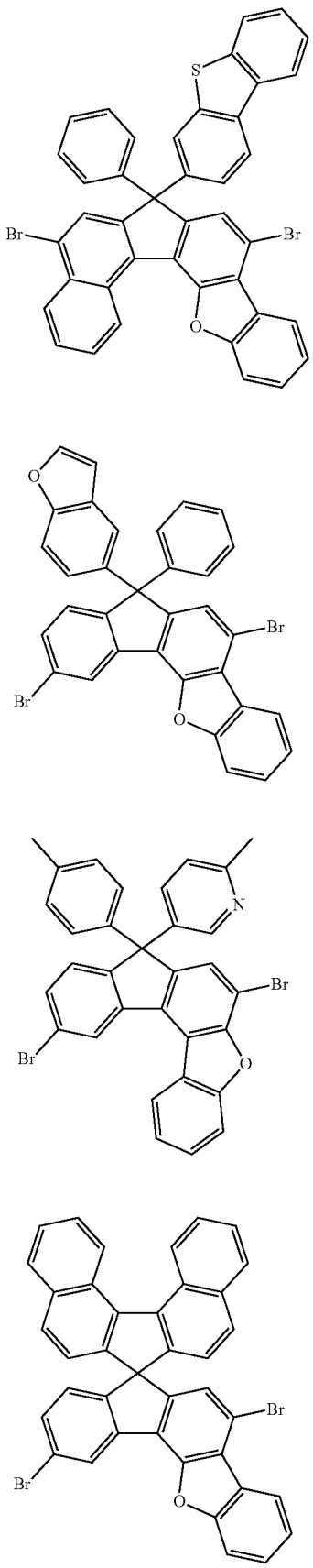

[Compound 103]

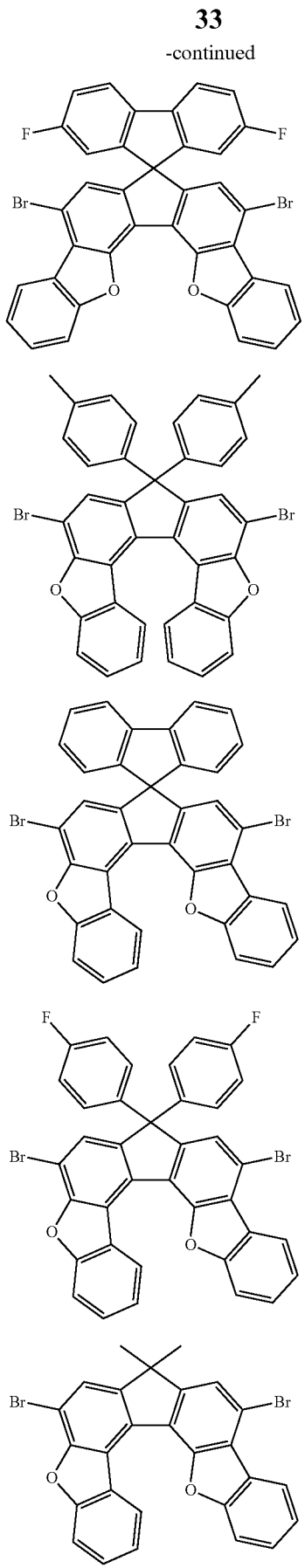

[Compound 104]

[Compound 105]

[Compound 106]

[Compound 107]

[Compound 108]

In addition, the compound represented by Chemical A or B may react with an amine to produce an amine derivative.

In one embodiment, the amine may be a primary or secondary amine. When the compound of Chemical Formula A or B reacts with a secondary amine, a tertiary amine useful as an organic luminescent material can be produced.

The reaction of the compound of Chemical Formula A or B with a secondary amine may be represented by the following Reaction Scheme A or B, respectively.

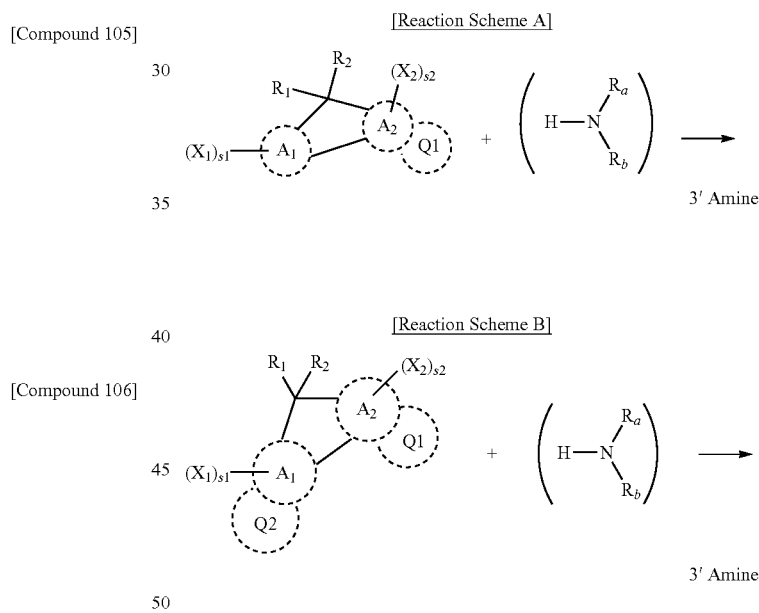

In Reaction Schemes A and B, the compounds of Chemical Formulas A and B, each serving as a starting material, are as defined above, and Ra and Rb of the secondary amine may be the same or different, and are each independently as defined for $R_1$ and $R_2$ above. In this regard, Ra and Rb of the secondary amine may each be an aryl of 6 to 40 carbon atoms.

For the reaction, the secondary amine is preferably used in an amount stoichiometrically greater than that of the leaving group of Chemical Formula A or B.

For example, when s1 and s2 are each 1 and s3 is 0 (zero) in Chemical Formula A, two or more equivalents of the secondary amine should be used.

In the tertiary amine, there may be a linker between the compound of Chemical Formula A or B and the secondary amine.

As the linker, an alkylene radical, an alkenylene radical, an alkynylene radical, a cycloalkylene radical, a heterocycloalkylene radical, an arylene radical, or a heteroarylene radical may be used. The linkers used between the secondary amine and the ring moieties $A_1$, $A_2$, E, and F of Chemical Formula A or B and may be the same or different, and are each independently selected from the group consisting of a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms and a substituted or unsubstituted heteroarylene of 2 to 60 carbon atoms.

The introduction of a substituent such as a secondary amine or an aryl radical into the compound of Chemical Formula A or B may be achieved through Suzuki coupling.

By way of example, when X1 to X4 are each a halogen atom, the substituent R, such as an amine, an aryl, etc., can be introduced as illustrated in the following Reaction Schemes A1 and B1:

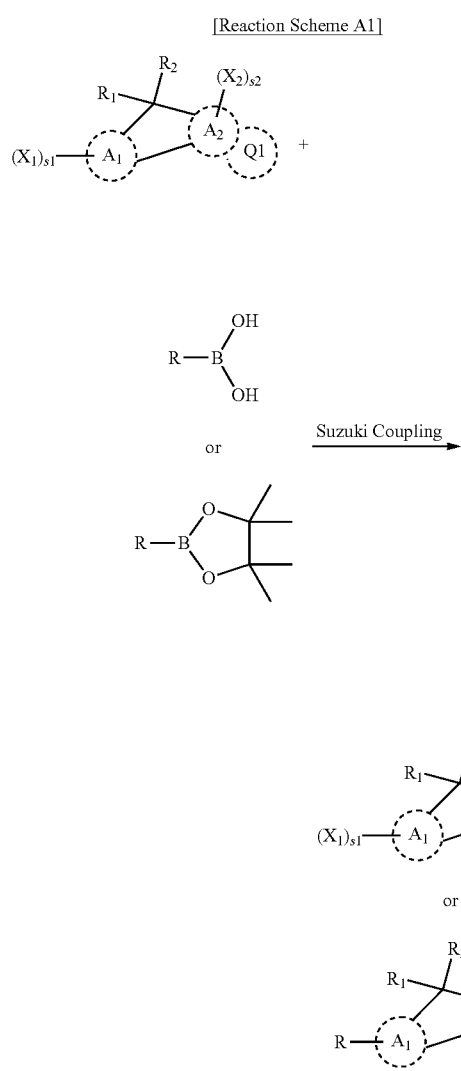

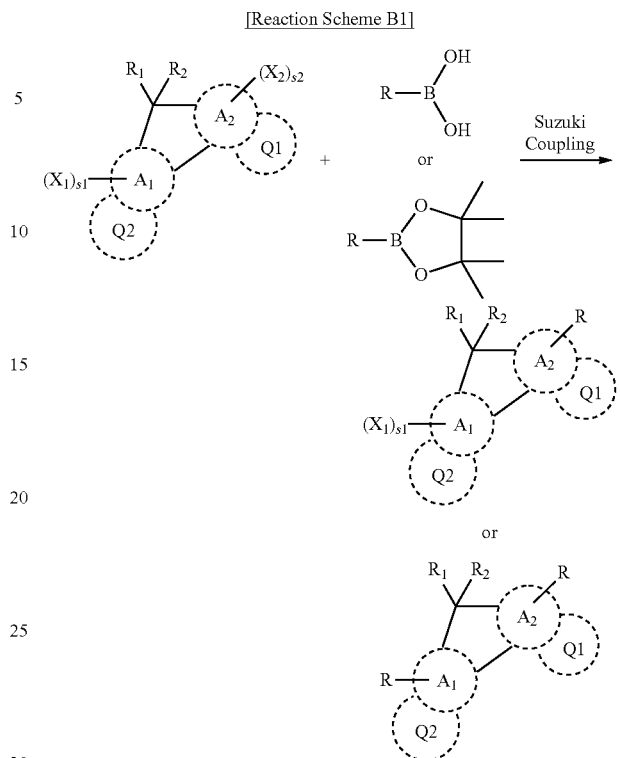

wherein the compounds of Chemical Formulas A and B, acting as starting materials in the Suzuki coupling reaction, are as defined above, and R of the boronic compound is as defined for $R_1$ or $R_2$ above.

The compound synthesized by the Suzuki coupling reaction can be used as an organic luminescent material in the present disclosure. In accordance with another aspect thereof, the present disclosure addresses an organic light-emitting diode comprising a first electrode, a second electrode facing the first electrode, and an organic layer interposed between the first electrode and the second electrode, wherein the organic layer comprises at least one of the organic luminescent compounds of the present disclosure.

For example, the compound into which an amine group is introduced, prepared as in Chemical Formula A1 or B1, can be used as an organic luminescent material in the present disclosure.

As used herein, the expression "(the organic layer) . . . comprising at least one organic compound" is construed to mean that the organic layer may comprise one or two or more different compounds that fall within the scope of the present disclosure.

In addition, the organic layer comprising the organic luminescent compound of the present disclosure may further comprise at least one of a hole injection layer, a hole transport layer, functional layer capable of both hole injection and hole transport, a light-emitting layer, an electron transport layer, and an electron injection layer, in addition to the light-emitting layer.

The organic layer interposed between the first electrode and the second electrode may include a light-emitting layer that comprises a host and a dopant, the organic luminescent compound prepared according to the present disclosure serving as the dopant.

In the light-emitting layer, a host material may be employed in addition to the dopant. When the light-emitting layer comprises both a host and a dopant, the amount of the dopant may range from about 0.01 to about 20 weight parts, based on 100 weight parts of the host, but is not limited thereto.

The material used in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum(Alq3), TAZ, Balq, beryllium bis(benzoquinolin-10-olate ($BebQ_2$), ADN, Compound 201, Compound 202, BCP, and oxadiazole derivatives such as PBD, BMD, BND, etc., but are not limited thereto.

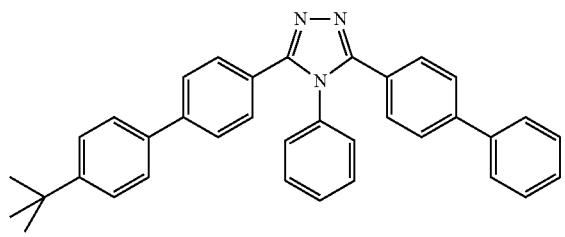

TAZ

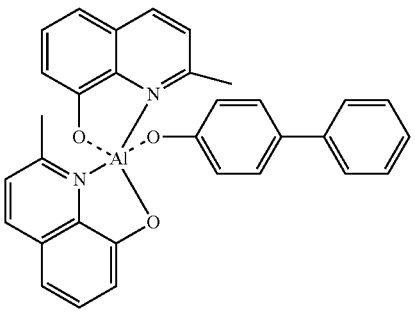

BAlq

<Compound 201>

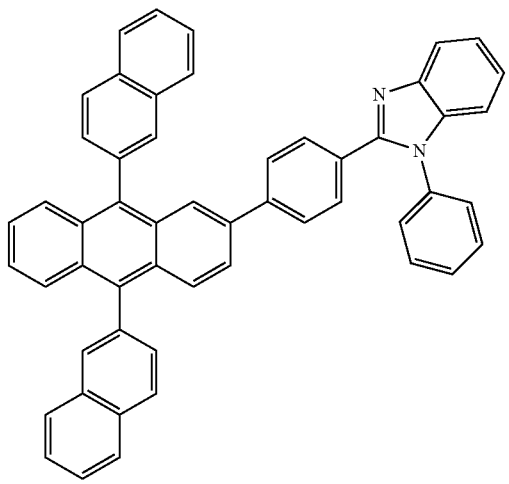

<Compound 202>

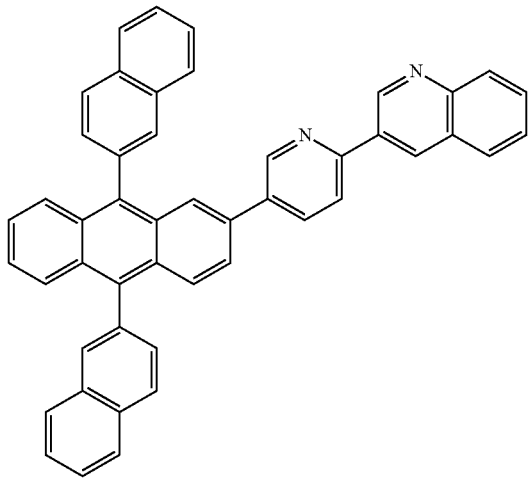

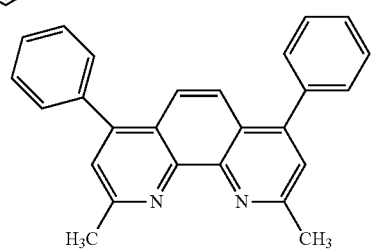

BCP

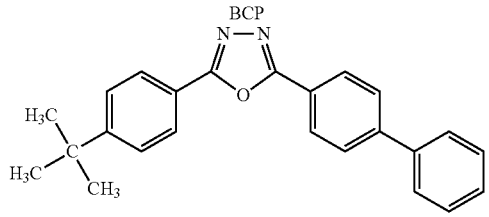

PBD

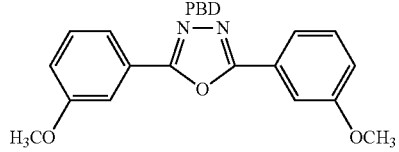

BMD

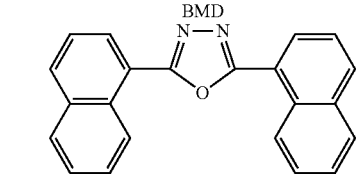

BND

Below, a description will be given of the organic light emitting diode of the present disclosure, with reference to FIG. 1.

FIG. 1 is a schematic cross-sectional view of 5 the structure of an organic light-emitting diode according to some embodiments of the present disclosure. The organic light-emitting diode comprises an anode 20, a hole transport layer 40, an organic light-emitting layer 50, an electron transport layer 60, and a cathode 80, and optionally a hole injection layer 30 and an electron injection layer 70. In addition, one or two intermediate layers may be further formed in the organic light-emitting diode, or a hole barrier layer or an electron barrier layer may also be employed.

Reference is made to FIG. 1 with regard to the fabrication of the organic light-emitting diode of the present disclosure. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, and handleability. As the anode electrode material, indium tin oxide (ITO), indium zinc oxide (IZO), tin oxide ($SnO_2$), or zinc oxide (ZnO) may be used.

A hole injection layer material is applied on the anode electrode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imposed on the hole injection layer material, as long as it is one that is typically used in the art. For example, mention may be made of 2-TNATA [4,4',4''-tris(2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine].

So long as it is typically used the art, any material may be selected for the hole transport layer without particular limitation. Examples include, but are not limited to, N,N'-bis(3-methylphenyl)-N,N'-diphenyl-[1,1-biphenyl]-4,4'-diamine (TPD) or N,N'-di(naphthalen-1-yl)-N,N'-diphenylbenzidine (a-NPD).

Then, an organic light-emitting layer 50 is deposited on the hole transport layer 40, optionally followed by the formation of a hole barrier layer (not shown) on the organic light-emitting layer by deposition in a vacuum or by spin coating. When holes traverse the organic light-emitting layer and are introduced into the cathode, the efficiency and lifetime of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium silver (Mg—Ag). For a top-emitting PLED, a transparent cathode made of ITO or IZO may be employed.

In addition, the light-emitting layer may consist of a host and a dopant.

In some embodiments of the present disclosure, the light-emitting layer particularly ranges in thickness from 50 to 2,000 Å.

By way example, the host may be selected from among compounds represented by the following [Host 1] to [Host 56], but is not limited thereto.

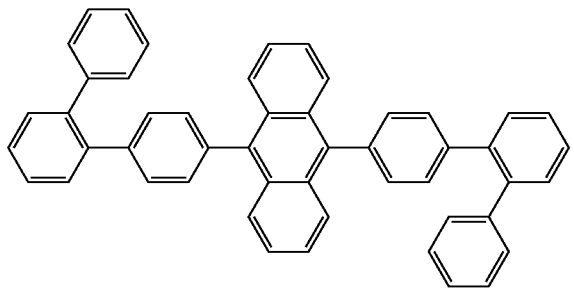
[Host1]

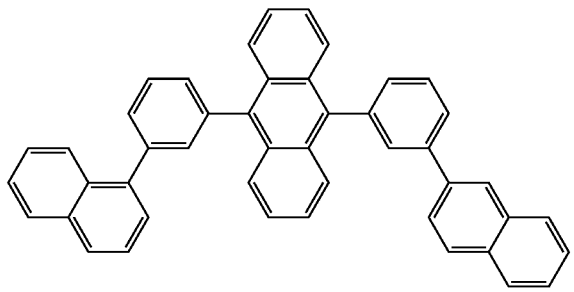
[Host2]

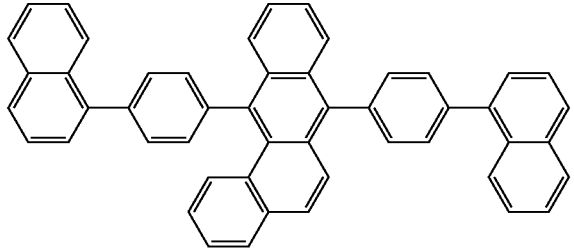
[Host3]

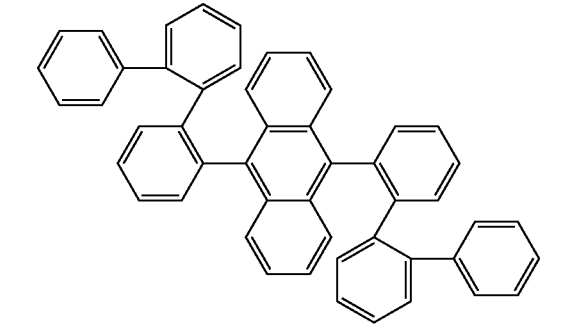
[Host4]

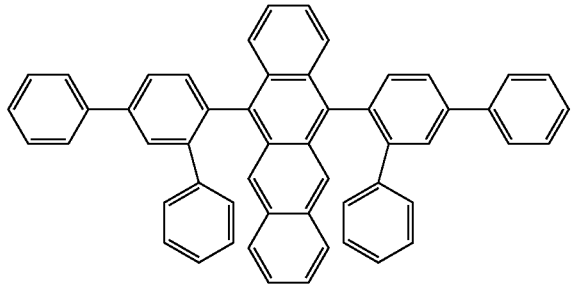
[Host5]

[Host6]
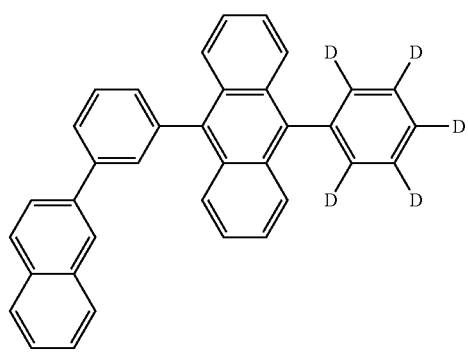
[Host10]
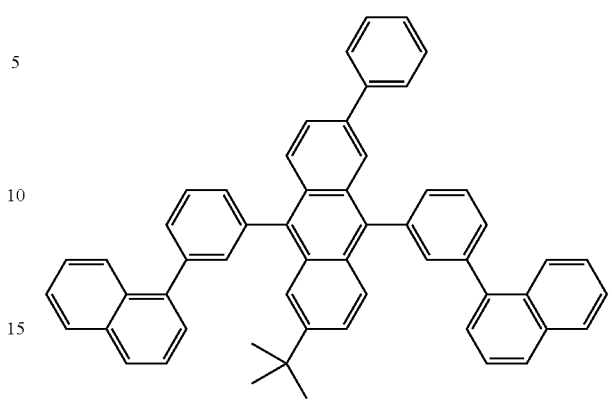
[Host7]
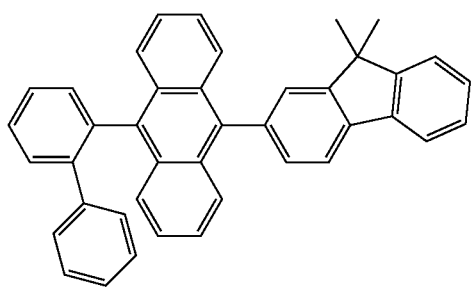
[Host11]
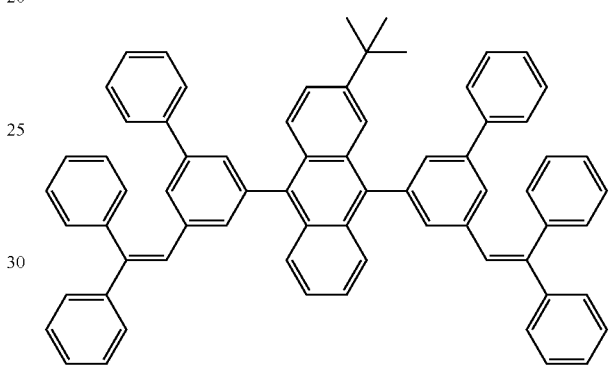
[Host8]
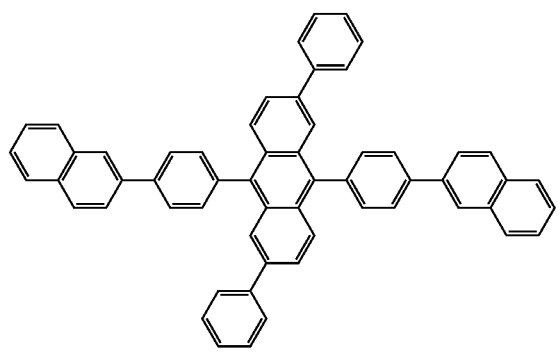
[Host12]
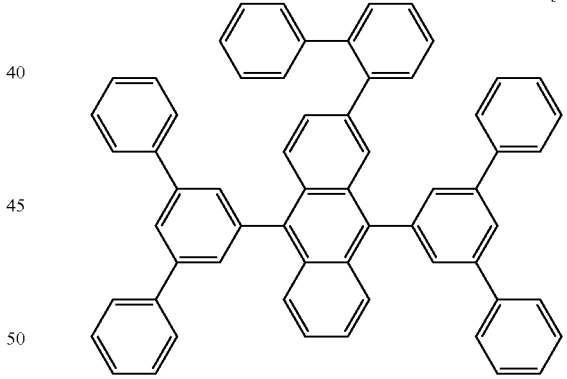
[Host9]
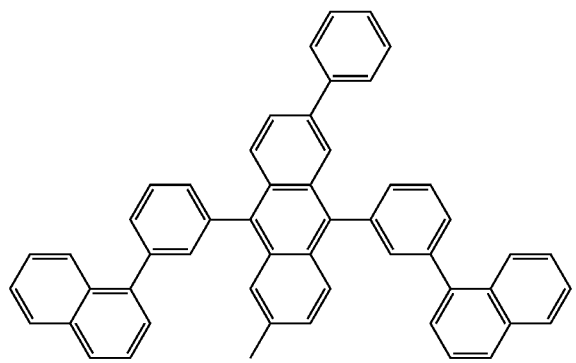
[Host13]
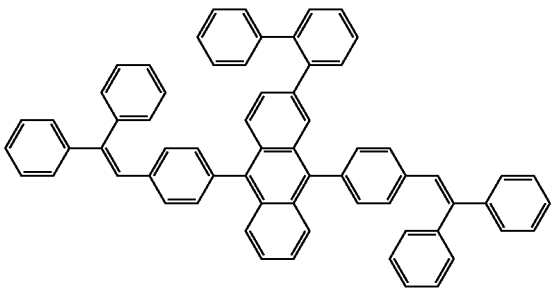

[Host14]
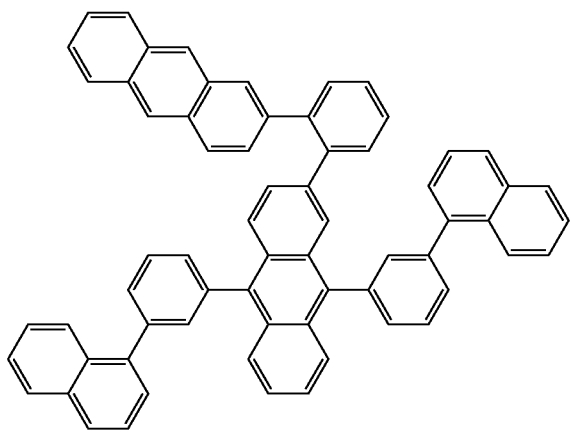
[Host15]
[Host16]
[Host17]
[Host18]
[Host19]
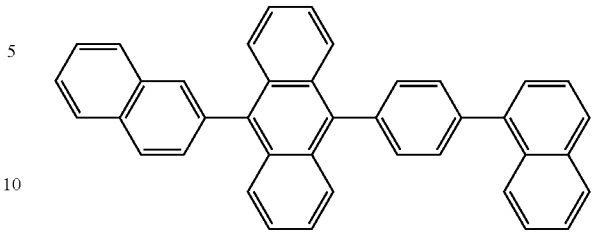
[Host20]
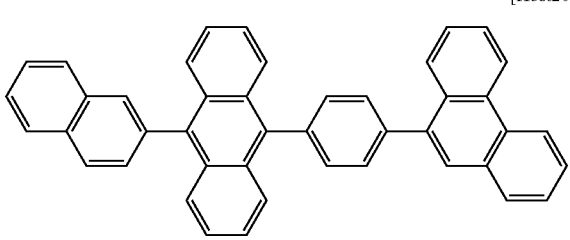
[Host21]
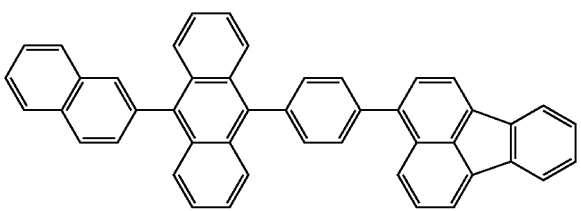
[Host22]
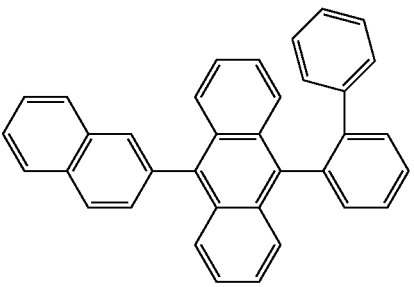
[Host23]
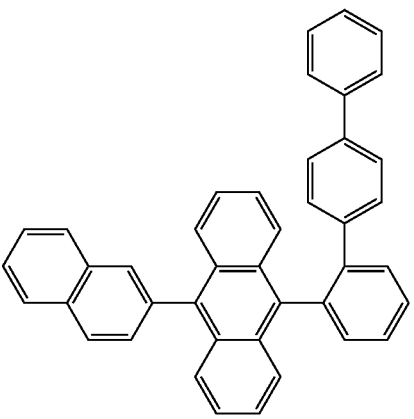

[Host24] 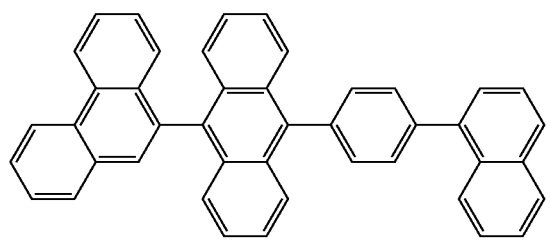
[Host29] 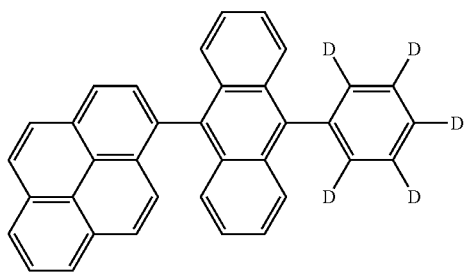
[Host25] 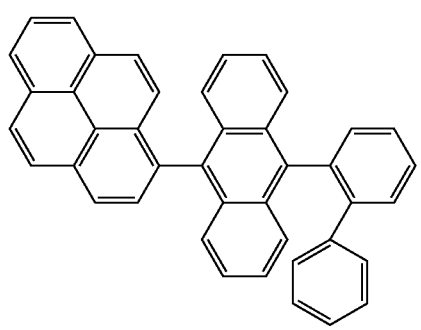
[Host30] 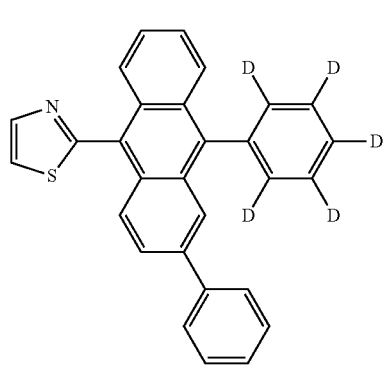
[Host26] 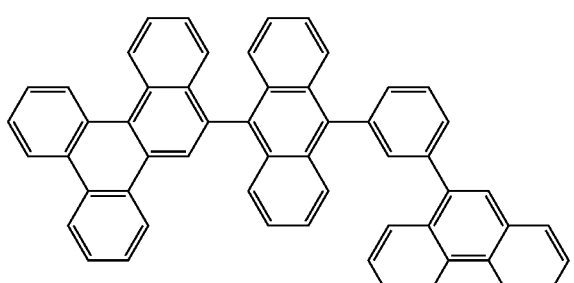
[Host31] 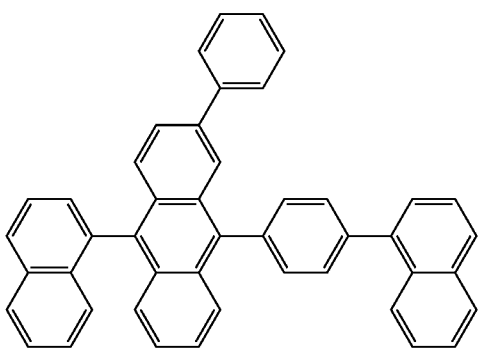
[Host27] 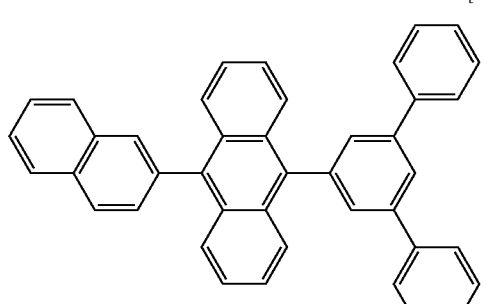
[Host32] 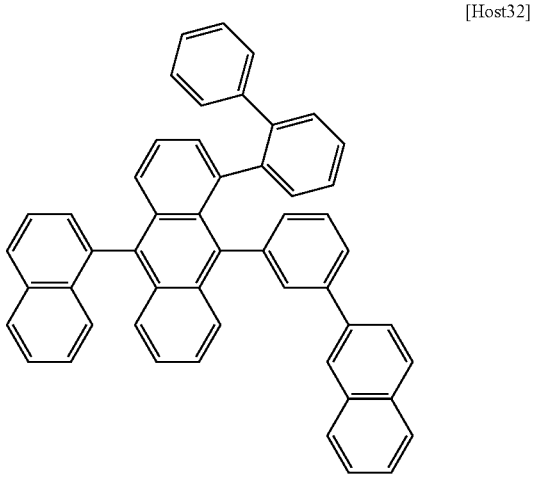
[Host28] 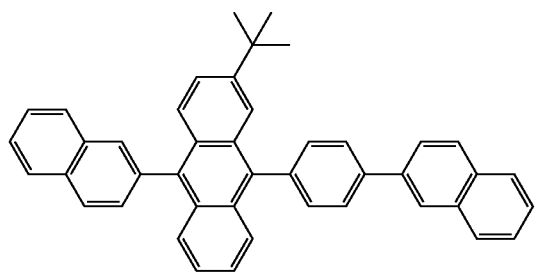

-continued
[Host33]
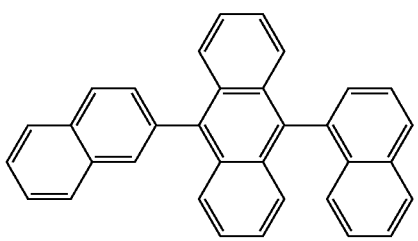
[Host34]
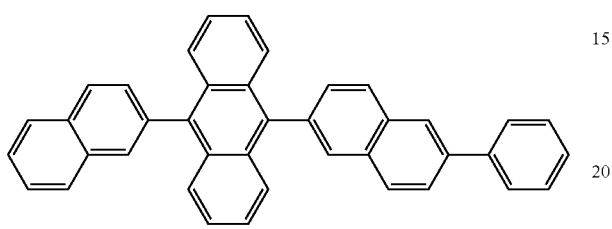
[Host35]
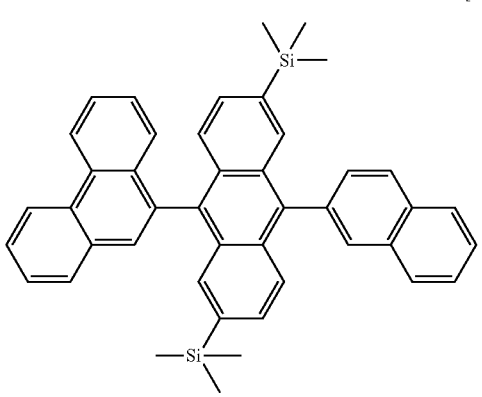
[Host36]
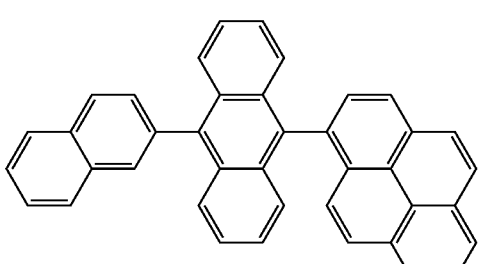
[Host37]
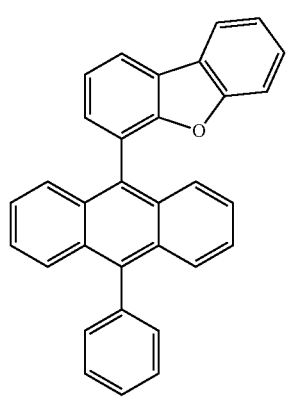
-continued
[Host38]
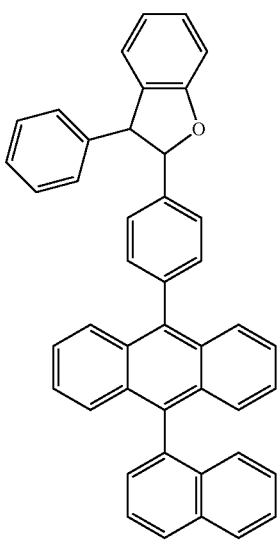
[Host39]
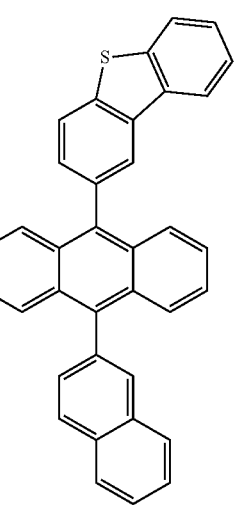
[Host40]
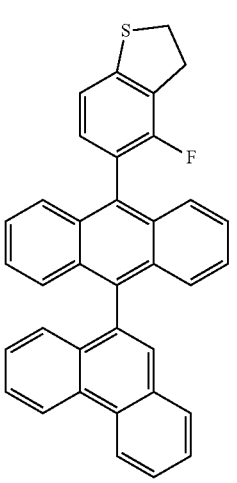

[Host41]
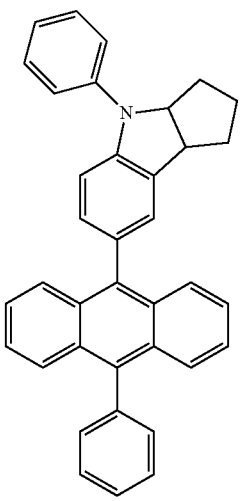
[Host45]
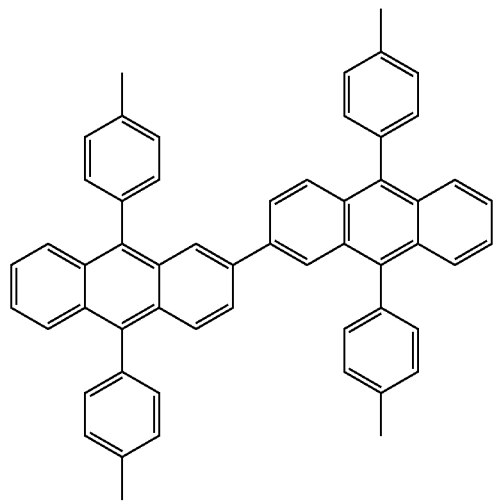
[Host42]
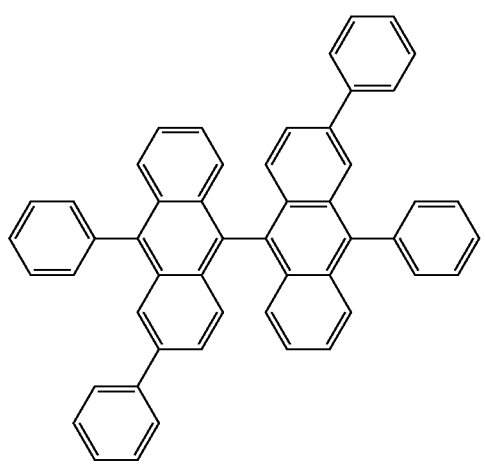
[Host46]
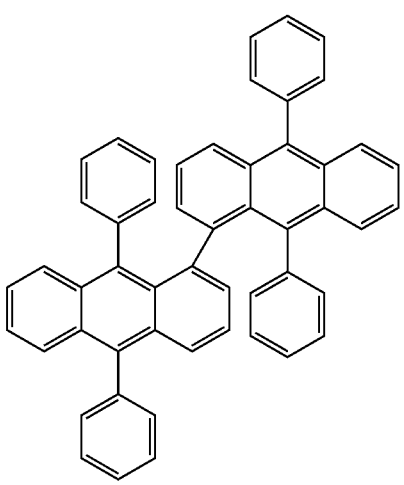
[Host43]
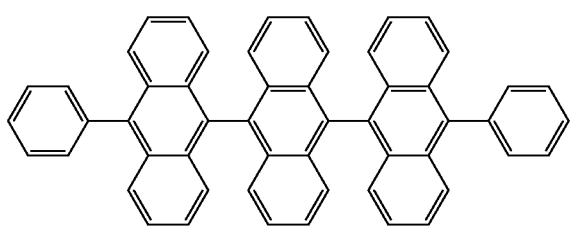
[Host44]
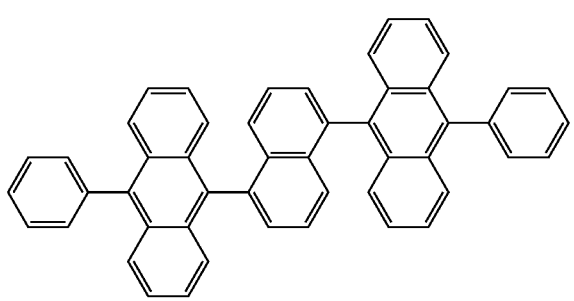
[Host47]
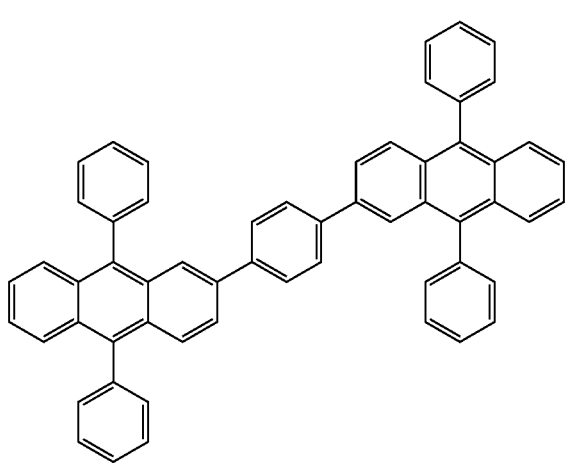

-continued
[Host48]
[Host49]
[Host50]
[Host51]
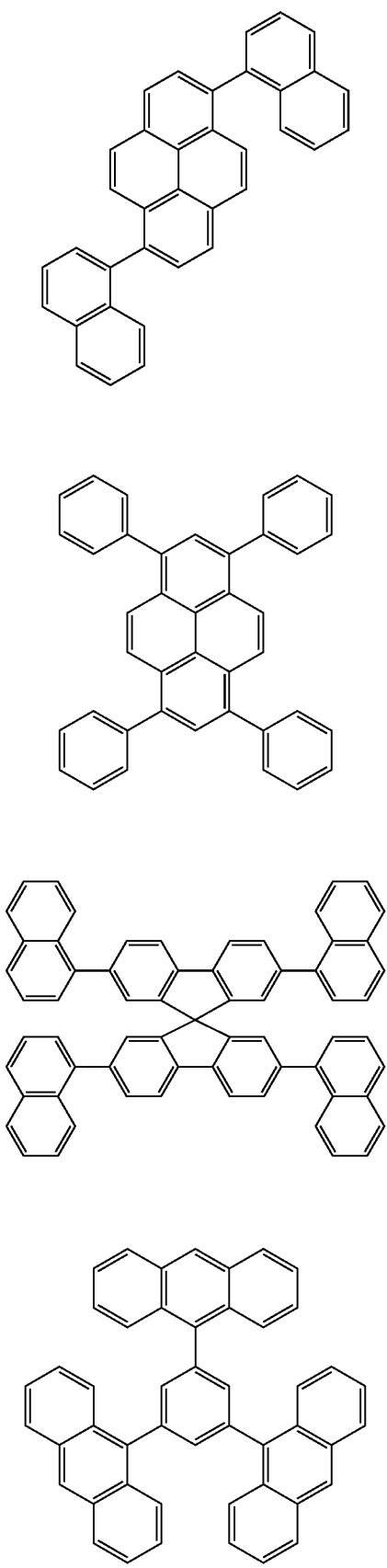
[Host52]
[Host53]
[Host54]
[Host55]
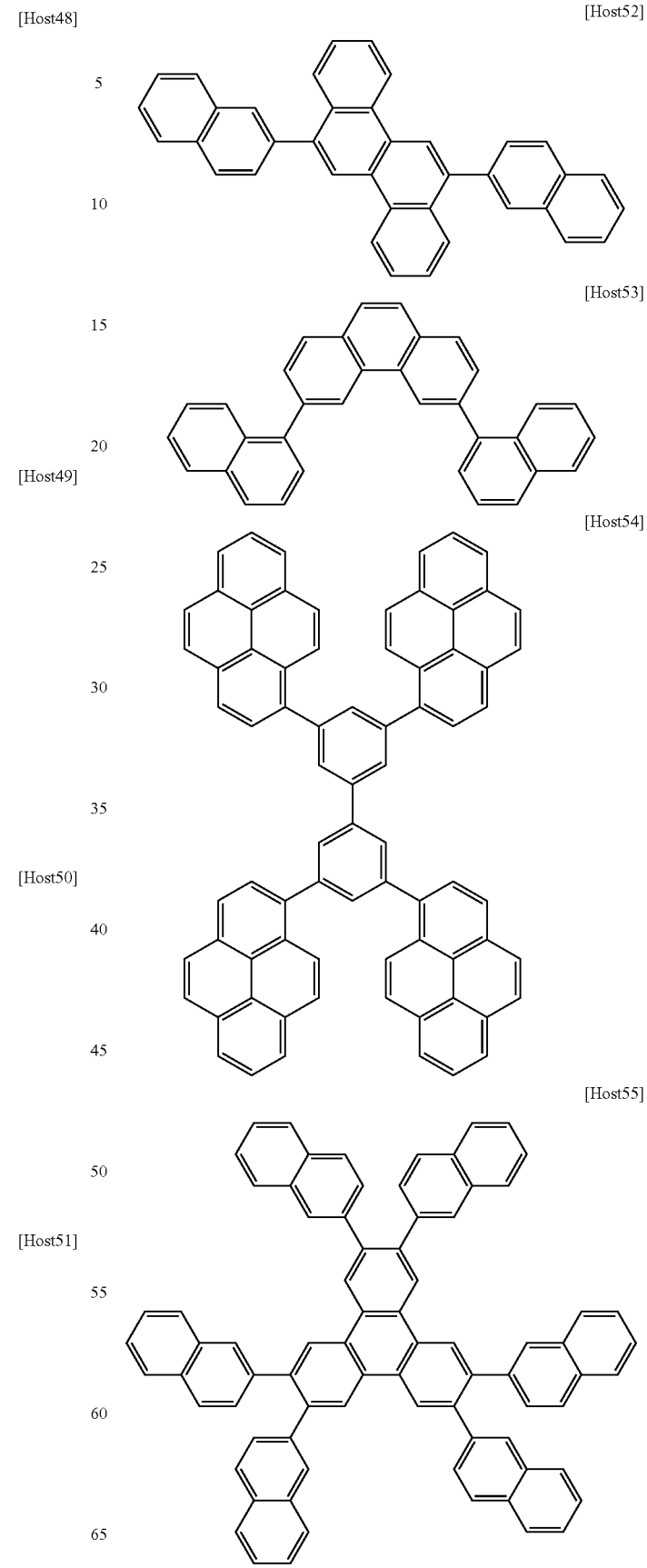

53

-continued

[Host56]

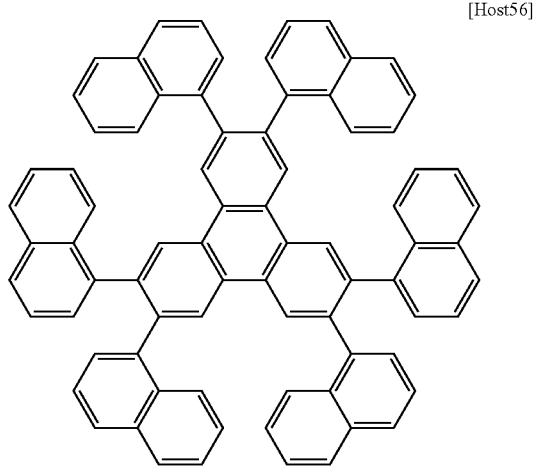

In addition to the above-mentioned dopants and hosts, the light-emitting layer may further include various hosts and dopant materials.

Further, one or more layers selected from among a hole injection layer, a hole transport layer, an electron barrier layer, a light-emitting layer, a hole barrier layer, an electron transport layer, and an electron injection layer may be deposited using a single molecule deposition process or a solution process. Here, the deposition process refers to a process by which a material is vaporized in a vacuum or at a low pressure and deposited to form a layer, and the solution process means a method in which a material is dissolved in a solvent and applied for the formation of a thin film by means of inkjet printing, roll-to-roll coating, screen printing, spray coating, dip coating, spin coating, etc.

Also, the organic light-emitting device of the present disclosure may be applied to a device selected from among flat display devices, flexible display devices, monochrome or white flat illumination devices, and monochrome or white flexible illumination devices.

A better understanding of the present disclosure may be obtained through the following examples which are set forth to illustrate, but are not to be construed as the limit of the present disclosure.

EXAMPLES

Synthesis Example 1

Synthesis of Compound 1

Synthesis Example 1-(1)

Synthesis of Intermediate 1-a

[Intermediate 1-a] was synthesized as illustrated in the following Reaction Scheme 1.

<Reaction Scheme 1>

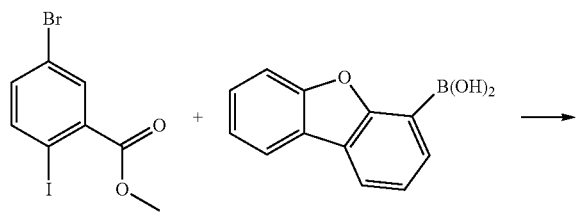

54

-continued

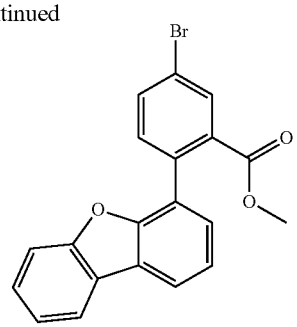

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis(triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (75.0 g, 60.1).

Synthesis Example 1-(2)

Synthesis of Intermediate 1-b

Intermediate 1-b was synthesized as illustrated in the following Reaction Scheme 2:

<Reaction Scheme 2>

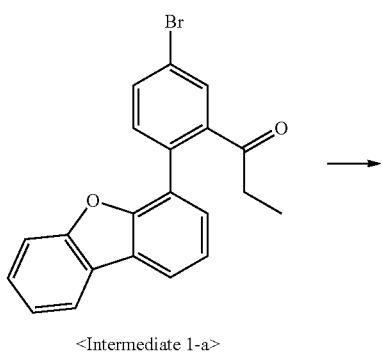

<Intermediate 1-a>

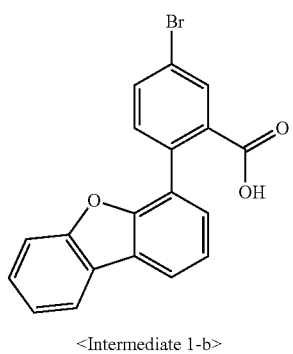

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 1-b>. (14.5 g, 88.6%)

Synthesis Example 1-(3)

Synthesis of Intermediate 1-c

Intermediate 1-c was synthesized as illustrated in the following Reaction Scheme 3:

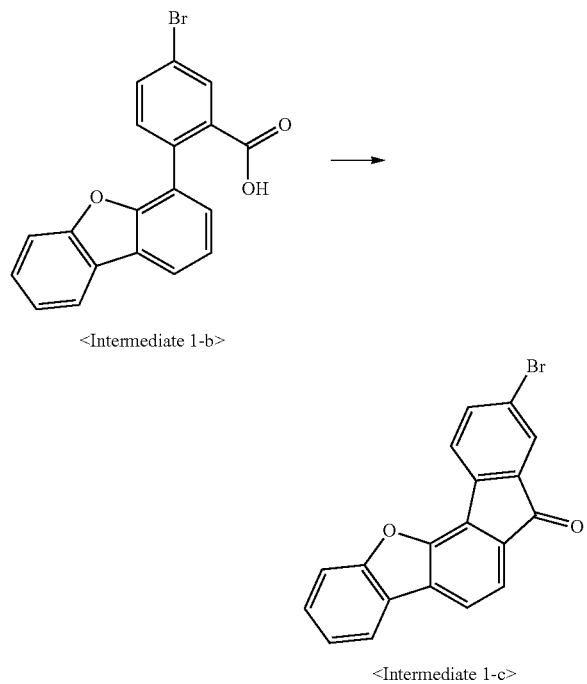

<Reaction Scheme 3>

<Intermediate 1-b>

<Intermediate 1-c>

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed using thin layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4)

Synthesis of Intermediate 1-d

Intermediate 1-d was synthesized as illustrated in the following Reaction Scheme 4:

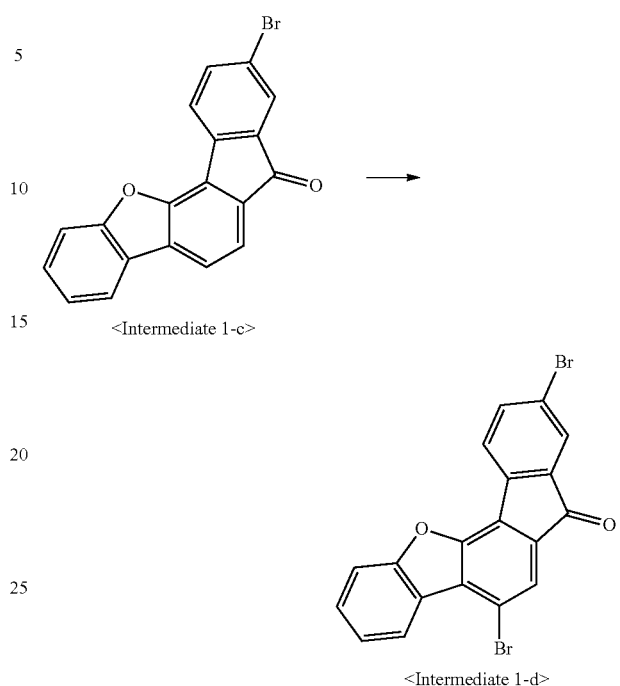

<Reaction Scheme 4>

<Intermediate 1-c>

<Intermediate 1-d>

In a 1-L round-bottom flask reactor, <Intermediate 1-c> (11.5 g, 33 mmol> and dichloromethane (300 ml) were stirred together at room temperature. A dilution of bromine (3.4 ml, 66 mmol) in dichloromethane (50 ml) was dr wise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 1-d>. (11.0 g, 78%)

Synthesis Example 1-(5)

Synthesis of Intermediate 1-e

Intermediate 1-e was synthesized as illustrated in the following Reaction Scheme 5:

<Reaction Scheme 5>

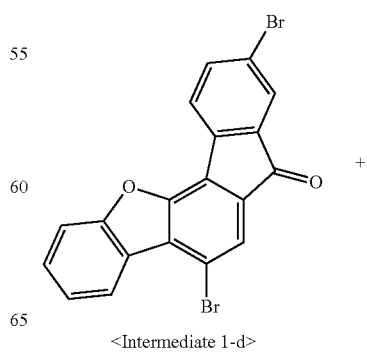

<Intermediate 1-d>

-continued

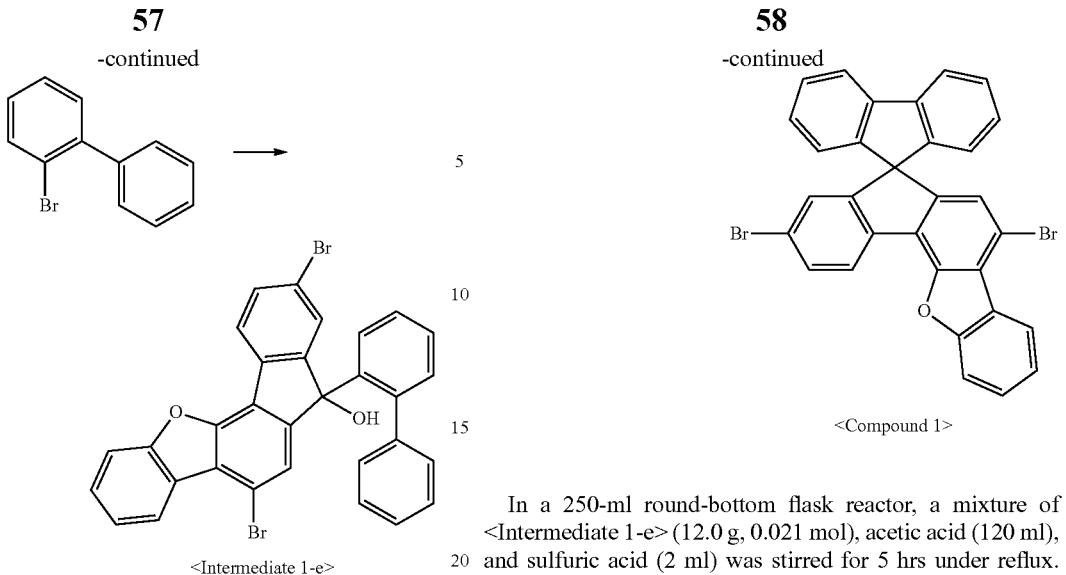

<Intermediate 1-e>

In a 250-ml round-bottom flask reactor, 2-bromobiphenyl (8.4 g, 0.036 mol) and tetrahydrofuran (110 ml) were frozen at −78° C. in a nitrogen atmosphere. At the same temperature, n-butyl lithium (19.3 ml, 0.031 mol) was dropwise added to the reaction solution, which was then stirred for 2 hrs. Thereafter, <Intermediate 1-d> (11.0 g, 0.026 mol) was added little by little to the reaction solution and stirred at room temperature. When the reaction mixture started to change color, the reaction was monitored via thin-layer chromatography. After the reaction was stopped with H$_2$O (50 ml), extraction was conducted with ethyl acetate and water. The organic layer was separated, concentrated in a vacuum, and recrystallized in acetonitrile to afford <Intermediate 1-e> as a solid. (12.2 g, 81.5%)

Synthesis Example 1-(6)

Synthesis of Compound 1

Compound 1 was synthesized as illustrated in the following Reaction Scheme 6:

<Reaction Scheme 6>

-continued

<Compound 1>

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin-layer chromatography. The reaction mixture was then cooled to room temperature and filtered. The filtrate was washed with H$_2$O and methanol and dissolved in monochlorobenzene. Following silica gel chromatography, the fraction was concentrated and cooled to room temperature to give Compound 1. (10.7 g, 90%)

Synthesis Example 1-(7)

Synthesis of Compound of Chemical Formula 1

The compound of Chemical Formula 1 was synthesized as illustrated in the following Reaction Scheme 7:

<Reaction Scheme 7>

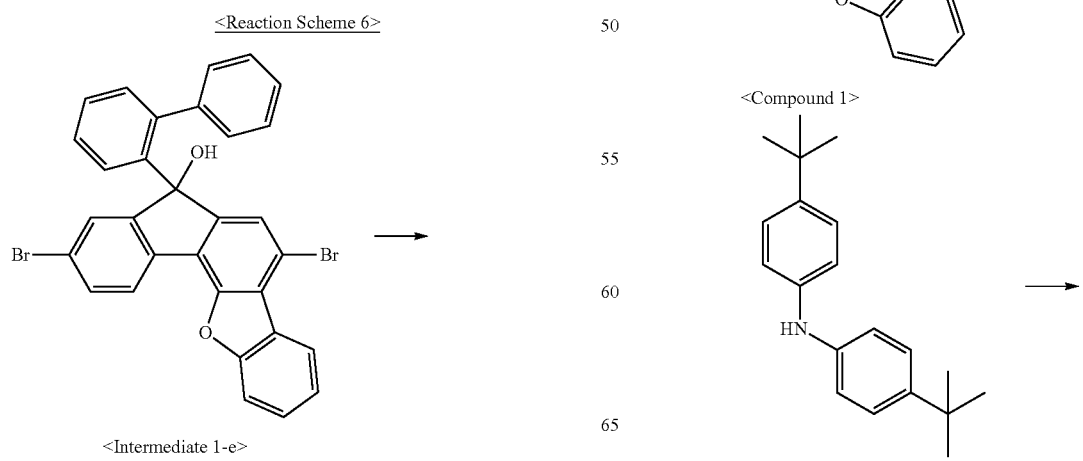

<Intermediate 1-e>

-continued

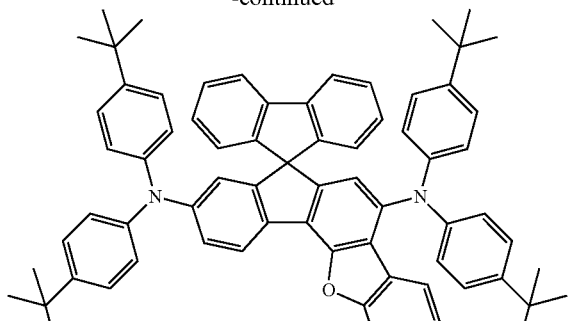

<Chemical Formula 1>

In a 250-ml round-bottom flask reactor, a mixture of <Compound 1> (5.0 g, 0.009 mol), bis(4-tert-butylphenyl)amine (6.0 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified using column chromatography and recrystallized in dichloromethane and acetone to yield the compound of Chemical Formula 1 as a solid (3.1 g, 38%).

MS (MALDI-TOF): m/z 964.5 [M$^+$]

Synthesis Example 2

Synthesis of Compound 3

Synthesis Example 2-(1)

Synthesis of Intermediate 2-a

Intermediate 2-a was synthesized as illustrated in the following Reaction Scheme 8:

<Reaction Scheme 8>

In a 2-L round-bottom flask reactor, 4-bromodibenzofuran (100 g, 0.405 mol), (1R, 2R)-cyclohexane-1,2-diamine (46.21 g, 0.404 mol), acetamide (71.7 g, 1.21 mol), copper iodide (I) (77.08 g, 0.404 mol), calcium carbonate (200 g, 0.809 mol), and toluene (1000 ml) were stirred overnight under reflux. After completion of the reaction, the reaction mixture was filtered through a celite pad and washed with ethyl acetate. The filtrate was extracted with water and ethyl acetate, and the organic layer thus formed was dried over magnesium sulfate, filtered, and concentrated in a vacuum. Recrystallization in dichloromethane and petroleum ether afforded <Intermediate 2-a> (50 g, 32%).

Synthesis Example 2-(2)

Synthesis of Intermediate 2-b

Intermediate 2-b was synthesized as illustrated in the following Reaction Scheme 9:

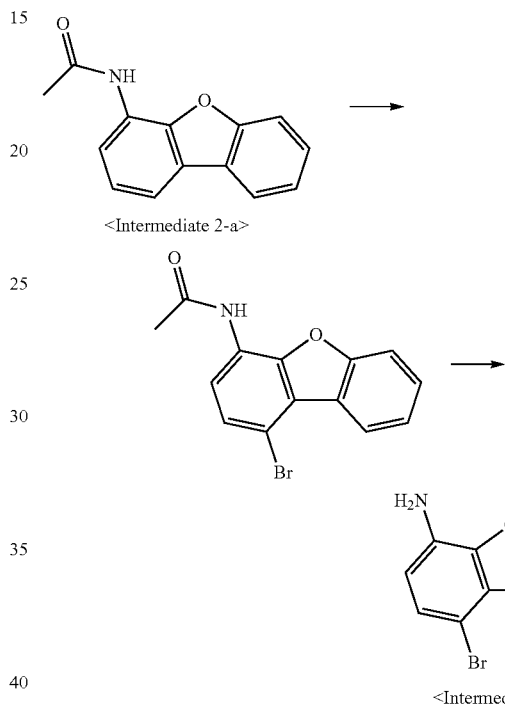

<Reaction Scheme 9>

In a 2-L round-bottom flask reactor, <Intermediate 2-a> (50 g, 0.222 mol) was dissolved in acetic acid (600 ml) by stirring at room temperature. A dilution of bromine (11.37 ml, 0.222 mol) in acetic acid (200 ml) was dropwise added to the solution and stirred for 4 hrs. After completion of the reaction, the precipitate thus formed was filtered and washed with water. The precipitate was dissolved in a mixture of 1:1:1 tetrahydrofuran/water/ethanol (1,000 ml), and stirred overnight together with potassium hydroxide (250 g, 1.11 mol) under reflux. After completion of the reaction, the reaction mixture was concentrated in a vacuum and extracted with ethyl acetate and water. The organic layer was separated, dried over magnesium sulfate, filtered, and concentrated in a vacuum. Recrystallization in ethyl acetate and heptane gave <Intermediate 2-b>. (40 g, 68.7%)

Synthesis Example 2-(3)

Synthesis of Intermediate 2-c

Intermediate 2-c was synthesized as illustrated in the following Reaction Scheme 10:

<Reaction Scheme 10>

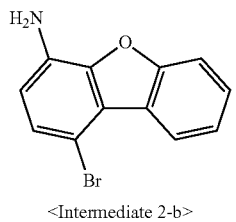

<Intermediate 2-b>

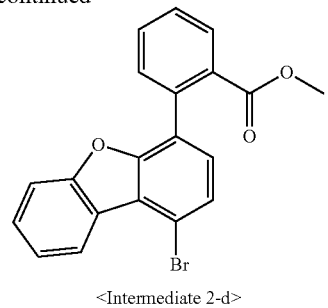

<Intermediate 2-d>

The same procedure as in Synthesis Example 1-(1), with the exception that methyl 2-bromo benzoate and <Intermediate 2-c> were used instead of methyl 5-bromo-2-iodobenzoate and <Intermediate 2-c>, respectively, was conducted to synthesize <Intermediate 2-d> (12.0 g, 67%).

Synthesis Example 2-(5)

Synthesis of Intermediate 2-e

Intermediate 2-e was synthesized as illustrated in the following Reaction Scheme 12:

<Reaction Scheme 12>

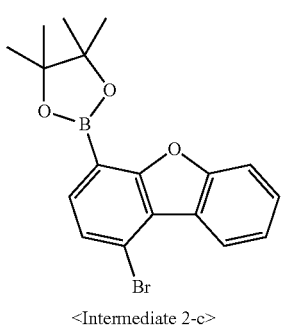

<Intermediate 2-c>

In a 1-L round-bottom flask reactor, <Intermediate 2-b> (40 g, 0.153 mol), bis(pinacolato)diboron (51.67 g, 0.183 mol), and acetonitrile (400 ml) were stirred together at room temperature. Tert-butylnitrile (26.2 g, 0.229 mol) was added little by little to the reaction solution, which was then stirred at 80° C. for 2 hrs. After completion of the reaction, the reaction mixture was cooled to room temperature. Column chromatography subsequent to vacuum concentration isolated <Intermediate 2-c> (20 g, 35%).

Synthesis Example 2-(4)

Synthesis of Intermediate 2-d

Intermediate 2-d was synthesized as illustrated in the following Reaction Scheme 11:

<Reaction Scheme 11>

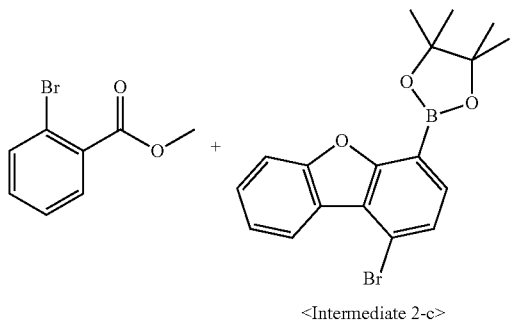

<Intermediate 2-c>

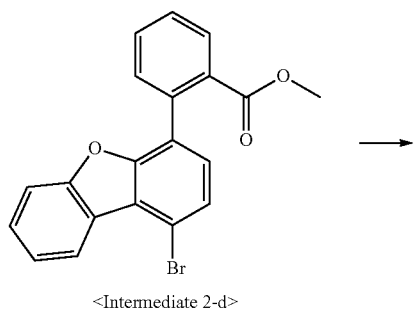

<Intermediate 2-d>

<Intermediate 2-e>

The same procedure as in Synthesis Example 1-(2), with the exception that <Intermediate 2-d> was used instead of <Intermediate 1-a>, was conducted to synthesize <Intermediate 2-e> (10.0 g, 86%).

Synthesis Example 2-(6)

Synthesis of Intermediate 2-f

Intermediate 2-f was synthesized as illustrated in the following Reaction Scheme 13:

<Reaction Scheme 13>

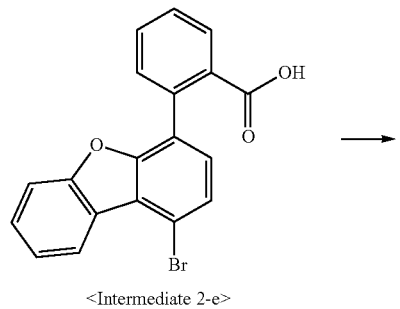

<Intermediate 2-e>

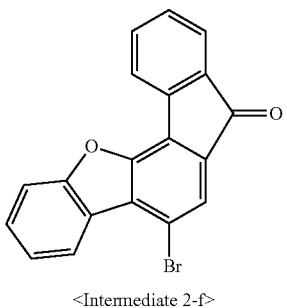

<Intermediate 2-f>

The same procedure as in Synthesis Example 1-(3), with the exception that <Intermediate 2-e> was used instead of <Intermediate 1-b>, was conducted to synthesize <Intermediate 2-f> (8.4 g, 88%).

Synthesis Example 2-(7)

Synthesis of Intermediate 2-g

Intermediate 2-g was synthesized as illustrated in the following Reaction Scheme 14:

<Reaction Scheme 14>

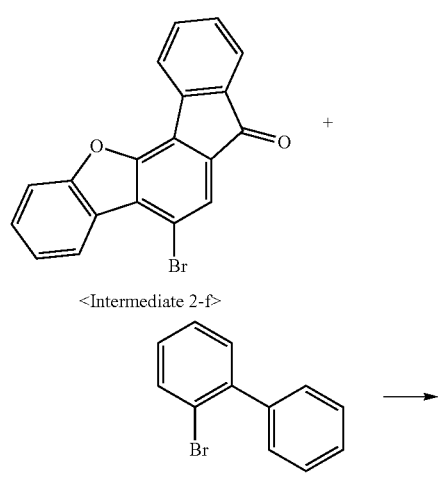

<Intermediate 2-f>

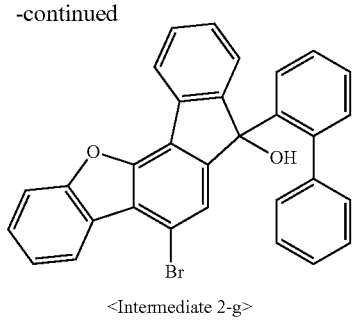

<Intermediate 2-g>

The same procedure as in Synthesis Example 1-(5), with the exception that <Intermediate 2-f> was used instead of <Intermediate 1-d>, was conducted to synthesize <Intermediate 2-g> (8 g, 66%).

Synthesis Example 2-(8)

Synthesis of Compound 3

Compound 3 was synthesized as illustrated in the following Reaction Scheme 15:

<Reaction Scheme 15>

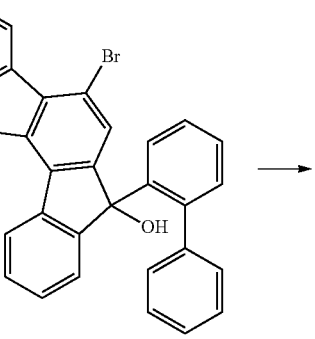

<Intermediate 2-g>

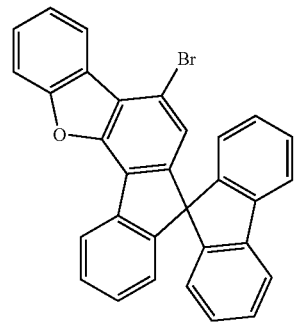

<Compound 3>

The same procedure as in Synthesis Example 1-(6), with the exception that <Intermediate 2-g> was used instead of <Intermediate 1-e>, was conducted to synthesize <Compound 3> (5.8 g, 74%).

Synthesis Example 2-(9)

Synthesis of Compound of Chemical Formula 2

The compound of Chemical Formula 2 was synthesized as illustrated in the following Reaction Scheme 16:

<Reaction Scheme 16>

<Compound 3> + diphenylamine → <Chemical Formula 2>

The same procedure as in Synthesis Example 1-(7), with the exception that Compound 3 and diphenylamine were used instead of Compound 1 and bis(4-tert-butylphenyl) amine, respectively, was conducted to synthesize the compound of Chemical Formula 2 (2.7 g, 29%).

MS (MALDI-TOF): m/z 573.21 [M$^+$]

Synthesis Example 3

Synthesis of Compound 10

Synthesis Example 3-(1)

Synthesis of Intermediate 3-a

Intermediate 3-a was synthesized as illustrated in the following Reaction Scheme 17:

<Reaction Scheme 17>

→ <Intermediate 3-a>

In a 500-ml round-bottom flask reactor, 1-bromo 3-iodobenzene (25.0 g, 88 mmol) was dissolved in tetrahydrofuran (200 ml). This solution was cooled to −78° C. and slowly added with drops of N-butyl lithium (60.75 ml, 97 mmol) over 30 min while stirring for 1 hr. At the same temperature, trimethyl borate (11 g, 106 mmol) was dropwise added to the reaction mixture, which was then stirred overnight at room temperature. Acidification with drops of 2-N HCl was performed, followed by stirring for 1 hr. Extraction with ethyl acetate formed an organic layer which was then isolated and concentrated in a vacuum. Crystallization in chilled normal hexane afforded <Intermediate 3-a>. (12 g, 67.6%)

Synthesis Example 3-(2)

Synthesis of Intermediate 3-b

Intermediate 3-b was synthesized as illustrated in the following Reaction Scheme 18:

<Reaction Scheme 18>

+ <Intermediate 3-a> → <Intermediate 3-b>

The same procedure as in Synthesis Example 1-(2), with the exception that methyl 2-bromobenzoate and <Intermediate 3-a> were used instead of methyl 5-bromo-2-iodobenzoate and dibenzofuran boronic acid, respectively, was conducted to synthesize <intermediate 3-b> (10.2 g, 68.5%).

Synthesis Example 3-(3)

Synthesis of Intermediate 3-c

Intermediate 3-c was synthesized as illustrated in the following Reaction Scheme 19:

Reaction Scheme 19

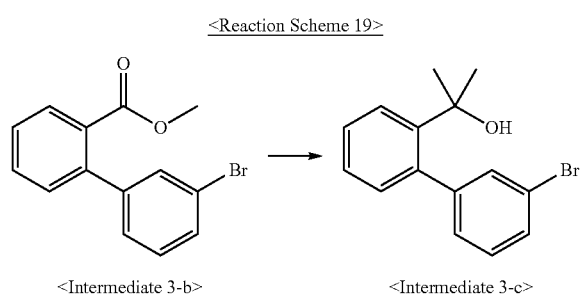 [SMILES: COC(=O)c1ccccc1-c1cccc(Br)c1 ; CC(C)(O)c1ccccc1-c1cccc(Br)c1]

<Intermediate 3-b>    <Intermediate 3-c>

In a 250-ml round-bottom flask, a mixture of <Intermediate 3-b> (10.2 g, 35 mmol) and tetrahydrofuran (100 ml) was cooled to 0° C. in a nitrogen atmosphere. After methyl magnesium bromide (17.5 ml, 53 mmol) was dropwise added to the chilled reaction solution, it was stirred for 2 hrs at room temperature and then for 2 hrs under reflux and cooled to room temperature. The reaction mixture was acidified with drops of 0.2 N HCl and extracted with ethyl acetate and water. The organic layer was isolated, concentrated in vacuum, and purified through a column to afford <Intermediate 3-c> (7.6 g, 74.5%).

Synthesis Example 3-(4)

Synthesis of Intermediate 3-d

Intermediate 3-d was synthesized as illustrated in the following Reaction Scheme 20:

Reaction Scheme 20

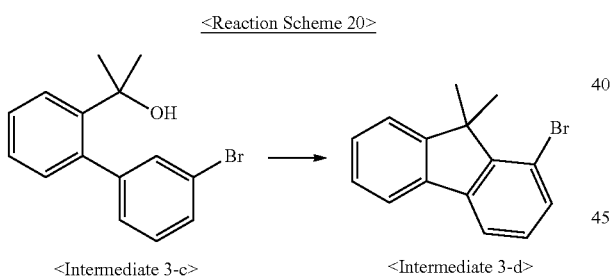

<Intermediate 3-c>    <Intermediate 3-d>

In a 500-ml round-bottom flask, <Intermediate 3-c> (20.0 g, 69 mmol), acetic acid (300 ml), and HCl (1 ml) were stirred together under reflux. After completion of the reaction was confirmed using thin-layer chromatography, the reaction mixture was cooled to room temperature. Extraction was conducted with methylene chloride and water. The organic layer was isolated and concentrated in a vacuum. Purification through column chromatography afforded <Intermediate 3-d> (8.2 g, 43.7%).

Synthesis Example 3-(5)

Synthesis of Intermediate 3-e

Intermediate 3-e was synthesized as illustrated in the following Reaction Scheme 21:

Reaction Scheme 21

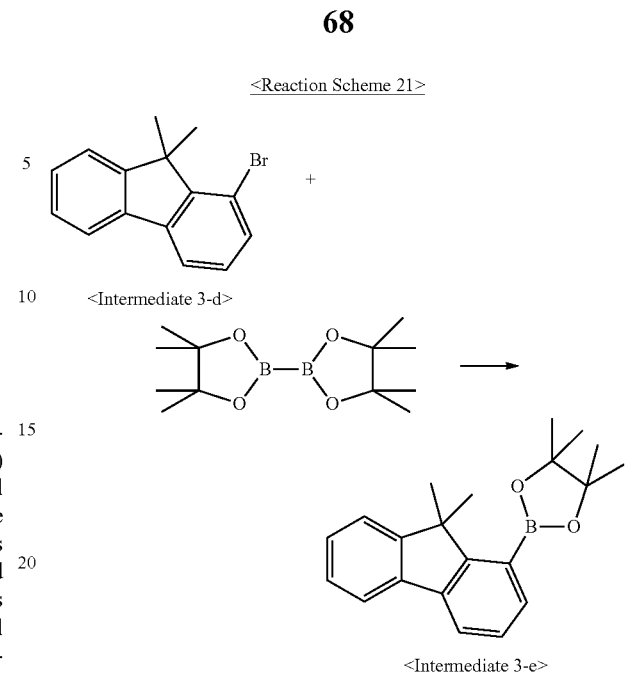

<Intermediate 3-d>

<Intermediate 3-e>

In a 250-ml round-bottom flask reactor, <Intermediate 3-d> (8.2 g, 30 mmol), bis(pinacolato)diboron (9.9 g, 39 mmol), [1,1'-bis(diphenylphosphino)ferrocene]dichloropalladium (0.5 g, 0.001 mol), potassium acetate (7.4 g, 75 mmol), and 1,4-dioxane (80 ml) were stirred together for 10 hrs under reflux. After completion of the reaction, filtration through a celite pad was conducted. The filtrate was concentrated in a vacuum, purified through a column, and recrystallized in dichloromethane and heptane to afford <Intermediate 3-e> (7.0 g, 72.8%).

Synthesis Example 3-(6)

Synthesis of Intermediate 3-f

Intermediate 3-f was synthesized as illustrated in the following Reaction Scheme 22:

Reaction Scheme 22

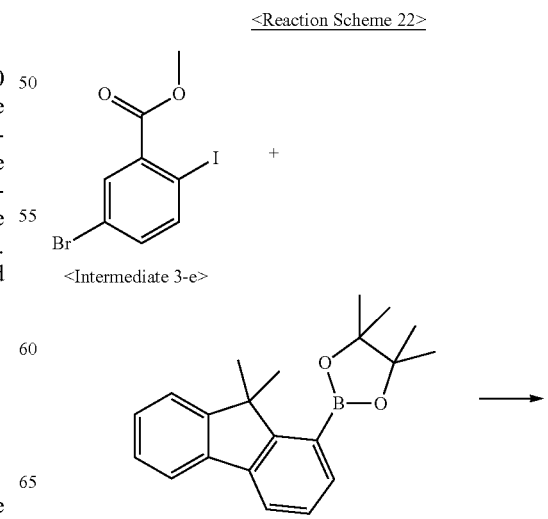

<Intermediate 3-e>

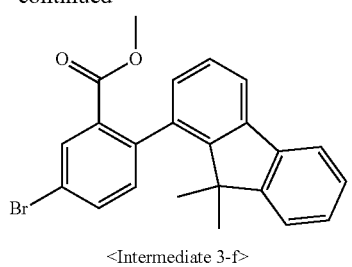

<Intermediate 3-f>

The same procedure as in Synthesis Example 1-(1), with the exception that <Intermediate 3-e> was used instead of 4-d benzofuran boronic acid, was conducted to synthesize <Intermediate 3-f> (8.2 g, 68.6%).

Synthesis Example 3-(7)

Synthesis of Intermediate 3-g

Intermediate 3-g was synthesized as illustrated in the following Reaction Scheme 23:

<Reaction Scheme 23>

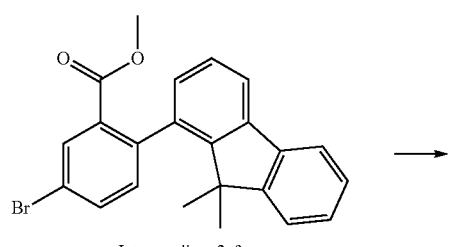

<Intermediate 3-f>

→

<Intermediate 3-g>

The same procedure as in Synthesis Example 1-(2), with the exception that <Intermediate 3-f> was used instead of <Intermediate 1-a>, was conducted to synthesize <Intermediate 3-g> (6.5 g, 82.1%).

Synthesis Example 3-(8)

Synthesis of Intermediate 3-h

Intermediate 3-h was synthesized as illustrated in the following Reaction Scheme 24:

<Reaction Scheme 24>

<Intermediate 3-g>

<Intermediate 3-h>

The same procedure as in Synthesis Example 1-(3), with the exception that <Intermediate 3-g> was used instead of <Intermediate 1-b>, was conducted to synthesize <Intermediate 3-h> (5.0 g, 80.6%).

Synthesis Example 3-(9)

Synthesis of Intermediate 3-i

Intermediate 3-i was synthesized as illustrated in the following Reaction Scheme 25:

<Reaction Scheme 25>

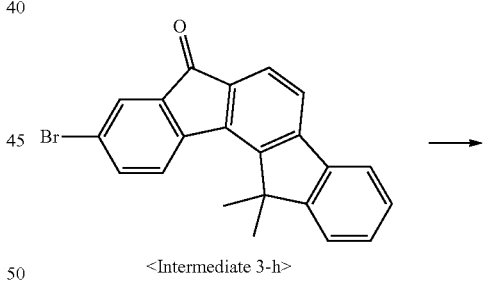

<Intermediate 3-h>

<Intermediate 3-i>

The same procedure as in Synthesis Example 1-(4), with the exception that <Intermediate 3-h> was used instead of <Intermediate 1-c>, was conducted to synthesize <Intermediate 3-i> (3.5 g, 57.8%).

Synthesis Example 3-(10)

Synthesis of Intermediate 3-j

Intermediate 3-j was synthesized as illustrated in the following Reaction Scheme 26:

<Reaction Scheme 26>

<Intermediate 3-i>

<Intermediate 3-j>

The same procedure as in Synthesis Example 1-(5), with the exception that <Intermediate 3-i> was used instead of <Intermediate 1-d>, was conducted to synthesize <Intermediate 3-j> (3.0 g, 64%).

Synthesis Example 3-(11)

Synthesis of Compound 10

Compound 10 was synthesized as illustrated in the following Reaction Scheme 27:

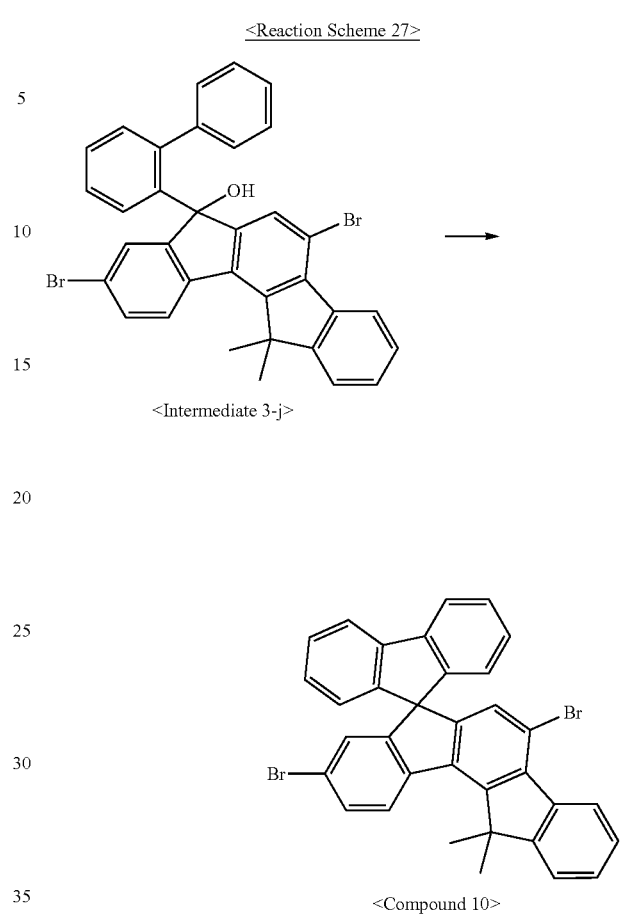

<Reaction Scheme 27>

<Intermediate 3-j>

<Compound 10>

The same procedure as in Synthesis Example 1-(6), with the exception that <Intermediate 3-j> was used instead of <Intermediate 1-e>, was conducted to synthesize <Compound 10> (2.2 g, 75.6%).

Synthesis Example 3-(12)

Synthesis of Compound of Chemical Formula 3

The compound of Chemical Formula 3 was synthesized as illustrated in the following Reaction Scheme 28:

<Reaction Scheme 28>

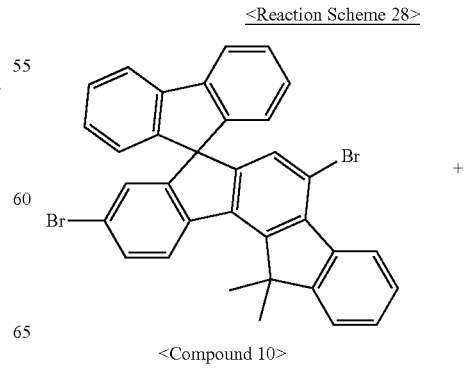

<Compound 10>

-continued

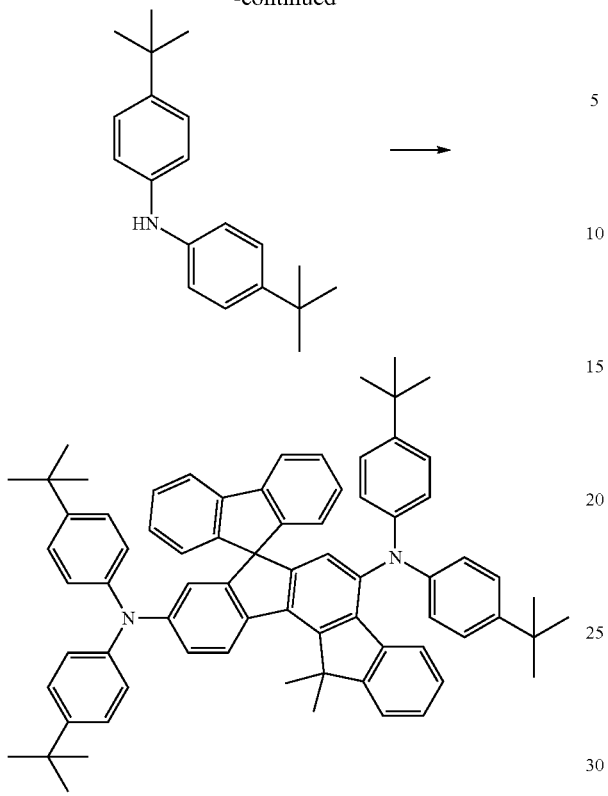

<Chemical Formula 3>

The same procedure as in Synthesis Example 1-(7), with the exception that <Compound 10> was used instead of <Compound 1>, was conducted to synthesize the compound of <Chemical Formula 3> (1.8 g, 48.7%).

Synthesis Example 4

Synthesis of Compound of Chemical Formula 29

Synthesis Example 4-(1)

Synthesis of Intermediate 4-a

Intermediate was synthesized as illustrated in the following Reaction Scheme 29:

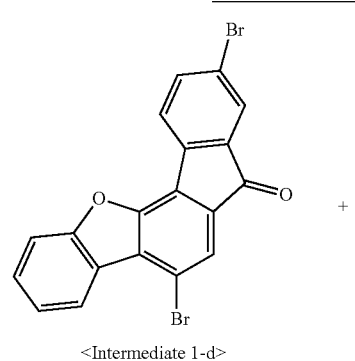

<Reaction Scheme 29>

In a 500-mL round-bottom flask reactor, 1,2-dibromobenzene (20.0 g, 0.085 mol), 4-fluorobenzobronic acid (14.2 g, 0.102 mol), tetrakis (triphenylphosphine)palladium (2.9 g, 0.0025 mmol), and potassium carbonate (23.4 g, 0.169 mol) were placed, followed by toluene (100 mL), tetrahydrofuran (100 mL) and water (40 mL). The reaction mixture was heated to 80° C. and stirred for 10 hrs. After completion of the reaction, the reaction mixture was cooled to room temperature and extracted with ethyl acetate. The organic layer was isolated and concentrated in a vacuum. Purification through column chromatography afforded Intermediate 4-a (14.1 g, 66.2%)

Synthesis Example 4-(2)

Synthesis of Intermediate 4-b

Intermediate 4-b was synthesized as illustrated in the following Reaction Scheme 30:

<Reaction Scheme 30>

The same procedure as in Synthesis Example 1-(5), with the exception that <Intermediate 4-a> was used instead of 2-bromobiphenyl, was conducted to synthesize <Intermediate 4-b> (12.2 g, 79%).

Synthesis Example 4-(3)

Synthesis of Compound 29

Compound 29 was synthesized as illustrated in the following Reaction Scheme 31:

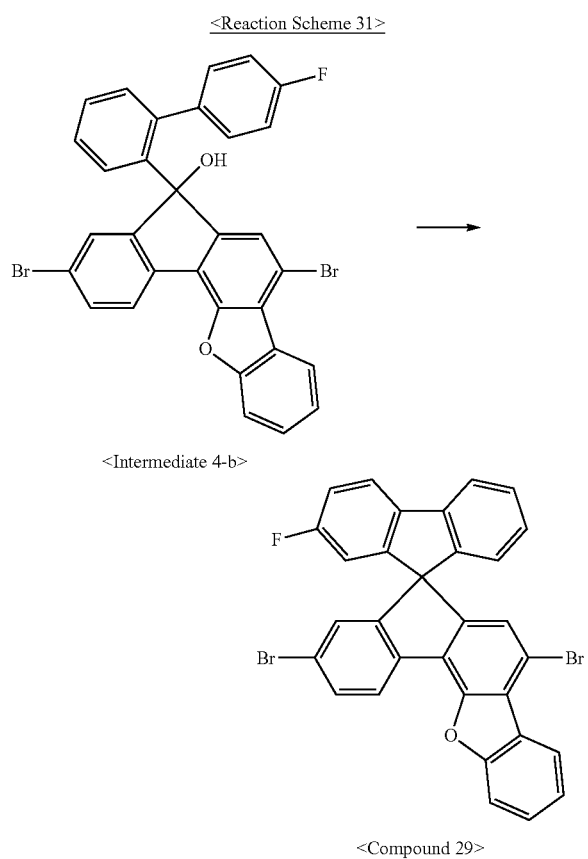

The same procedure as in Synthesis Example 1-(6), with the exception that <Intermediate 4-b> was used instead of <Intermediate 1-e>, was conducted to synthesize <Compound 29> (8.2 g, 69.3%).

Synthesis Example 4-(4)

Synthesis of Intermediate 4-c

Intermediate 4-c was synthesized as illustrated in the following Reaction Scheme 32:

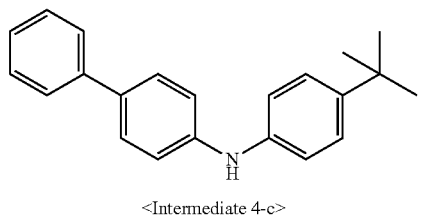

<Intermediate 4-c>

In a 250-ml round-bottom flask reactor, 4-bromobiphenyl (8.2 g, 0.035 mol), 4-tert-butyl aniline (5.8 g, 0.039 mol), tris(dibenzylidene acetone)dipalladium(0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together for 3 hrs under reflux. After completion of the reaction, the reaction mixture was cooled to room temperature and extracted with ethyl acetate and water. The organic layer was isolated, dried over magnesium sulfate, and concentrated in a vacuum. Purification through column chromatography gave <Intermediate 4-c>. (7.6 g, 72%).

Synthesis Example 4-(5)

Synthesis of Compound of Chemical Formula 4

The compound of Chemical Formula 4 was synthesized as illustrated in the following Reaction Scheme 33:

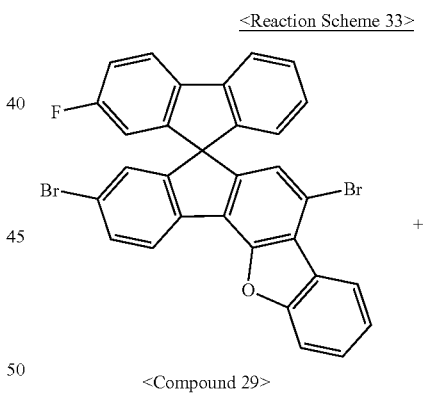

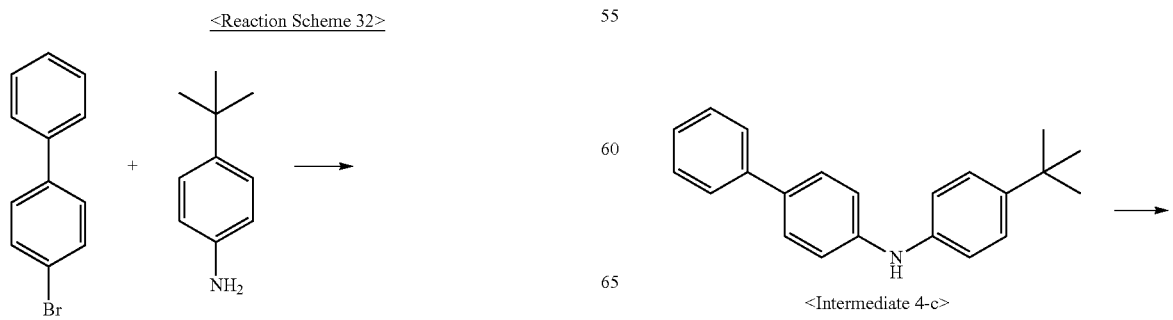

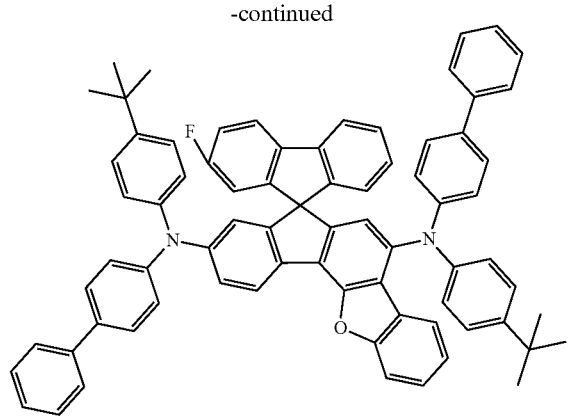

<Chemical Formula 4>

The same procedure as in Synthesis Example 1-(7), with the exception that <Compound 29> and <Intermediate 4-c> were used instead of <Compound 1> and bis(4-tert-butylphenyl)amine, respectively, was conducted to synthesize the compound of <Chemical Formula 4> (2.4 g, 28%).

MS (MALDI-TOF): m/z 1022.4 [M$^+$]

Synthesis Example 5

Synthesis of Compound of Chemical Formula 49

Synthesis Example 5-(1)

Synthesis of Intermediate 5-a

Intermediate 5-a was synthesized as illustrated in the following Reaction Scheme 34:

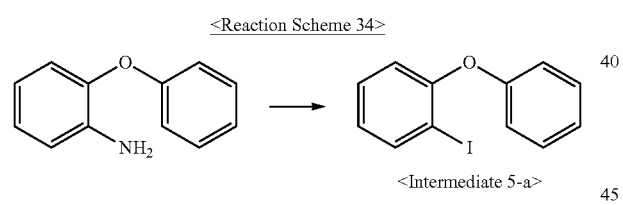

In a 1-L round-bottom flask reactor, a mixture of 2-phenoxyaniline (25.0, 0.135 mol), HCl (30 ml), and water (150 ml) was cooled to 0° C. and stirred for 1 hr. At the same temperature, an aqueous solution (75 ml) of sodium nitrite (11.2 g, 0.162 mol) was added and then stirred for 1 hr. An aqueous solution (75 ml) of potassium iodide (44.8 g, 0.270 mol) was dropwise added, with care not to increase the temperature of the reaction solution above 5° C. Stirring was continued for 5 hrs at room temperature, and after completion of the reaction, the reaction mixture was washed with an aqueous sodium thiosulfate solution and extracted with ethyl acetate and water. The organic layer was separated and concentrated in a vacuum. Purification through column chromatography gave <Intermediate 5-a> (22.6 g, 56.5%).

Synthesis Example 5-(2)

Synthesis of Intermediate 5-b

Intermediate 5-b was synthesized as illustrated in the following Reaction Scheme 35:

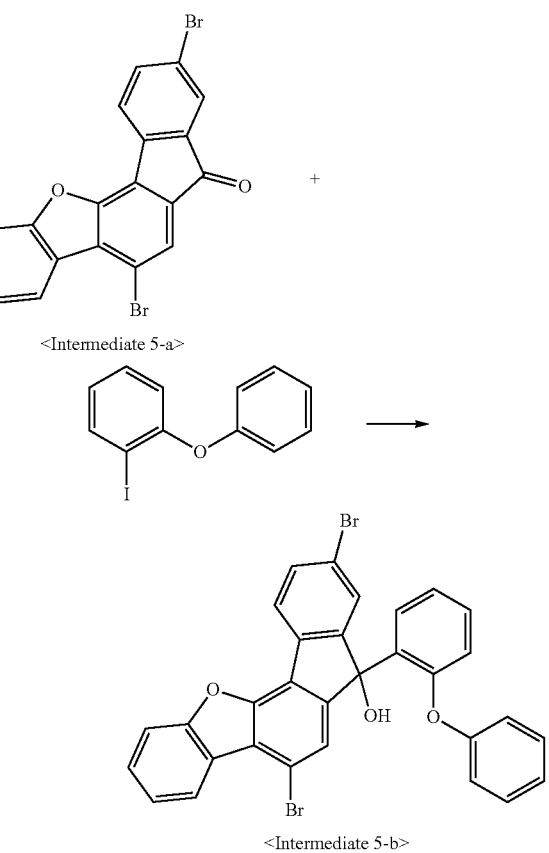

The same procedure as in Synthesis Example 1-(5), with the exception that <Intermediate 5-a> was used instead of 2-bromobiphenyl, was conducted to synthesize <Intermediate 5-b> (19.6 g, 70.4%).

Synthesis Example 5-(3)

Synthesis of Compound 49

Compound 49 was synthesized as illustrated in the following Reaction Scheme 36:

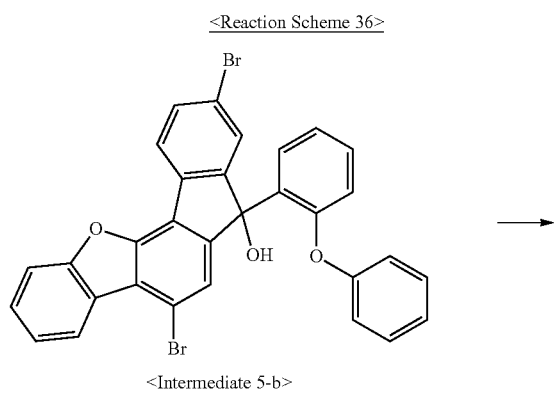

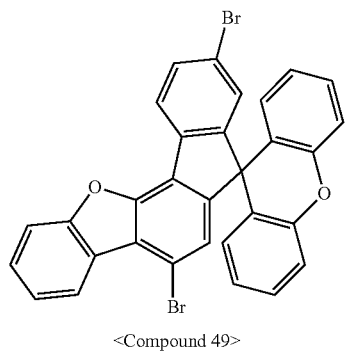

<Compound 49>

The same procedure as in Synthesis Example 1-(6), with the exception that <Intermediate 5-b> was used instead of <Intermediate 1-e>, was conducted to synthesize <Compound 49> (14.2 g, 74.7%).

Synthesis Example 5-(4)

Synthesis of Compound of Chemical Formula 5

The compound of Chemical Formula 37 was synthesized as illustrated in the following Reaction Scheme 37:

<Reaction Scheme 37>

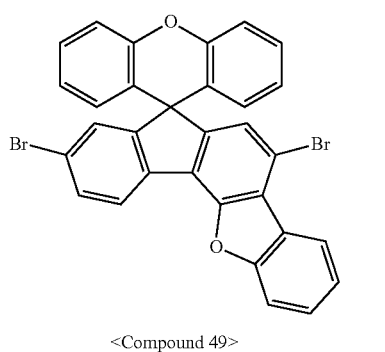

<Compound 49>

+

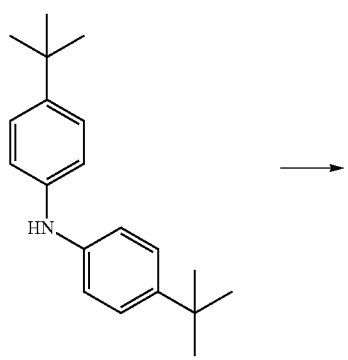

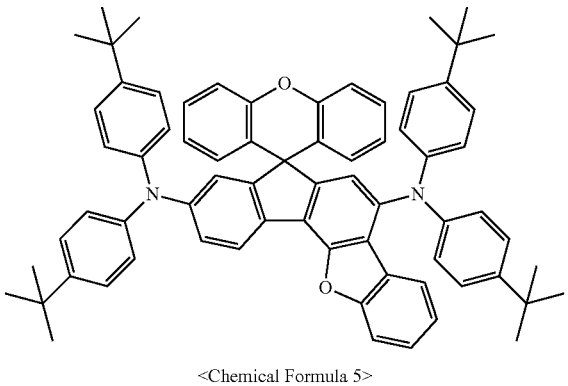

<Chemical Formula 5>

The same procedure as in Synthesis Example 1-(7), with the exception that <Compound 49> was used instead of <Compound 1, was conducted to synthesize the compound of <Chemical Formula 5> (2.4 g, 28%).

MS (MALDI-TOF): m/z 980.5 [M⁺]

Synthesis Example 6

Synthesis of Compound 37

Synthesis Example 6-(1)

Synthesis of Intermediate 6-a

Intermediate 6-a was synthesized as illustrated in the following Reaction Scheme 38:

<Reaction Scheme 38>

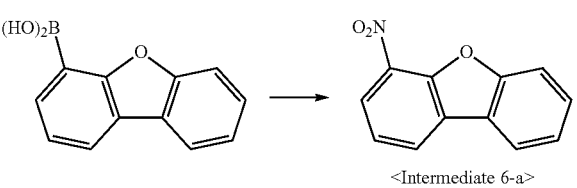

<Intermediate 6-a>

In a 2-L round-bottom flask reactor, 4-dibenzoboronic acid (85.0 g, 0.401 mol), bismuth (III) nitrate pentahydrate (99.2 g, 0.200 mol), and toluene (400 ml) were stirred together at 70° C. for 3 hrs under a nitrogen atmosphere. After completion of the reaction, the reaction mixture was cooled to room temperature, and the precipitates thus formed were filtered and washed with toluene to afford <Intermediate 6-a> (61.5 g, 72%).

Synthesis Example 6-(2)

Synthesis of Intermediate 6-b

Intermediate 6-b was synthesized as illustrated in the following Reaction Scheme 39:

<Reaction Scheme 39>

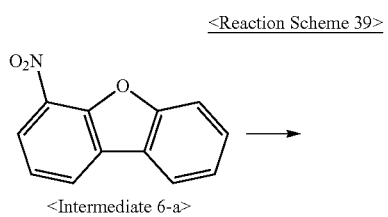

<Intermediate 6-a>

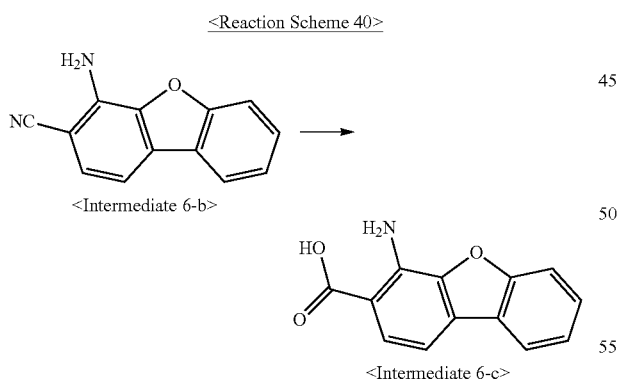

In a 2-L round-bottom flask reactor, ethylcyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. <Intermediate 6-a> (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded <Intermediate 6-b> (20.0 g, 16%).

Synthesis Example 6-(3)

Synthesis of Intermediate 6-c

Intermediate 6-c was synthesized as illustrated in the following Reaction Scheme 40:

<Reaction Scheme 40>

In a 2-L round-bottom flask reactor, <Intermediate 6-b> (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford <intermediate 6-c> (17.0 g, 88.5%).

Synthesis Example 6-(4)

Synthesis of Intermediate 6-d

Intermediate 6-d was synthesized as illustrated in the following Reaction Scheme 41:

<Reaction Scheme 41>

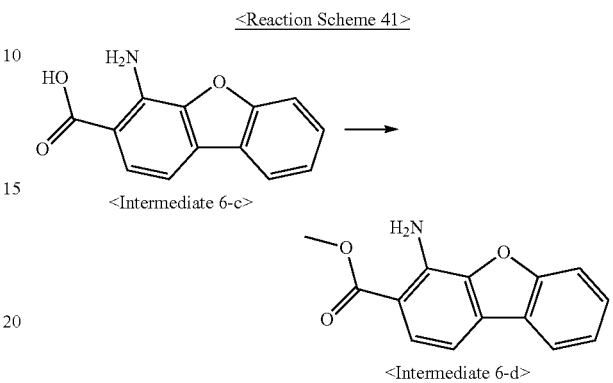

In a 2-L round-bottom flask reactor, <Intermediate 6-c> (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford <Intermediate 6-d> (14.0 77.6%).

Synthesis Example 6-(5)

Synthesis of Intermediate 6-e

Intermediate 6-e was synthesized as illustrated in the following Reaction Scheme 42:

<Reaction Scheme 42>

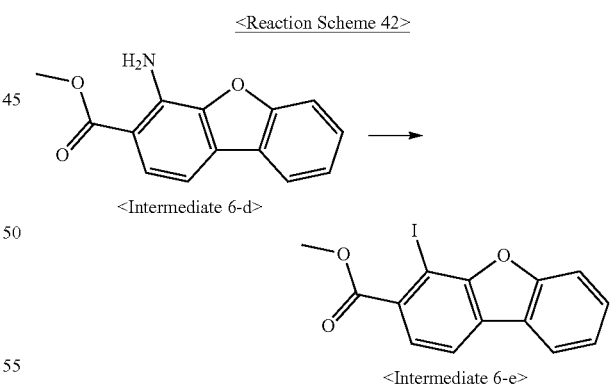

The same procedure as in Synthesis Example 5-(1), with the exception of using <Intermediate 6-d> instead of 2-phenoxyaniline, was conducted to synthesize <Intermediate 6-e> (9.1 g, 48%).

Synthesis Example 6-(6)

Synthesis of Intermediate 6-f

Intermediate 6-f was synthesized as illustrated in the following Reaction Scheme 43:

83

<Reaction Scheme 43>

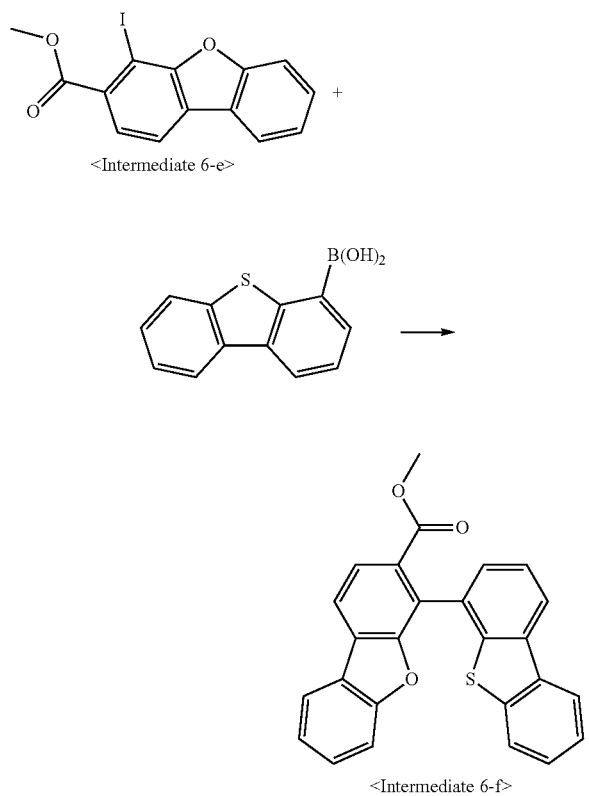

<Intermediate 6-f>

The same procedure as in Synthesis Example 1-(1), with the exception that <Intermediate 6-e> and 4-dibenzothiophene boronic acid were used instead of methyl 5-bromo-2-iodobenzoate and 4-dibenzofuran boronic acid, respective, was conducted to synthesize <Intermediate 6-f> (20.2 g, 84.3%).

Synthesis Example 6-(7)

Synthesis of Intermediate 6-g

Intermediate 6-g was synthesized as illustrated in the following Reaction Scheme 44:

<Reaction Scheme 44>

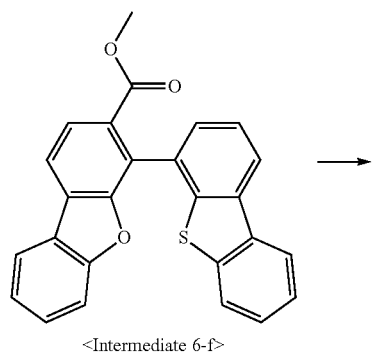

<Intermediate 6-f>

84

-continued

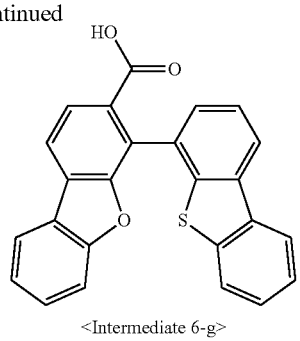

<Intermediate 6-g>

The same procedure as in Synthesis Example 1-(2), with the exception of using <Intermediate 6-f> instead of <Intermediate 1-a>, was conducted to synthesize <Intermediate 6-g> (16.5 g, 84.6%).

Synthesis Example 6-(8)

Synthesis of Intermediate 6-h

Intermediate 6-h was synthesized as illustrated in the following Reaction Scheme 45:

<Reaction Scheme 45>

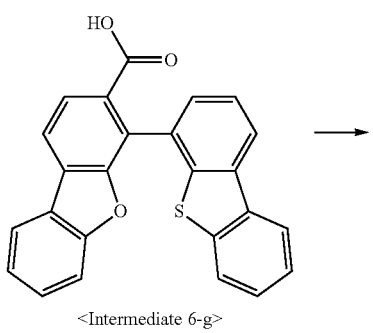

<Intermediate 6-g>

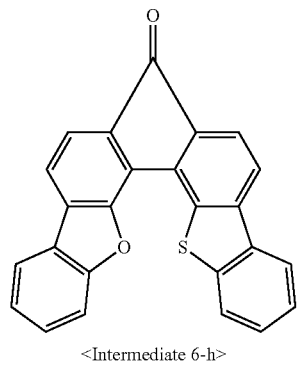

<Intermediate 6-h>

The same procedure as in Synthesis Example 1-(3), with the exception of using <Intermediate 6-g> instead of <Intermediate 1-b>, was conducted to synthesize <Intermediate 6-h> (12.4 g, 78.7%).

Synthesis Example 6-(9)

Synthesis of Intermediate 6-i

Intermediate 6-i was synthesized as illustrated in the following Reaction Scheme 46:

<Reaction Scheme 46>

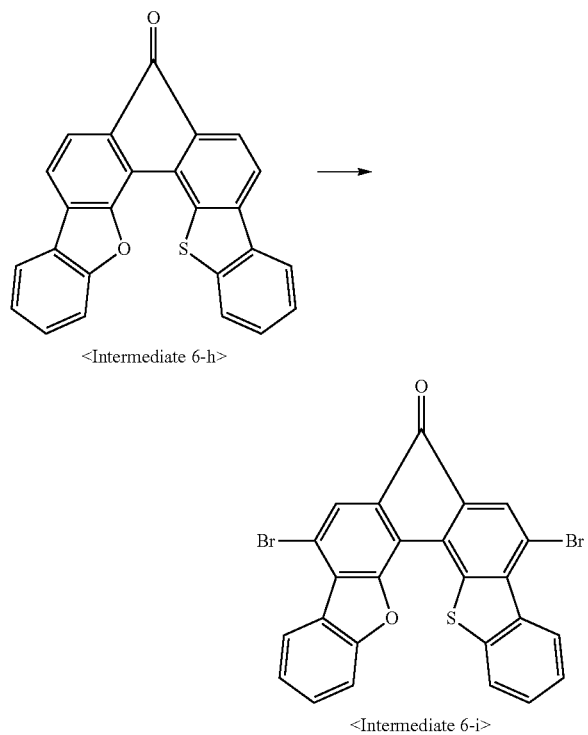

<Intermediate 6-h>

The same procedure as in Synthesis Example 1-(4), with the exception of using <Intermediate 6-h> instead of <Intermediate 1-c>, was conducted to synthesize <Intermediate 6-i> (3 g, 62.5%).

Synthesis Example 6-(10)

Synthesis of Intermediate 6-j

Intermediate 6-j was synthesized as illustrated in the following Reaction Scheme 47:

<Reaction Scheme 47>

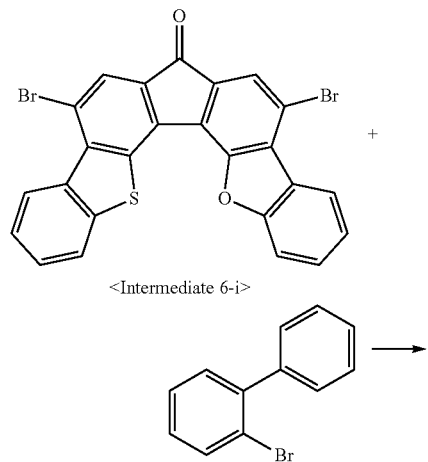

<Intermediate 6-i>

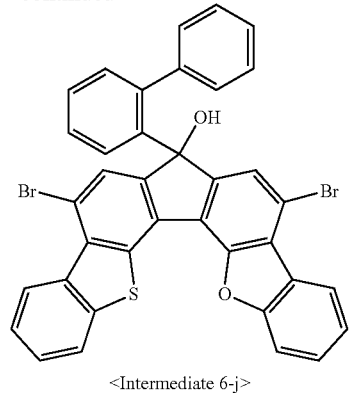

<Intermediate 6-j>

The same procedure as in Synthesis Example 1-(5), with the exception of using <Intermediate 6-i> instead of <Intermediate 1-d>, was conducted to synthesize <Intermediate 6-j> (10.2 g, 72.0%).

Synthesis Example 6-(11)

Synthesis of Compound 37

Compound 37 was synthesized as illustrated in the following Reaction Scheme 48:

<Reaction Scheme 48>

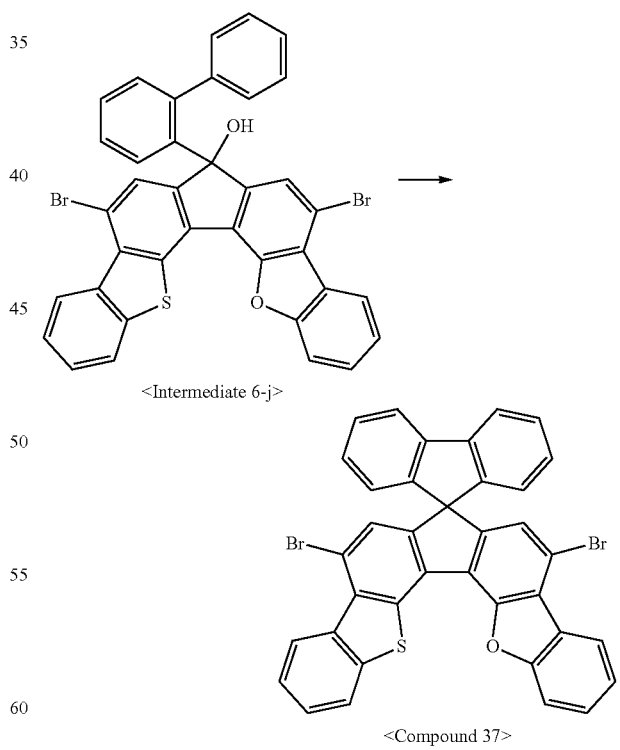

<Intermediate 6-j>

<Compound 37>

The same procedure as in Synthesis Example 1-(6), with the exception of using <Intermediate 6-j> instead of <Intermediate 1-e>, was conducted to synthesize Compound 37 (8.7 g, 87.6%).

87

Synthesis Example 6-(12)

Synthesis of Compound of Chemical Formula 6

The compound of Chemical Formula 6 was synthesized as illustrated in the following Reaction Scheme 49:

<Reaction Scheme 49>

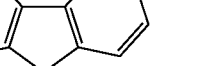

<Compound 37>

<Intermediate 4-c>

<Chemical Formula 6>

The same procedure as in Synthesis Example 1-(7), with the exception that Compound 37 and <Intermediate 4-c> were used instead of Compound 1 and bis(4-tert-butylphenyl)amine, was conducted to synthesize the compound of Chemical Formula 6 (2.8 g, 33.8%).

MS (MALDI-TOF): m/z 1110.5 [M$^+$]

88

Synthesis Example 7

Synthesis of Compound 58

Synthesis Example 7-(1)

Synthesis of Intermediate 7-a

Intermediate 7-a was synthesized as illustrated in the following Reaction Scheme 50:

<Reaction Scheme 50>

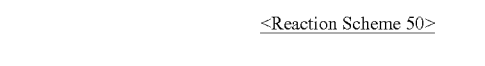

<Intermediate 7-a>

In a 2-L round-bottom flask reactor, 1-hydroxy 2-naphthoic acid (50 g, 266 mmol), methanol (1000 ml), and sulfuric acid (100 ml) were stirred together for 100 hrs under reflux. The completion of the reaction was confirmed by TLC before the reaction mixture was cooled to room temperature. The mixture was concentrated in a vacuum and extracted with dichloromethane and water. The organic layer was isolated, dried over magnesium sulfate, and filtered. The filtrate was concentrated in a vacuum and crystallized in an excess of heptane to afford <Intermediate 7-a> (39 g, 72.6%).

Synthesis Example 7-(2)

Synthesis of Intermediate 7-b

Intermediate 7-b was synthesized as illustrated in the following Reaction Scheme 51:

<Reaction Scheme 51>

<Intermediate 7-a>

<Intermediate 7-b>

In a 1-L round-bottom flask reactor, <Intermediate 7-a> (39.0 g, 193 mmol) was stirred together with acetic acid (390 ml) at room temperature. A dilution of acetic acid (80 ml) in bromine (11.8 ml, 231 mmol) was added dropwise thereto. The resulting reaction solution was stirred for 5 hrs at room temperature. After completion of the reaction, the precipitates thus formed were filtered and slurried in heptane to afford <Intermediate 7-b> (50 g, 90%).

Synthesis Example 7-(3)

Synthesis of Intermediate 7-c

Intermediate 7-c was synthesized as illustrated in the following Reaction Scheme 52:

<Reaction Scheme 52>

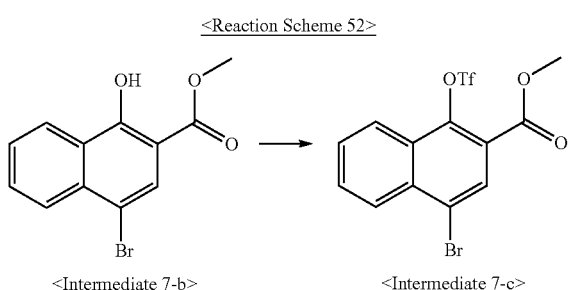 [SMILES: COC(=O)c1cc(Br)c2ccccc2c1O ; COC(=O)c1cc(Br)c2ccccc2c1OS(=O)(=O)C(F)(F)F]

<Intermediate 7-b>   <Intermediate 7-c>

In a 2-L round-bottom flask reactor, <Intermediate 7-b> (50 g, 178 mmol) was stirred together with dichloromethane. Under a nitrogen atmosphere, pyridine (28.1 g, 356 mol) was added and stirred at room temperature for 20 min. The resulting solution was cooled to 0° C. and then added with drops of trifluoromethanesulfonic anhydride (65.24 g, 231 mmol) under a nitrogen atmosphere. After 3 hrs of stirring, the completion of the reaction was confirmed by TLC. Water (20 ml) was added, and the mixture was stirred for 10 min. The reaction mixture was concentrated in a vacuum, followed by purification through column chromatography to afford <Intermediate 7-c> (45 g, 61%).

Synthesis Example 7-(4)

Synthesis of Intermediate 7-d

Intermediate was synthesized as illustrated in the following Reaction Scheme 53:

<Reaction Scheme 53>

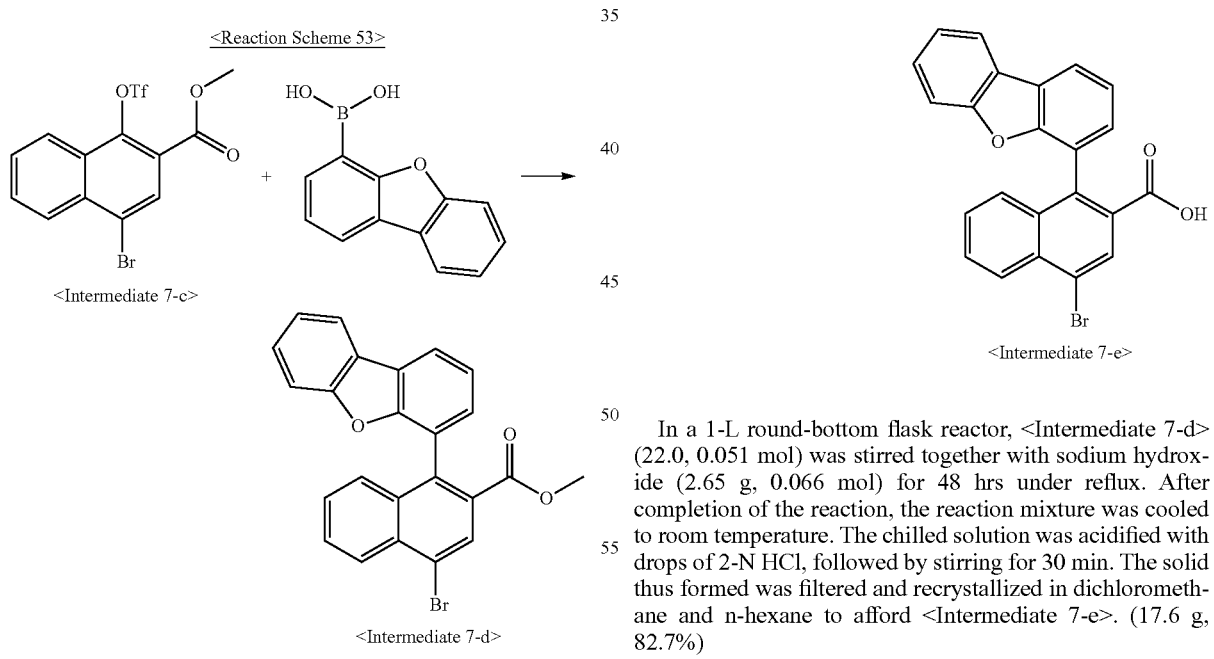

<Intermediate 7-c>

<Intermediate 7-d>

In a 1-L round-bottom flask reactor, a mixture of <Intermediate 7-c> (45.0 g, 0.109 mol), 4-dibenzofuran boronic acid (25.4 g, 0.120 mol), tetrakis (triphenylphosphine)palladium (2.5 g, 0.22 mmol), and potassium carbonate (30.1 g, 0.218 mol) was stirred together with toluene (300 mL), ethanol (130 mL) and water (90 mL) at 80° C. for 5 hrs. After completion of the reaction, the reaction mixture was cooled to room temperature and extracted with ethyl acetate. The organic layer was isolated and concentrated in a vacuum. Purification through column chromatography afforded Intermediate 7-d. (22.0 g, 46.1%)

Synthesis Example 7-(5)

Synthesis of Intermediate 7-e

Intermediate 7-e was synthesized as illustrated in the following Reaction Scheme 54:

<Reaction Scheme 54>

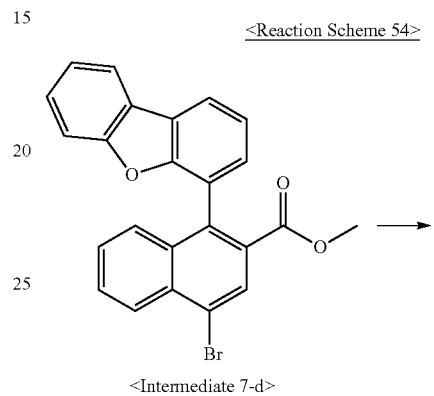

<Intermediate 7-d>

<Intermediate 7-e>

In a 1-L round-bottom flask reactor, <Intermediate 7-d> (22.0, 0.051 mol) was stirred together with sodium hydroxide (2.65 g, 0.066 mol) for 48 hrs under reflux. After completion of the reaction, the reaction mixture was cooled to room temperature. The chilled solution was acidified with drops of 2-N HCl, followed by stirring for 30 min. The solid thus formed was filtered and recrystallized in dichloromethane and n-hexane to afford <Intermediate 7-e>. (17.6 g, 82.7%)

Synthesis Example 7-(6)

Synthesis of Intermediate 7-f

Intermediate 7-f was synthesized as illustrated in the following Reaction Scheme 55:

<Reaction Scheme 55>

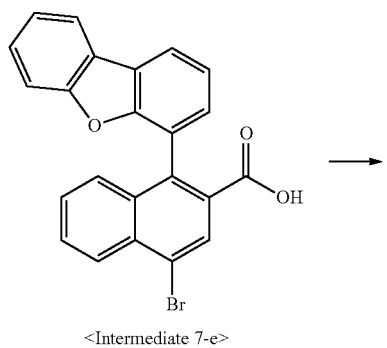

<Intermediate 7-e>

In a 500-mL round-bottom flask reactor, <Intermediate 7-e> (17.6 g, 0.042 mol) and methanesulfonic acid (170 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the precipitates thus formed were filtered and washed with water and methanol. They were dissolved in monochlorobenzene and filtered through a silica gel pad. The filtrate was concentrated by heating and recrystallized in acetone to afford <Intermediate 7-f>. (12 g, 71%)

Synthesis Example 7-(7)

Synthesis of Intermediate 7-g

Intermediate 7-g was synthesized as illustrated in the following Reaction Scheme 56:

<Reaction Scheme 56>

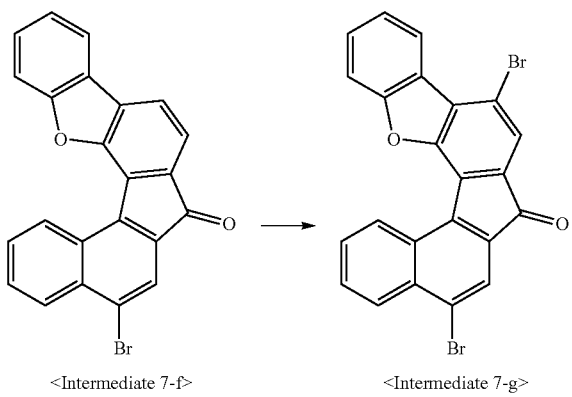

<Intermediate 7-f>   <Intermediate 7-g>

In a 1-L round-bottom flask reactor, <Intermediate 7-f> (12.0 g, 0.030 mol) and dichloromethane (360 ml) were stirred together at room temperature. A dilution of bromine (3.1 ml, 0.06 mol) in dichloromethane (40 ml) was dropwise added, followed by stirring at room temperature for 12 hrs. After completion of the reaction, methanol (100 ml) was added to induce the formation of precipitates. They were then filtered and washed with methanol. Recrystallization in 1,2-dichlorobenzene and acetone afforded <Intermediate 7-g> (10.3 g, 71.7%).

Synthesis Example 7-(8)

Synthesis of Intermediate 7-h

Intermediate 7-h was synthesized as illustrated in the following Reaction Scheme 57:

<Reaction Scheme 57>

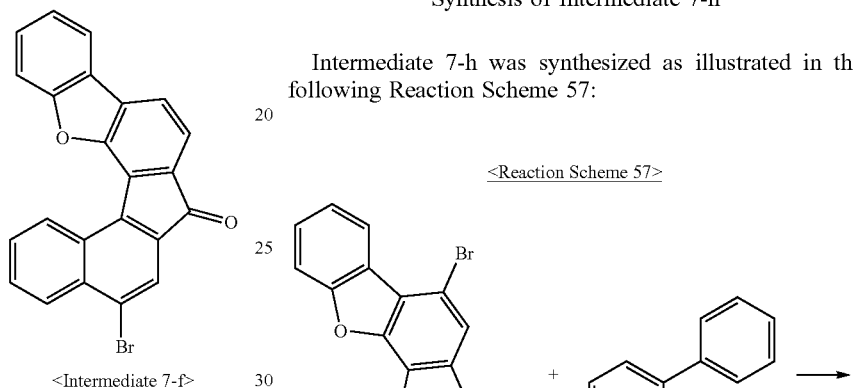

<Intermediate 7-g>

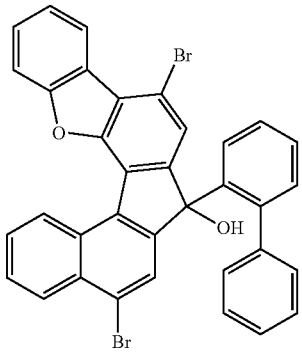

<Intermediate 7-h>

The same procedure as in Synthesis Example 1-(5), with the exception of using <Intermediate 7-g> instead of <Intermediate 1-d>, was conducted to synthesize <Intermediate 7-h> (10.0 g, 73.4%).

Synthesis Example 7-(9)

Synthesis of Compound 58

Compound 58 was synthesized as illustrated in the following Reaction Scheme 58:

<Reaction Scheme 58>

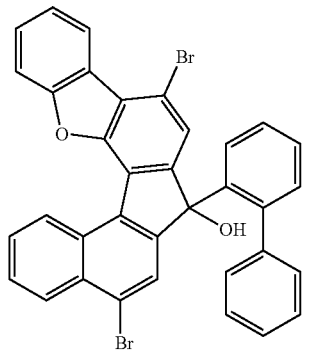

<Intermediate 7-h>

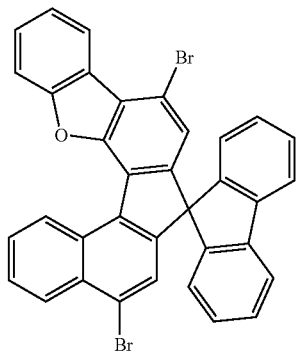

<Compound 58>

The same procedure as in Synthesis Example 1-(6), with the exception of using <Intermediate 7-h> instead of <Intermediate 1-e>, was conducted to synthesize Compound 58. (6.3 g, 64.8%)

Synthesis Example 7-(10)

Synthesis of Compound of Chemical Formula 7

The compound of Chemical Formula 7 was synthesized as illustrated in the following Reaction Scheme 59:

<Reaction Scheme 59>

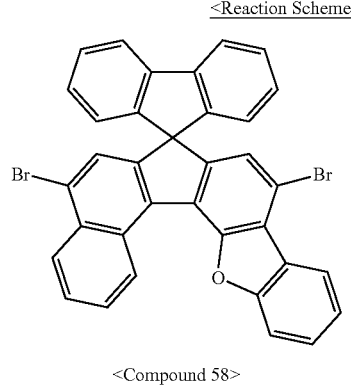

<Compound 58>

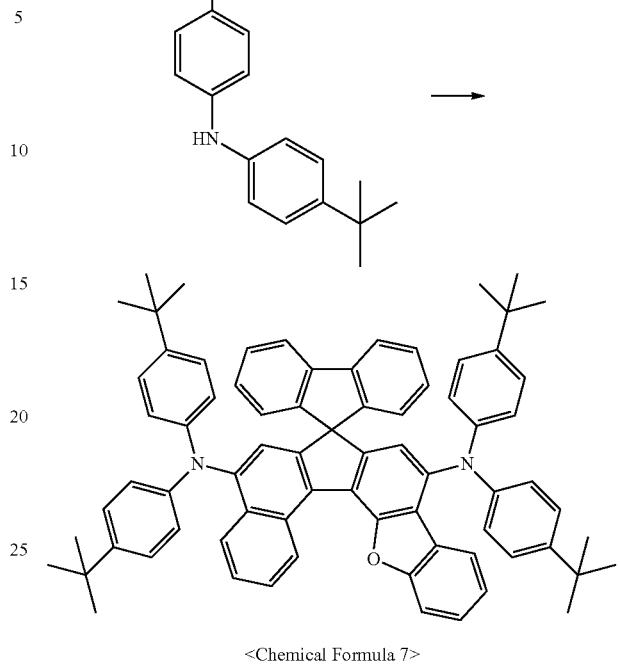

<Chemical Formula 7>

The same procedure as in Synthesis Example 1-(7), with the exception of using Compound 58 instead of Compound 1, was conducted to synthesize the compound of Chemical Formula 7. (3.0 g, 36.1%).

MS (MALDI-TOF): m/z 1014.5 [M$^+$]

Synthesis Example 8

Synthesis of Compound 59

Synthesis Example 8-(1)

Synthesis of Intermediate 8-a

Intermediate 8-a was synthesized as illustrated in the following Reaction Scheme 60:

<Reaction Scheme 60>

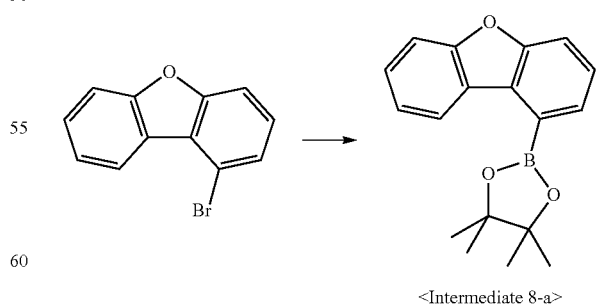

<Intermediate 8-a>

In a 500-mL round-bottom flask reactor, 1-bromodibenzofuran (20.0 g, 0.081 mmol), bis(pinacolato)diboron (26.7 g, 0.105 mol), [1,1'-bis(diphenylphosphino)ferrocene]dichloropalladium (1.3 g, 0.002 mol), potassium acetate (19.9 g, 0.202 mol), and 1,4-dioxane (200 ml) were stirred together for 10 hrs under reflux. After completion of the reaction, filtration was performed through a celite pad. The filtrate was concentrated in a vacuum, purified by column chromatography, and recrystallized in dichloromethane and heptane to afford <Intermediate 8-a> (17.0 g, 70%).

Synthesis Example 8-(2)

Synthesis of Intermediate 8-b

Intermediate 8-b was synthesized as illustrated in the following Reaction Scheme 61:

<Reaction Scheme 61>

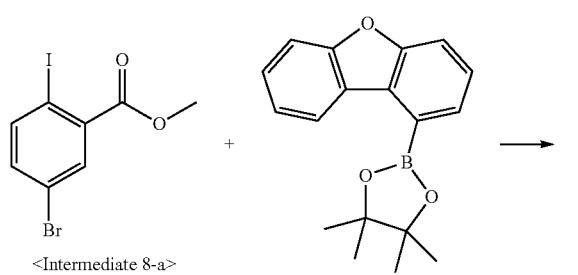

<Intermediate 8-b>

The same procedure as in Synthesis Example 1-(1), with the exception of using <Intermediate 8-a> instead of 4-dibenzobronic acid, was conducted to synthesize <Intermediate 8-b> (13.1 g, 68.9%).

Synthesis Example 8-(3)

Synthesis of Intermediate 8-c

Intermediate 8-c was synthesized as illustrated in the following Reaction Scheme 62:

<Reaction Scheme 62>

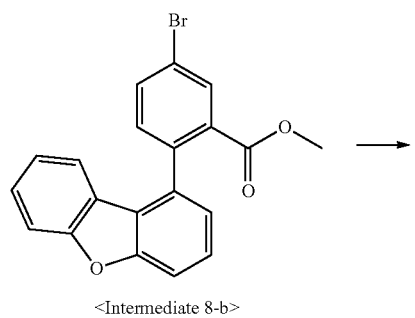

<Intermediate 8-b>

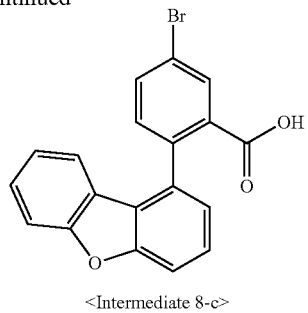

<Intermediate 8-c>

The same procedure as in Synthesis Example 1-(2), with the exception of using <Intermediate 8-b> instead of <Intermediate 1-a>, was conducted to synthesize <Intermediate 8-c> (11 g, 87%).

Synthesis Example 8-(4)

Synthesis of Intermediate 8-d

Intermediate 8-d was synthesized as illustrated in the following Reaction Scheme 63:

<Reaction Scheme 63>

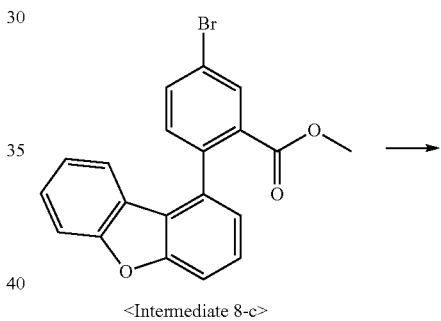

<Intermediate 8-c>

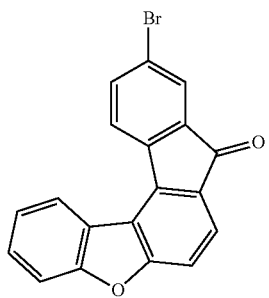

<Intermediate 8-d>

The same procedure as in Synthesis Example 1-(3), with the exception of using <Intermediate 8-c> instead of <Intermediate 1-b>, was conducted to synthesize <Intermediate 8-d> (9.0 g, 86%).

Synthesis Example 8-(5)

Synthesis of Intermediate 8-e

Intermediate 8-e was synthesized as illustrated in the following Reaction Scheme 64:

<Reaction Scheme 64>

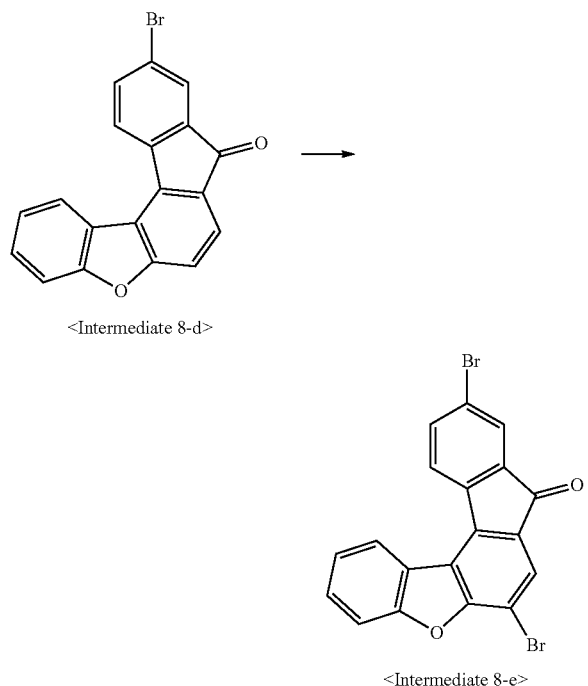

<Intermediate 8-d>

<Intermediate 8-e>

The same procedure as in Synthesis Example 1-(4), with the exception of using <Intermediate 8-d>, instead of <Intermediate 1-c>, was conducted to synthesize <Intermediate 8-e> (6.7 g, 60.7%).

Synthesis Example 8-(6)

Synthesis of Intermediate 8-f

Intermediate 8-f was synthesized as illustrated in the following Reaction Scheme 65:

<Reaction Scheme 65>

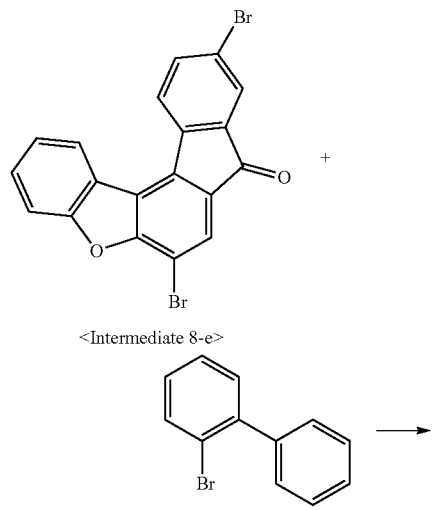

<Intermediate 8-e>

-continued

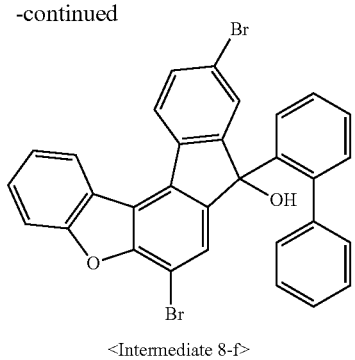

<Intermediate 8-f>

The same procedure as in Synthesis Example 1-(5), with the exception of using <Intermediate 8-e> instead of <Intermediate 1-d>, was conducted to synthesize <Intermediate 8-f> (5.2 g, 55%).

Synthesis Example 8-(7)

Synthesis of Compound 59

Compound 59 was synthesized as illustrated in the following Reaction Scheme 66:

<Reaction Scheme 66>

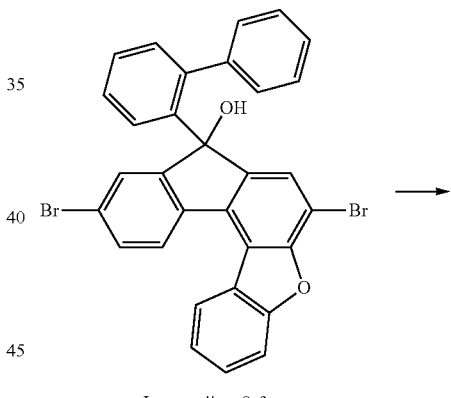

<Intermediate 8-f>

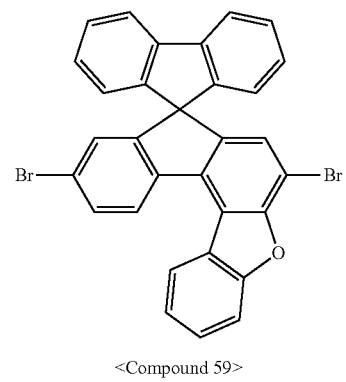

<Compound 59>

The same procedure as in Synthesis Example 1-(6), with the exception of using <Intermediate 8-f> instead of <Intermediate 1-e>, was conducted to synthesize Compound 59 (4.3 g, 85.3%).

Synthesis Example 8-(8)

Synthesis of Compound of Chemical Formula 8

The compound of Chemical Formula 8 was synthesized as illustrated in the following Reaction Scheme 67:

<Reaction Scheme 67>

<Compound 59>

<Chemical Formula 8>

The same procedure as in Synthesis Example 1-(7), with the exception of using Compound 59 instead of Compound 1, was conducted to synthesize the compound of Chemical Formula 8 (2.5 g, 34%).

MS (MALDI-TOF): m/z 964.5 [M+]

Synthesis Example 9

Synthesis of Compound 61

Synthesis Example 9-(1)

Synthesis of Intermediate 9-a

Intermediate 9-a was synthesized as illustrated in the following Reaction Scheme 68:

<Reaction Scheme 68>

<Intermediate 9-a>

In a 1-L round-bottom flask reactor, 2-iodonitrobenzene (15.0 g, 0.060 mol), 2-bromophenyl boronic acid (13.3 g, 0.066 mol), palladium acetate (0.67 g, 0.003 mol), potassium carbonate (16.6 g, 0.120 mol), and triphenylphosphine (2.37 g, 0.009 mol) were placed, followed by toluene (525 mL), ethanol (60 ml), and water (60 mL). The reaction mixture was heated to 100° C. and stirred for 18 hrs. After completion of the reaction, the reaction mixture was cooled to room temperature and extracted with ethyl acetate. The organic layer was isolated, concentrated in a vacuum, and purified through column chromatography to afford <Intermediate 9-a>. (14.0 g, 83.6%)

Synthesis Example 9-(2)

Synthesis of Intermediate 9-b

Intermediate 9-b was synthesized as illustrated in the following Reaction Scheme 69:

<Reaction Scheme 69>

<Intermediate 9-a>   <Intermediate 9-b>

In a 250-ml round-bottom flask, <Intermediate 9-a> (14.0 g, 0.050 mol), triphenylphosphine (33.01 g, 0.126 mol), and N,N-dimethyl acetamide (100 ml) were stirred together at 180° C. for 14 hrs. After completion of the reaction, the reaction mixture was cooled to room temperature and stirred together with water (200 ml). Extraction with ethyl acetate gave an organic layer which was then isolated, concentrated in a vacuum, and purified through a column to afford <Intermediate 9-b> (7.0 g, 56.5).

Synthesis Example 9-(3)

Synthesis of Intermediate 9-c

Intermediate 9-c was synthesized as illustrated in the following Reaction Scheme 70:

<Reaction Scheme 70>

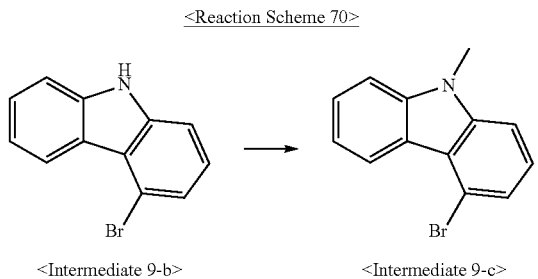

<Intermediate 9-b>          <Intermediate 9-c>

In a 250-ml round-bottom flask, <Intermediate 9-b> (7.0 g, 0.028 mol), tetrahydrofuran (140 ml), and sodium hydride (60%) (1.19 g, 0.029 mol) were stirred together for 30 min at room temperature and then at 0° C. Drops of iodomethane (3.5 ml, 0.057 mol) were added to the chilled solution, followed by stirring at room temperature for 18 hrs. After completion of the reaction, water (100 ml) was added, and extraction was conducted with ethyl acetate. The organic layer was isolated, dried over anhydrous magnesium sulfate, filtered, and concentrated in vacuum. Purification through column chromatography afforded <Intermediate 9-c> (7.2 g, 92.7%).

Synthesis Example 9-(4)

Synthesis of Intermediate 9-d

Intermediate 9-d was synthesized as illustrated in the following Reaction Scheme 71:

<Reaction Scheme 71>

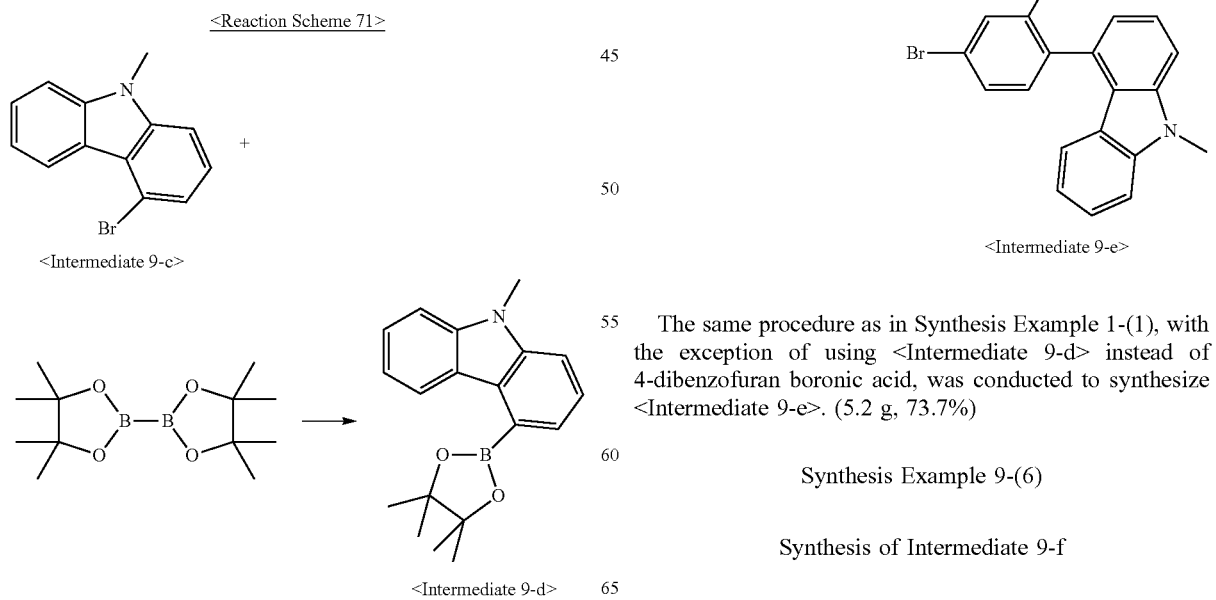

The same procedure as in Synthesis Example 8-(1), with the exception of using <Intermediate 9-c> instead of 1-bromodibenzofuran, was conducted to synthesize <Intermediate 9-d> (6.1 g, 71.7%).

Synthesis Example 9-(5)

Synthesis of Intermediate 9-e

Intermediate 9-e was synthesized as illustrated in the following Reaction Scheme 72:

<Reaction Scheme 72>

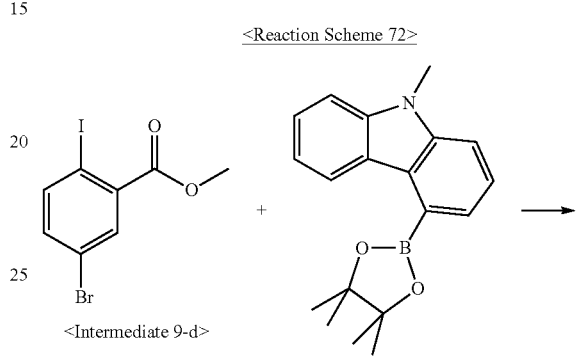

<Intermediate 9-d>

<Intermediate 9-e>

The same procedure as in Synthesis Example 1-(1), with the exception of using <Intermediate 9-d> instead of 4-dibenzofuran boronic acid, was conducted to synthesize <Intermediate 9-e>. (5.2 g, 73.7%)

Synthesis Example 9-(6)

Synthesis of Intermediate 9-f

Intermediate 9-f was synthesized as illustrated in the following Reaction Scheme 73:

<Reaction Scheme 73>

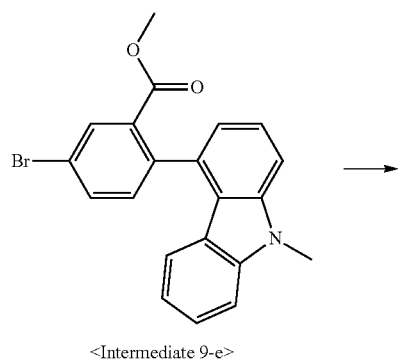

<Intermediate 9-e>

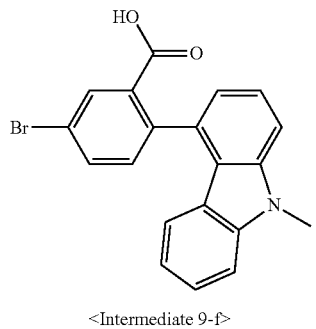

<Intermediate 9-f>

The same procedure as in Synthesis Example 1-(2), with the exception of using <Intermediate 9-e> instead of <Intermediate 1-a>, was conducted to synthesize <Intermediate 9-f> (8.2 g, 85%).

Synthesis Example 9-(7)

Synthesis of Intermediate 9-g

Intermediate 9-g was synthesized as illustrated in the following Reaction Scheme 74:

<Reaction Scheme 74>

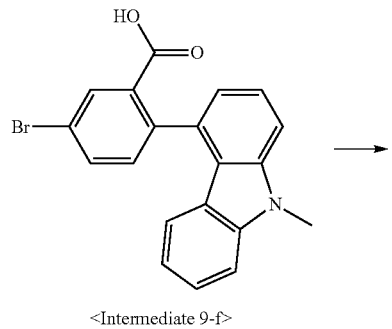

<Intermediate 9-f>

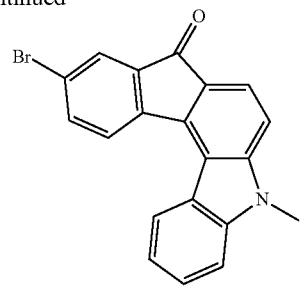

<Intermediate 9-g>

The same procedure as in Synthesis Example 1-(3), with the exception of using <Intermediate 9-f> instead of <Intermediate 1-b>, was conducted to synthesize <Intermediate 9-g> (6.7 g, 85.8%).

Synthesis Example 9-(8)

Synthesis of Intermediate 9-h

Intermediate 9-h was synthesized as illustrated in the following Reaction Scheme 75:

<Reaction Scheme 75>

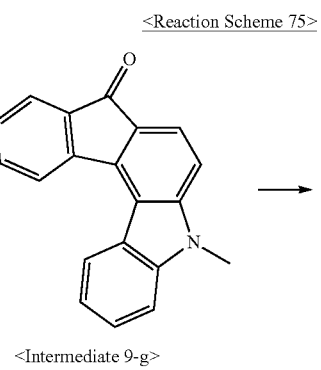

<Intermediate 9-g>

<Intermediate 9-h>

The same procedure as in Synthesis Example 1-(4), with the exception of using <Intermediate 9-g> instead of <Intermediate 1-c>, was conducted to synthesize <Intermediate 9-h> (4.3 g, 52.7%).

Synthesis Example 9-(9)

Synthesis of Intermediate 9-i

Intermediate 9-i was synthesized as illustrated in the following Reaction Scheme 76:

<Reaction Scheme 76>

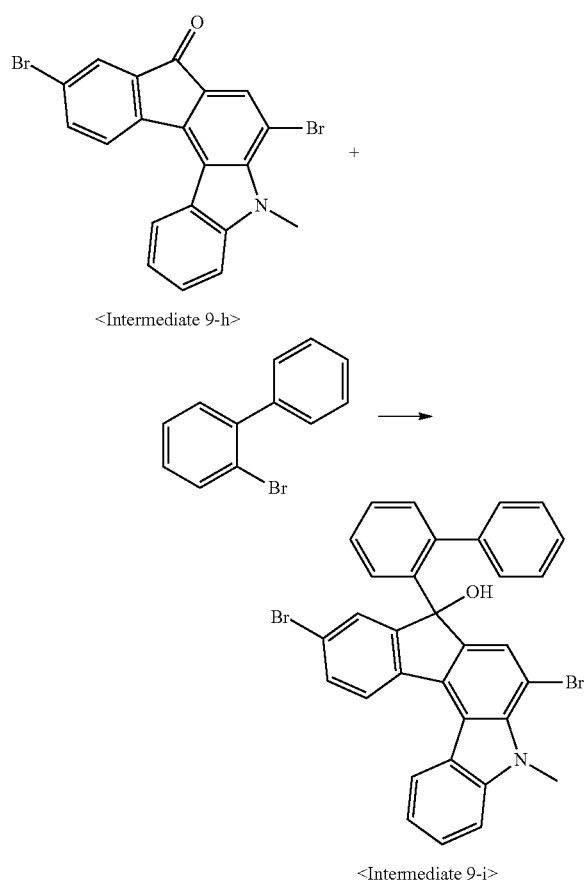

<Intermediate 9-h>

<Intermediate 9-i>

The same procedure as in Synthesis Example 1-(5), with the exception of using <Intermediate 9-h> instead of <Intermediate 1-d>, was conducted to synthesize <Intermediate 9-i> (4.0 g, 68.9%).

Synthesis Example 9-(10)

Synthesis of Compound 61

Compound 61 was synthesized as illustrated in the following Reaction Scheme 77:

<Reaction Scheme 77>

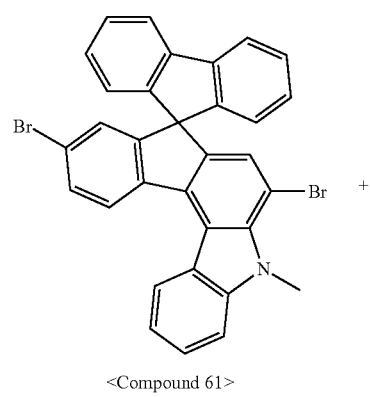

<Intermediate 9-i>

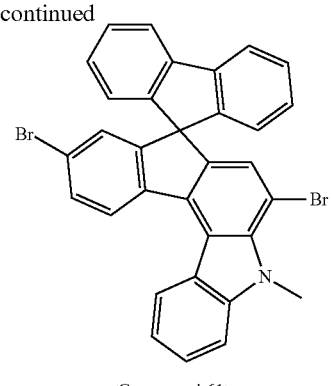

<Compound 61>

The same procedure as in Synthesis Example 1-(6), with the exception of using <Intermediate 9-i> instead of <Intermediate 1-e>, was conducted to synthesize Compound 61 (3.2 g, 82.5%).

Synthesis Example 9-(11)

Synthesis of Compound of Chemical Formula 9

The compound of Chemical Formula 9 was synthesized as illustrated in the following Reaction Scheme 78:

<Reaction Scheme 78>

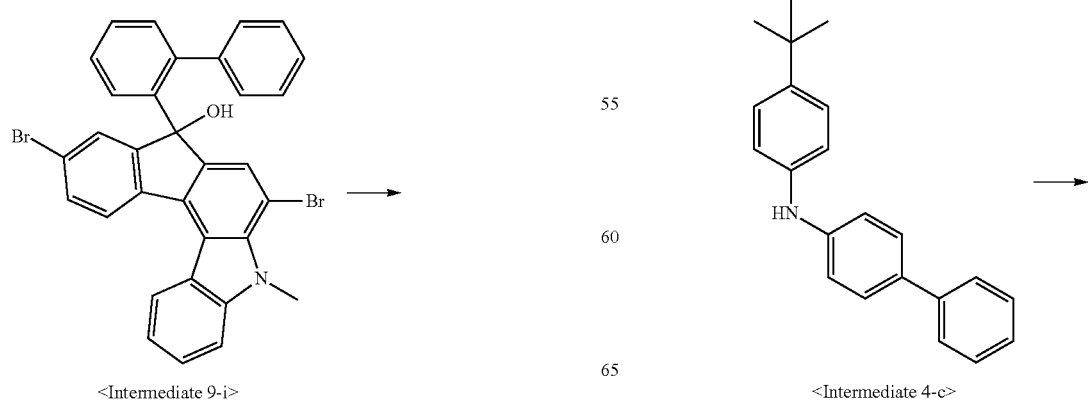

<Compound 61>  <Intermediate 4-c>

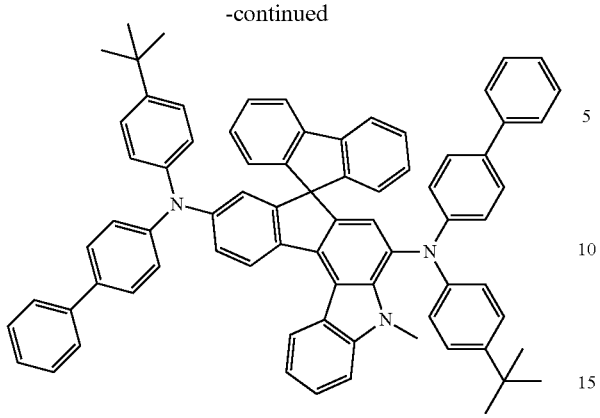

<Chemical Formula 9>

The same procedure as in Synthesis Example 1-(7), with the exception that Compound 61 and <Intermediate 4-c> were respectively used instead of Compound 1 and bis(4-tert-butylphenyl)amine, was conducted to synthesize the compound of Chemical Formula 9 (2.3 g, 40.7%).

MS (MALDI-TOF): m/z 1017.5 [M$^+$]

Synthesis Example 10

Synthesis of Compound 64

Synthesis Example 10-(1)

Synthesis of Intermediate 10-a

Intermediate 10-a was synthesized illustrated in the following Reaction Scheme 79:

<Reaction Scheme 79>

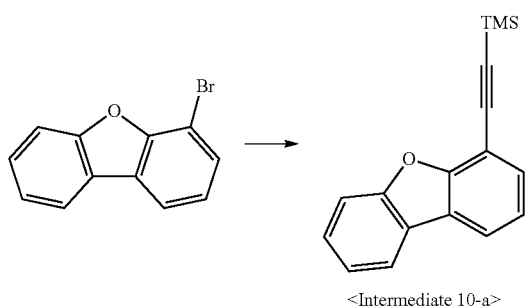

<Intermediate 10-a>

In a 2-L round bottom flask, 4-bromodibenzofuran (100.0 g, 0.405 mol), ethynyl trimethylsilane (47.7 g, 0.486 mol), [1,1'-bis(diphenylphosphino)ferrocene]dichloropalladium (9.92 g, 0.012 mol), copper iodide (2.31 g, 0.012 mol), triphenylphosphine (10.6 g, 0.040 mol), and triethylamine (700 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 10-a> (130 g, 84%)

Synthesis Example 10-(2)

Synthesis of Intermediate 10-b

Intermediate 10-b was synthesized as illustrated in the following Reaction Scheme 80:

<Reaction Scheme 80>

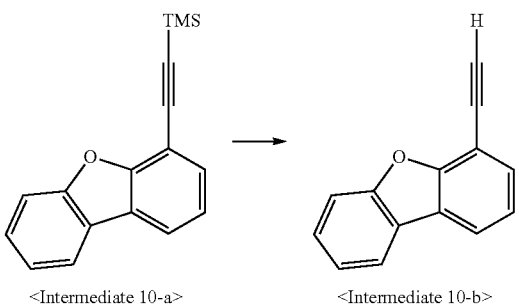

<Intermediate 10-a>   <Intermediate 10-b>

In a 2-L round-bottom flask reactor, <Intermediate 10-a> (130 g, 0.492 mol), potassium carbonate (101.9 g, 0.738 mol), methanol (650 ml), and tetrahydrofuran (650 ml) were stirred together for 2 hrs at room temperature. After completion of the reaction, heptane (500 ml) was added to terminate the reaction. The reaction mixture was filtered and the filtrate was extracted with ethyl acetate and water. The organic layer thus formed was isolated and dried over magnesium sulfate. Filtration and vacuum concentration afforded <Intermediate 10-b> as an oil (82 g, 84%).

Synthesis Example 10-(3)

Synthesis of Intermediate 10-c

Intermediate 10-c was synthesized as illustrated in the following Reaction Scheme 81:

<Reaction Scheme 81>

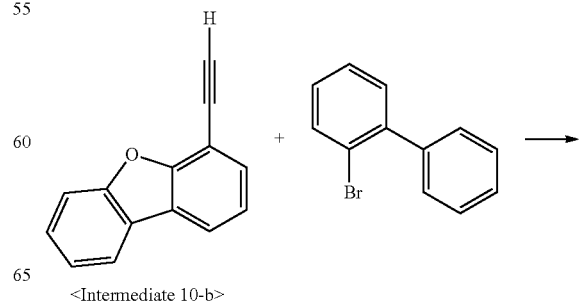

<Intermediate 10-b>

-continued

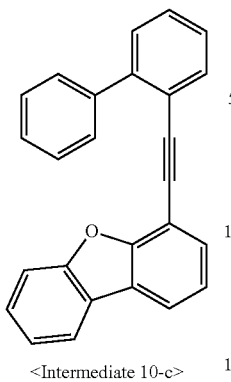

<Intermediate 10-c>

In a 2-L round-bottom flask reactor, 2-bromobiphenyl (66.0 g, 0.283 mol), <Intermediate 10-b> (65.3 g, 0.340 mol), [1,1'-bis(diphenylphosphino)ferrocene]dichloropalladium (6.94 g, 0.008 mol), copper iodide (1.62 g, 0.008 mol), triphenylphosphine (7.4 g, 0.028 mol), and triethylamine (500 ml) were stirred for 5 hrs under reflux in a nitrogen atmosphere. After completion of the reaction, the reaction mixture was cooled to room temperature and added with heptane (400 ml) to terminate the reaction. Filtration was conducted through a silica gel pad topped with celite. The filtrate was concentrated in a vacuum to afford <Intermediate 10-c> (80 g, 82%).

Synthesis Example 10-(4)

Synthesis of Intermediate 10-d

Intermediate 10-d was synthesized as illustrated in the following Reaction Scheme 82:

<Reaction Scheme 82>

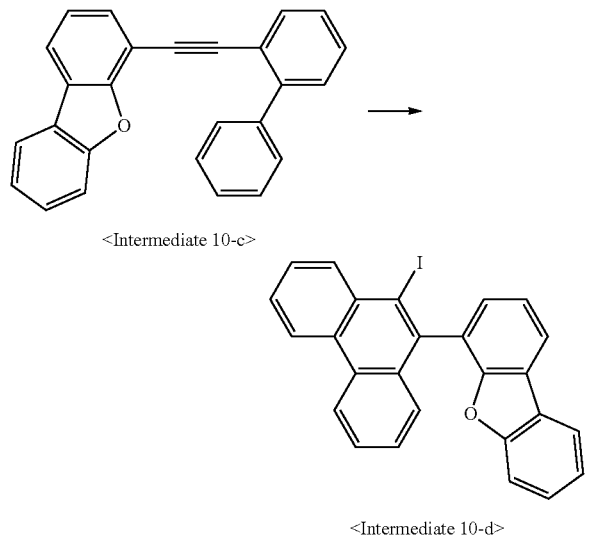

<Intermediate 10-d>

In a 2-L round-bottom flask reactor, a solution of <Intermediate 10-c> (80.0 g, 0.232 mol) in dichloromethane (960 ml) was cooled to −78° C. under nitrogen atmosphere. Iodine monochloride (278.4 ml, 0.279 mol) was dropwise added to the chilled solution, which was then stirred at room temperature for 12 hrs. After completion of the reaction, the reaction mixture was stirred together with an aqueous saturated sodium thiosulfate solution. Following extraction with dichloromethane and water, the organic layer was isolated, concentrated in a vacuum, and washed with methanol to afford <Intermediate 10-d> as a crystal (67 g, 61.3%).

Synthesis Example 10-(5)

Synthesis of Intermediate 10-e

Intermediate 10-e was synthesized as illustrated in the following Reaction Scheme 83:

<Reaction Scheme 83>

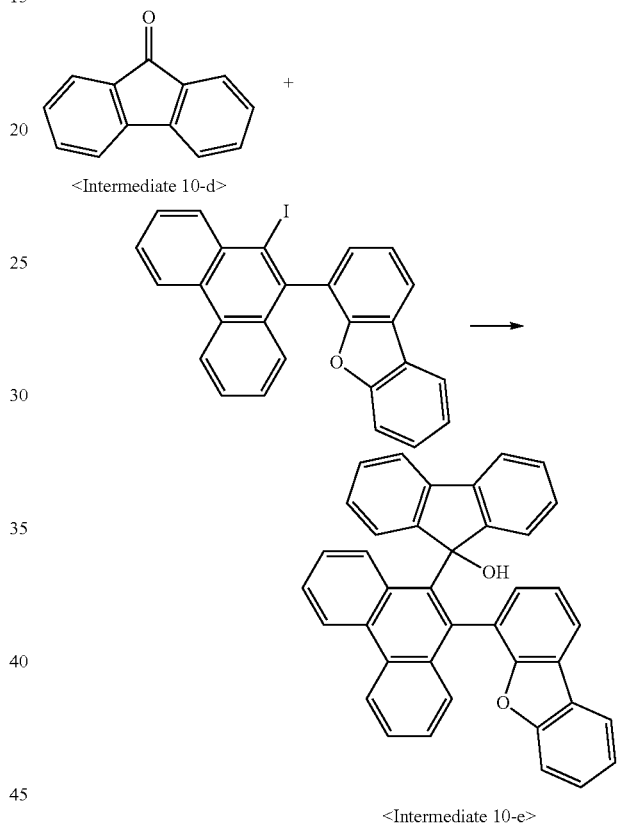

<Intermediate 10-e>

In a 500-mL round-bottom flask reactor, a solution of <Intermediate 10-d> (54.8 g, 0.117 mol) in tetrahydrofuran (150 ml) was cooled to −78° C. under a nitrogen atmosphere. At the same temperature, 1.6 M n-butyl lithium (62.4 ml, 0.1 mol) was dropwise added to the chilled solution and stirred for 1 hr. Then, a solution of 9-fluorenone (15.0 g, 0.083 mol) in tetrahydrofuran (50 ml) was dropwise added before stirring at room temperature for 8 hrs. After completion of the reaction, extraction was performed with ethyl acetate and water. The organic layer thus formed was isolated and dried over magnesium sulfate. Vacuum concentration subsequent to filtration afforded <Intermediate 10-e> as an oil (33.2 g, 76%).

Synthesis Example 10-(6)

Synthesis of Intermediate 10-f

Intermediate 10-f was synthesized as illustrated in the following Reaction Scheme 84:

<Reaction Scheme 84>

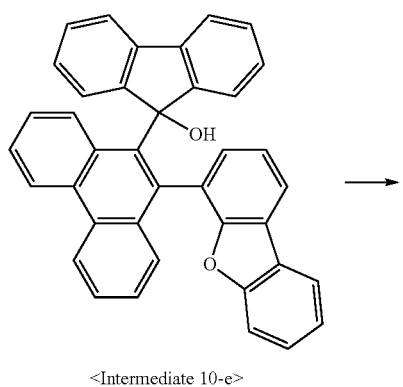

<Intermediate 10-e>

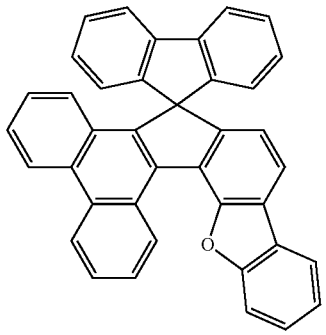

<Intermediate 10-f>

In a 1-L round-bottom flask reactor, <Intermediate 10-e> (33.3 g, 0.063 mol), acetic acid (330 ml), and sulfuric acid (3 ml) were stirred together for 3 hrs under reflux. After the completion of the reaction was confirmed using thin-layer chromatography, the reaction mixture was cooled to room temperature. The precipitates thus formed were filtered and washed with $H_2O$ and methanol to afford <Intermediate 10-f> (28.6 g, 88>.

Synthesis Example 10-(7)

Synthesis of Compound 64

Compound 64 was synthesized as illustrated in the following Reaction Scheme 85:

<Reaction Scheme 85>

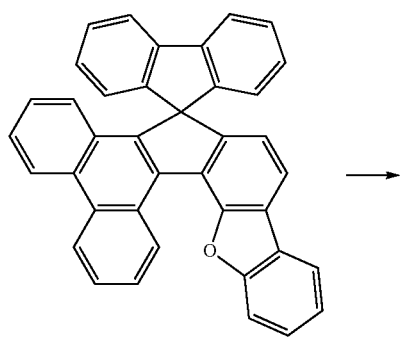

<Intermediate 10-f>

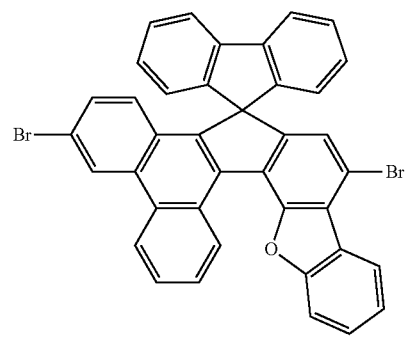

<Compound 64>

In a 1-L round-bottom flask reactor, a solution of <Intermediate 10-f> (20.0 g, 0.039 mol) in dichloromethane (200 ml) was added with drops of a dilution of bromine (6 ml, 0.118 mol) in dichloromethane (40 ml) while stirring. After completion of the reaction for 12 hrs of stirring at room temperature, the addition of methanol (100 ml) produced precipitates which were then washed with methanol. Recrystallization in 1,2-dichlorobenzene and acetone afforded Compound 64 (16 g, 60%).

Synthesis Example 10-(8)

Synthesis of Compound of Chemical Formula 10

The compound of Chemical Formula 10 was synthesized as illustrated in the following Reaction Scheme 86:

<Reaction Scheme 86>

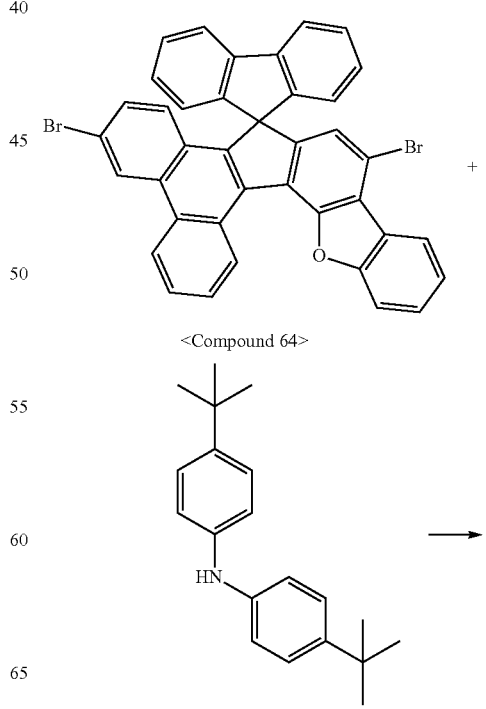

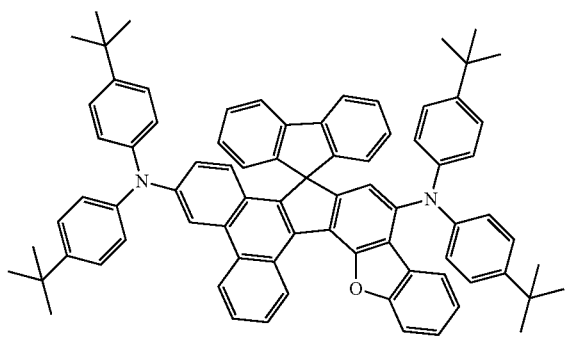

<Chemical Formula 10>

The same procedure as in Synthesis Example 1-(7), with the exception of using Compound 64 instead of Compound 1, was conducted to synthesize the compound of Chemical Formula 10 (2.5 g, 31%).

MS (MALDI-TOF): m/z 1064.5 [M$^+$]

Synthesis Example 11

Synthesis of Compound 73

Synthesis Example 11-(1)

Synthesis of Intermediate 11-a

Intermediate 11-a was synthesized as illustrated in the following Reaction Scheme 87:

<Reaction Scheme 87>

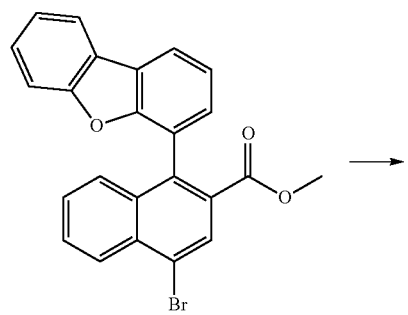

<Intermediate 7-d>

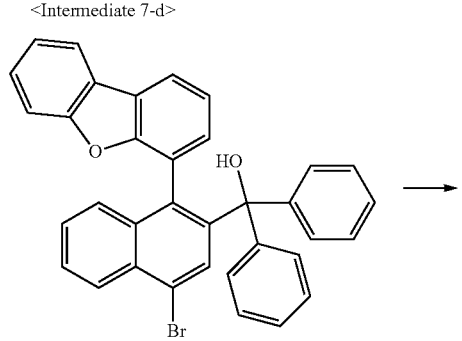

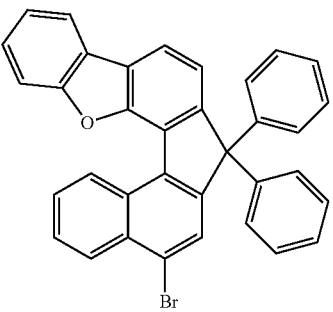

<Intermediate 11-a>

In a 500-mL round-bottom flask reactor, a mixture of bromobenzene (25.46 g, 0.163 mol) and tetrahydrofuran (170 ml) was cooled to −78° C. under a nitrogen atmosphere. N-butyl lithium (1.6 M) (95.6 ml, 0.153 mol) was dropwise added to the chilled solution, which was then stirred at the same temperature for 1 hr. <Intermediate 7-d> (22.0 g, 0.051 mol) was added, followed by stirring at room temperature for 3 hrs. After completion of the reaction, the reaction mixture was stirred together with water (50 ml) for 30 min. Extraction was made with ethyl acetate and water. The organic layer was isolated and concentrated in a vacuum. The concentrate was stirred together with acetic acid (200 ml) and HCl (1 ml) at 80° C. After the reaction was completed, the precipitate thus formed was filtered and washed with methanol to afford <Intermediate 11-a> (20.0 g, 73%).

Synthesis Example 11-(2)

Synthesis of Compound 73

Compound 73 was synthesized as illustrated in the following Reaction Scheme 88:

<Reaction Scheme 88>

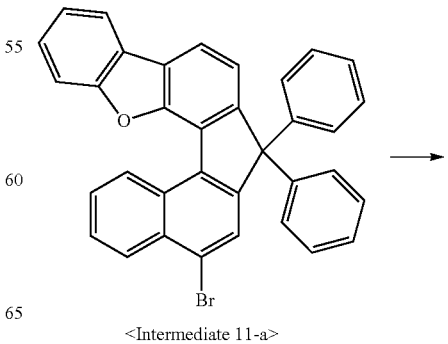

<Intermediate 11-a>

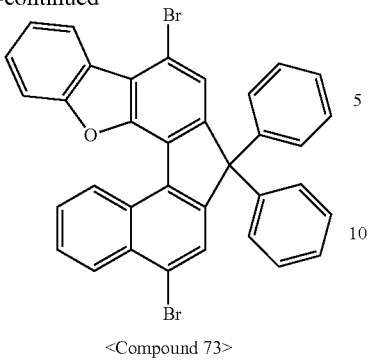

<Compound 73>

In a 1-L round-bottom flask reactor, a mixture of <Intermediate 11-a> (20.0 g, 0.037 mol) and chloroform (600 ml) was added with drops of a dilution of bromine (5.7 ml, 0.112 mol) in chloroform (40 ml) while stirring at room temperature for 12 hrs. After completion of the reaction, methanol (100 ml) was added to produce precipitates which were then washed with methanol. They were recrystallized in 1,2-dichlorobenzene and acetone to afford Compound 73 (14.0 g, 61.7%).

Synthesis Example 11-(3)

Synthesis of Intermediate 11-b

Intermediate 11-b was synthesized as illustrated in the following Reaction Scheme 89:

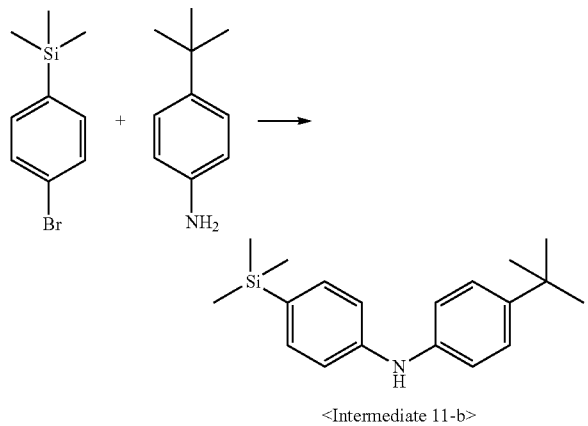

<Intermediate 11-b>

The same procedure as in Synthesis Example 4-(4), with the exception of using 1-bromo-4-(trimethylsilyl)benzene instead of 4-bromobiphenyl, was conducted to synthesize <Intermediate 11-b> (13.1 g, 72.1%).

Synthesis Example 11-(4)

Synthesis of Compound of Chemical Formula 11

The compound of Chemical Formula 11 was synthesized as illustrated in the following Reaction Scheme 90:

<Reaction Scheme 90>

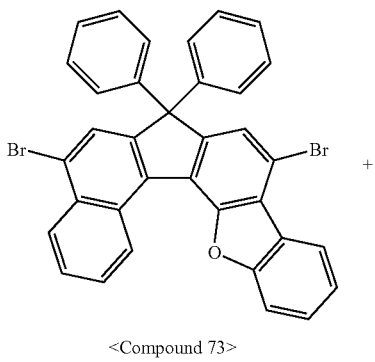

<Compound 73>

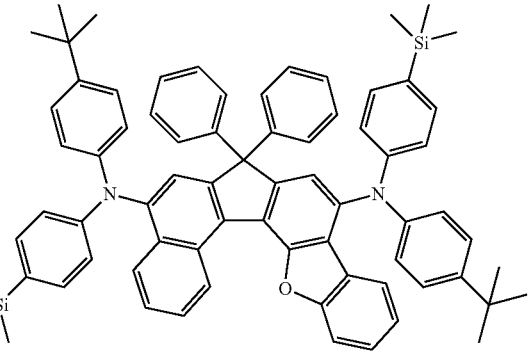

<Intermediate 11-b>

<Chemical Formula 11>

The same procedure as in Synthesis Example 1-(7), with the exception that Compound 73 and <Intermediate 11-b> were respectively used instead of Compound 1 and bis(4-tert-butylphenyl)amine, was conducted to synthesize the compound of Chemical Formula 11 (3.0 g, 35%).

MS (MALDI-TOF): m/z 1048.5 [M$^+$]

Synthesis Example 12

Synthesis of Compound 105

Synthesis Example 12-(1)

Synthesis of Intermediate 12-a

Intermediate 12-a was synthesized as illustrated in the following Reaction Scheme 91:

Reaction Scheme 91

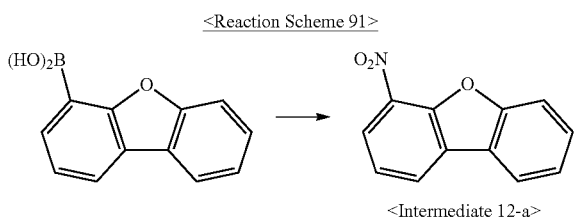 [SMILES: OB(O)c1cccc2c1oc1ccccc12 ; O=[N+]([O-])c1cccc2c1oc1ccccc12]

<Intermediate 12-a>

In a 2-L round-bottom flask reactor, 4-dibenzofuran boronic acid (85.0 g, 0.401 mol), bismuth (III) nitrate pentahydrate (99.2 g, 0.200 mol), and toluene (400 ml) were stirred together at 70° C. for 3 hrs under a nitrogen atmosphere. After completion of the reaction, the reaction mixture was cooled to room temperature, and the precipitates thus formed were filtered and washed with toluene to afford <Intermediate 12-a> (61.5 g, 72%).

Synthesis Example 12-(2)

Synthesis of Intermediate 12-b

Intermediate 12-b was synthesized as illustrated in the following Reaction Scheme 92:

Reaction Scheme 92

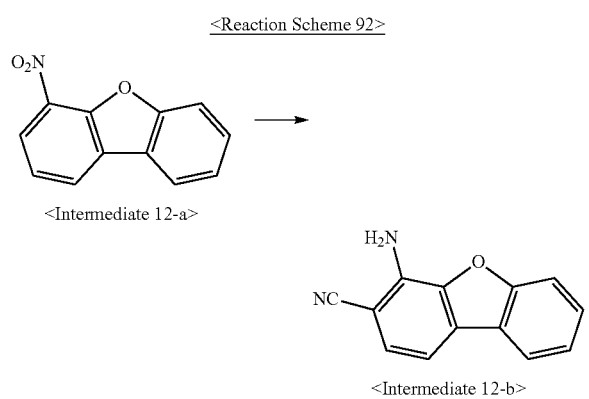

<Intermediate 12-a>

<Intermediate 12-b>

In a 2-L round-bottom flask reactor, ethylcyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. <Intermediate 12-a> (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded <Intermediate 12-b> (20.0 g, 16%).

Synthesis Example 12-(3)

Synthesis of Intermediate 12-c

Intermediate 12-c was synthesized as illustrated in the following Reaction Scheme 93:

Reaction Scheme 93

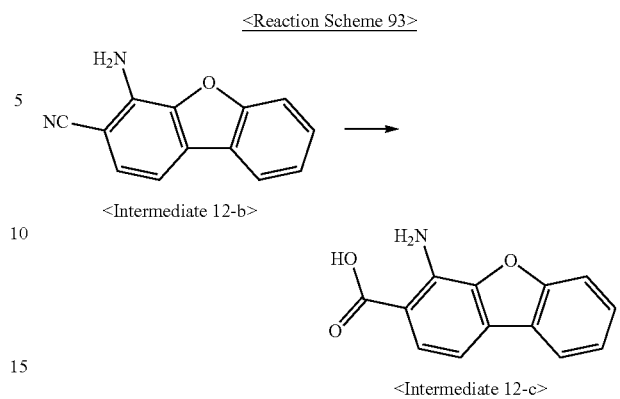

<Intermediate 12-b>

<Intermediate 12-c>

In a 2-L round-bottom flask reactor, <Intermediate 12-b> (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford <Intermediate 12-c> (17.0 g, 88.5%).

Synthesis Example 12-(4)

Synthesis of Intermediate 12-d

Intermediate 12-d was synthesized as illustrated in the following Reaction Scheme 94:

Reaction Scheme 94

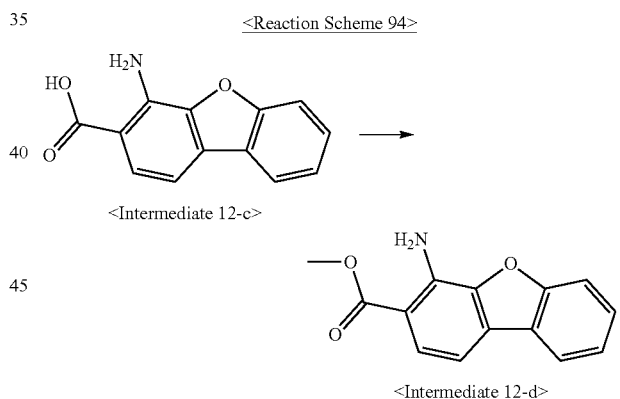

<Intermediate 12-c>

<Intermediate 12-d>

In a 2-L round-bottom flask reactor, <Intermediate 12-c> (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford <Intermediate 12-d> (14.0 77.6%).

Synthesis Example 12-(5)

Synthesis of Intermediate 12-e

Intermediate 12-e was synthesized illustrated in the following Reaction Scheme 95:

<Reaction Scheme 95>

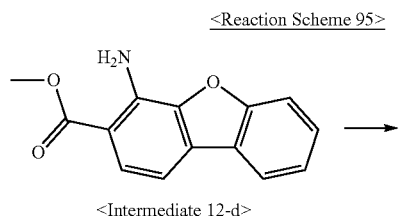

<Intermediate 12-d>

<Intermediate 12-e>

The same procedure as in Synthesis Example 5-(1), with the exception of using <Intermediate 12-d> instead of 2-phenoxyaniline, was conducted to synthesize <Intermediate 12-e> (9.1 g, 48%).

Synthesis Example 12-(6)

Synthesis of Intermediate 12-f

Intermediate 12-f was synthesized illustrated in the following Reaction Scheme 96:

<Reaction Scheme 96>

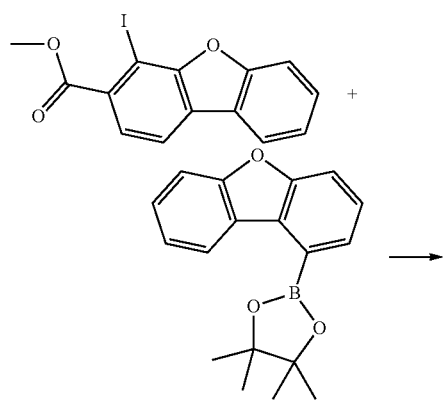

<Intermediate 12-e>  <Intermediate 8-a>  <Intermediate 12-f>

The same procedure as in Synthesis Example 8-(2), with the exception of using <Intermediate 12-e> instead of methyl 5-bromo-2-iodobenzoate, was conducted to synthesize <Intermediate 12-f> (5.3 g, 52.3%).

Synthesis Example 12-(7)

Synthesis of Intermediate 12-g

Intermediate 12-g was synthesized illustrated in the following Reaction Scheme 97:

<Reaction Scheme 97>

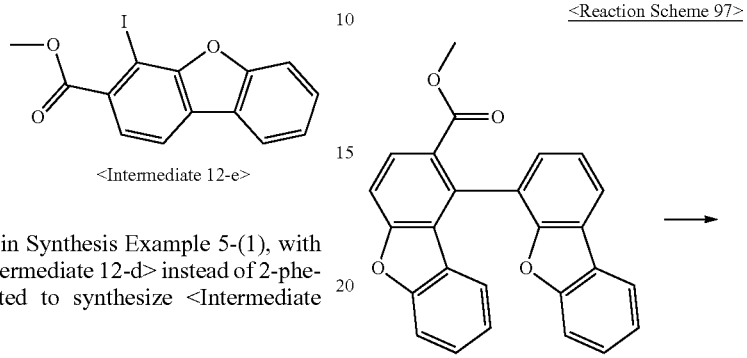

<Intermediate 12-f>

<Intermediate 12-g>

The same procedure as in Synthesis Example 1-(2), with the exception of using <Intermediate 12-f> instead of <Intermediate 1-a>, was conducted to synthesize <Intermediate 12-g> (4.5 g, 88.1%).

Synthesis Example 12-(8)

Synthesis of Intermediate 12-h

Intermediate 12-h was synthesized as illustrated in the following Reaction Scheme 98:

<Reaction Scheme 98>

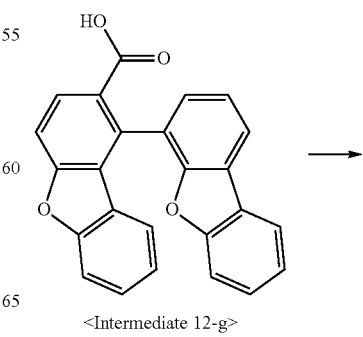

<Intermediate 12-g>

<Reaction Scheme 100>

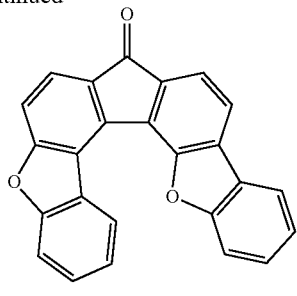

<Intermediate 12-h>

The same procedure as in Synthesis Example 1-(3), with the exception of using <Intermediate 12-g> instead of <Intermediate 1-b>, was conducted to synthesize <intermediate 12-h> (3.8 g, 88.8%).

Synthesis Example 12-(9)

Synthesis of Intermediate 12-i

Intermediate 12-i was synthesized as illustrated in the following Reaction Scheme 99:

<Reaction Scheme 99>

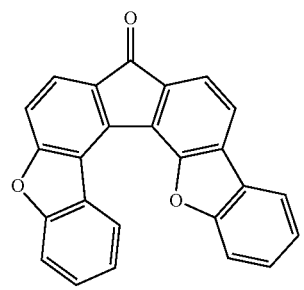

<Intermediate 12-h>

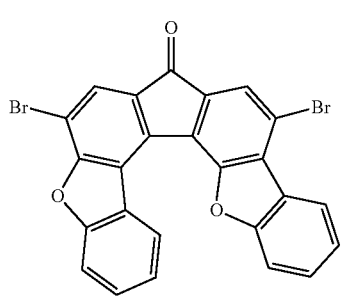

<Intermediate 12-i>

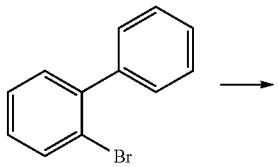

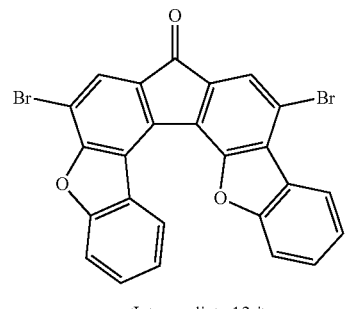

<Intermediate 12-i>

The same procedure as in Synthesis Example 1-(4), with the exception of using <Intermediate 12-h> instead of <Intermediate 1-c>, was conducted to synthesize <Intermediate 12-i> (3 g, 55%).

Synthesis Example 12-(10)

Synthesis of Intermediate 12-j

Intermediate 12-j was synthesized as illustrated in the following Reaction Scheme 100:

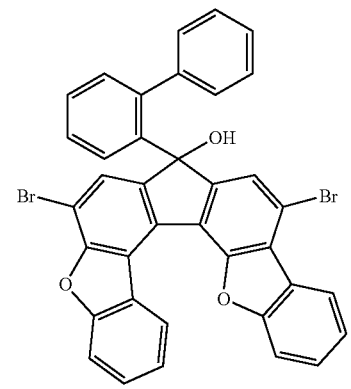

<Intermediate 12-j>

The same procedure as in Synthesis Example 1-(5), with the exception of using <Intermediate 12-i> instead of <Intermediate 1-d>, was conducted to synthesize <intermediate 12-j> (2.5 g, 64%).

Synthesis Example 12-(11)

Synthesis of Compound 105

Compound 105 was synthesized as illustrated in the following Reaction Scheme 101:

<Reacrtion Scheme 101>

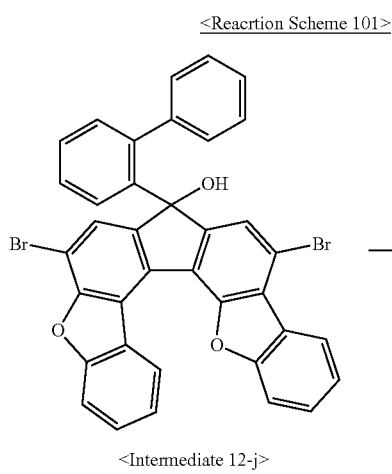

<Intermediate 12-j>

↓

<Compound 105>

The same procedure as in Synthesis Example 1-(6), with the exception of using <Intermediate 12-j> instead of <Intermediate 1-e>, was conducted to Compound 105 (2.2 g, 90.4%).

Synthesis Example 12-(12)

Synthesis of Intermediate 12-k

Intermediate 12-k was synthesized as illustrated in the following Reaction Scheme 102:

<Reaction Scheme 102>

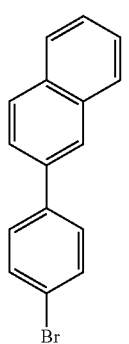

-continued

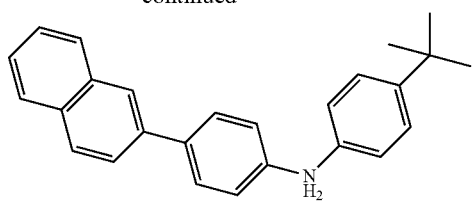

<Intermediate 12-k>

In a 250-ml round-bottom flask reactor, 1-bromo-4-(2-naphthyl)benzene (10.0 g, 0.035 mol), 4-tert-butyl aniline (5.8 g, 0.039 mol), tris(dibenzylidne acetone)dipalladium(0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together for 3 hrs under reflux. After completion of the reaction, the reaction mixture was cooled to room temperature and extracted with ethyl acetate and water. The organic layer was isolated, dried over magnesium sulfate, and concentrated in a vacuum. Purification through column chromatography gave <Intermediate 12-k> (10 g, 80%).

Synthesis Example 12-(13)

Synthesis of Compound of Chemical Formula 12

The compound of Chemical Formula 12 was synthesized as illustrated in the following Reaction Scheme 103:

<Reaction Scheme 103>

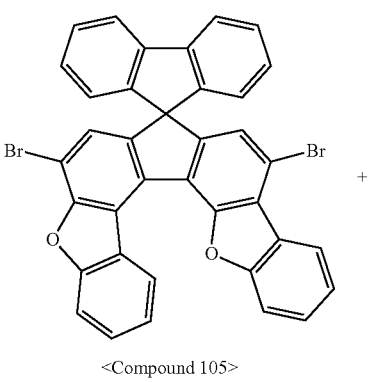

<Compound 105>

+

<Intermediate 12-k>

→

-continued

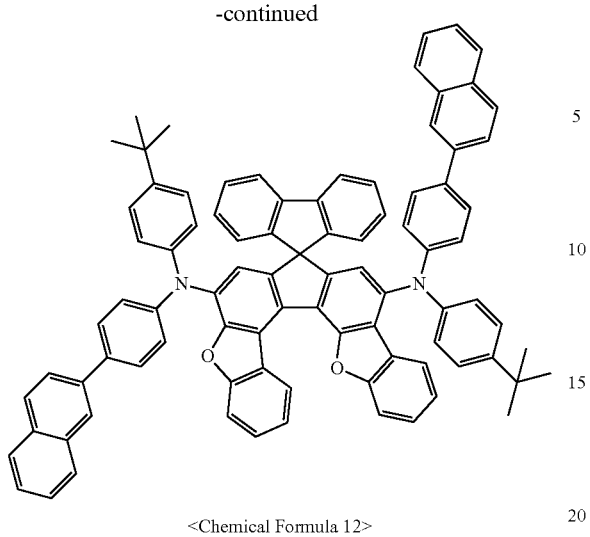

<Chemical Formula 12>

The same procedure as in Synthesis Example 1-(7), with the exception that Compound 105 and <Intermediate 12-k> were respectively used instead of Compound 1 and bis(4-tert-butylphenyl)amin, was conducted to synthesize the compound of Chemical Formula 12 (1.6 g, 38%).
MS (MALDI-TOF): m/z 1194.5 [M+]

Synthesis Example 13

Synthesis of Compound 14

Synthesis Example 13-(1)

Synthesis of Intermediate 13-a

Intermediate 13-a was synthesized as illustrated in the following Reaction Scheme 104:

<Reaction Scheme 104>

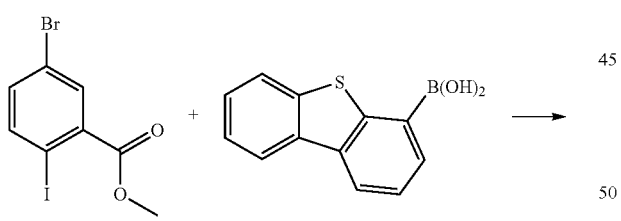

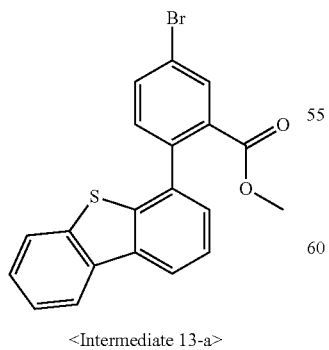

<Intermediate 13-a>

The same procedure as in Synthesis Example 1-(1), with the exception of using 4-dibenzothiophene boronic acid instead of 4-dibenzofuran boronic acid, was conducted to synthesize <Intermediate 13-a> (18.0 g, 61.8%).

Synthesis Example 13-(2)

Synthesis of Intermediate 13-b

Intermediate 13-b was synthesized as illustrated in the following Reaction Scheme 105:

<Reaction Scheme 105>

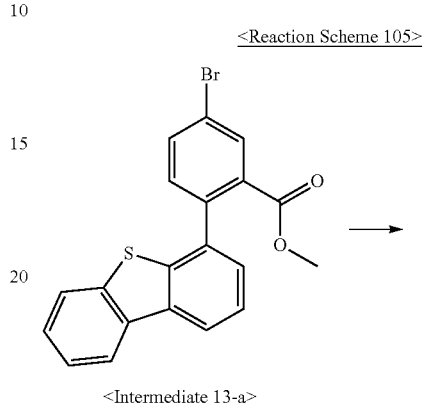

<Intermediate 13-a>

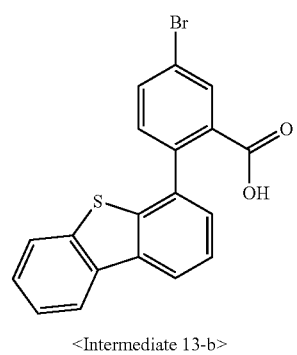

<Intermediate 13-b>

The same procedure as in Synthesis Example 1-(2), with the exception of using <Intermediate 13-a> instead of <Intermediate 1-a>, was conducted to synthesize <Intermediate 13-b> (15.0 g, 86.5%).

Synthesis Example 13-(3)

Synthesis of Intermediate 13-c

Intermediate 13-c was synthesized as illustrated in the following Reaction Scheme 106:

<Reaction Scheme 106>

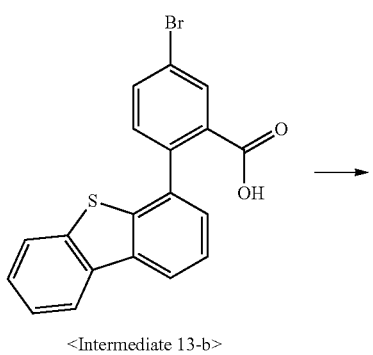

<Intermediate 13-b>

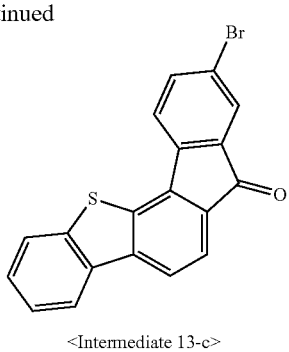

<Intermediate 13-c>

The same procedure as in Synthesis Example 1-(3), with the exception of using <Intermediate 13-b> instead of <Intermediate 1-b>, was conducted to synthesize <Intermediate 13-c> (12.0 g, 83.9%).

Synthesis Example 13-(4)

Synthesis of Intermediate 13-d

Intermediate 13-d was synthesized as illustrated in the following Reaction Scheme 107:

<Reaction Scheme 107>

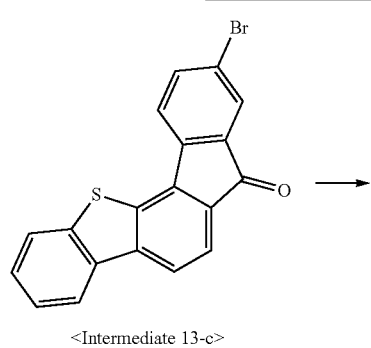

<Intermediate 13-c>

<Intermediate 13-d>

The same procedure as in Synthesis Example 1-(4), with the exception of using <Intermediate 13-c> instead of <Intermediate 1-c>, was conducted to synthesize <Intermediate 13-d> (11.0 g, 75.4%).

Synthesis Example 13-(5)

Synthesis of Intermediate 13-e

Intermediate 13-e was synthesized as illustrated in the following Reaction Scheme 108:

<Reaction Scheme 108>

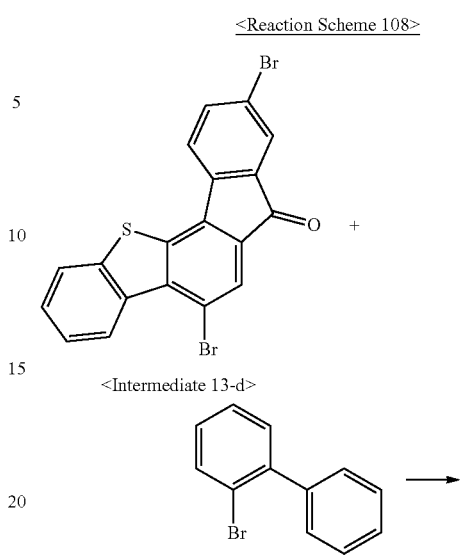

<Intermediate 13-d>

<Intermediate 13-e>

The same procedure as in Synthesis Example 1-(5), with the exception of using <Intermediate 13-d> instead of <Intermediate 1-d>, was conducted to synthesize <Intermediate 13-e> (11.2 g, 75.6%).

Synthesis Example 13-(6)

Synthesis of Compound 14

Compound 14 was synthesized as illustrated in the following Reaction Scheme 109:

<Reaction Scheme 109>

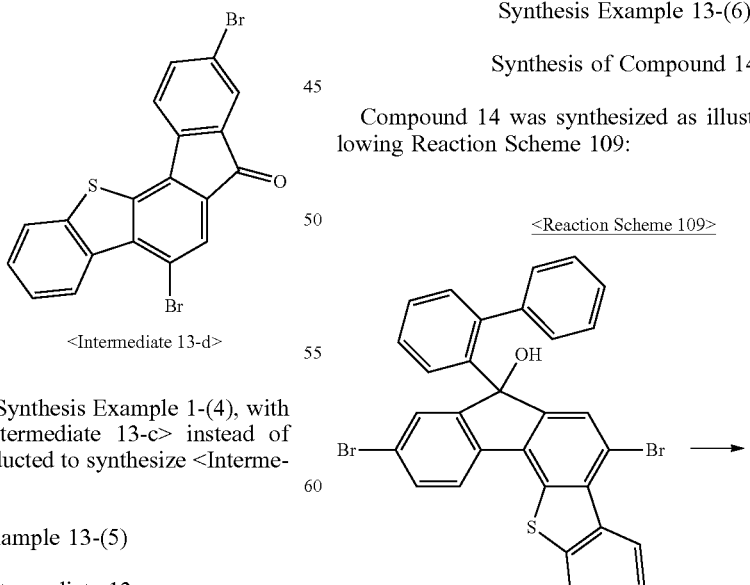

<Intermediate 13-e>

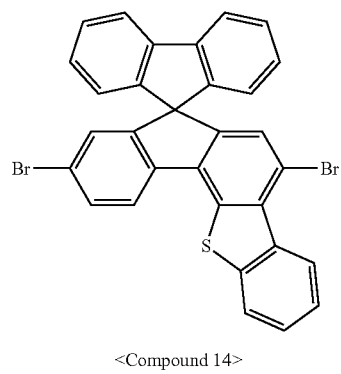

<Compound 14>

The same procedure as in Synthesis Example 1-(6), with the exception of using <Intermediate 13-e> instead of <Intermediate 1-e>, was conducted to synthesize Compound 14 (8.7 g, 80.1%).

Synthesis Example 13-(7)

Synthesis of Compound of Chemical Formula 13

The compound of Chemical Formula 13 was synthesized as illustrated in the following Reaction Scheme 110:

<Reaction Scheme 110>

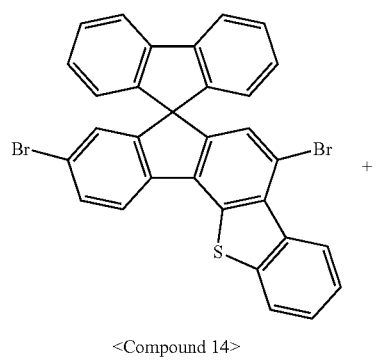

<Compound 14>

+

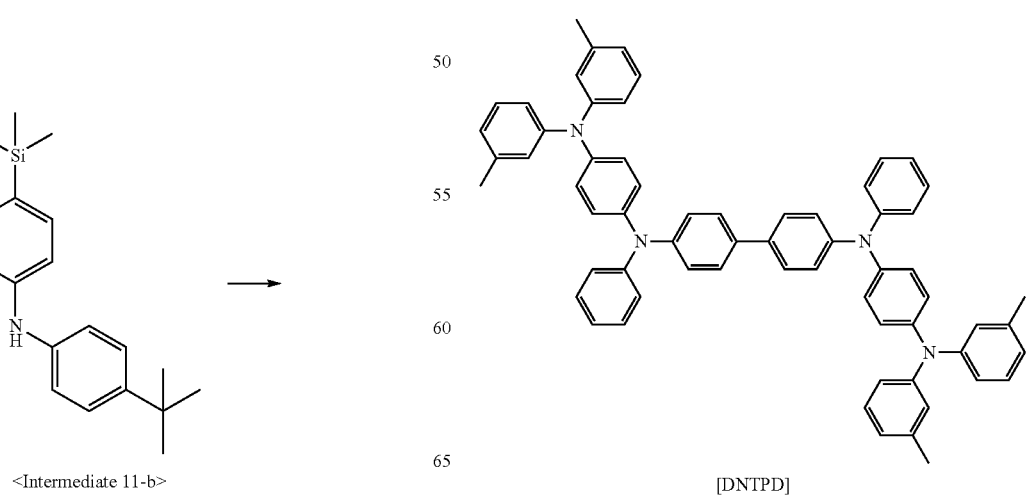

<Intermediate 11-b>

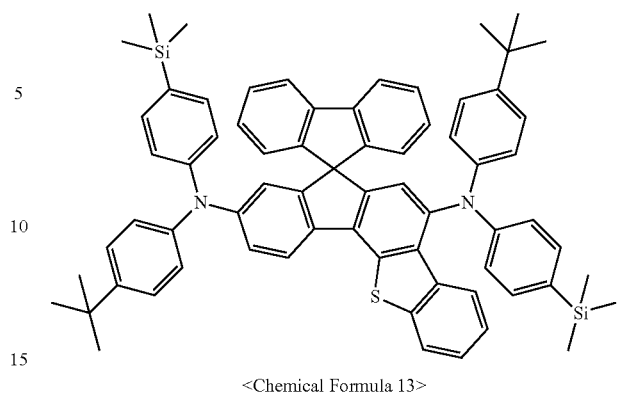

<Chemical Formula 13>

The same procedure as in Synthesis Example 1-(7), with the exception of using <Intermediate 11-b> instead of bis(4-tert-butylphenyl)amine, was conducted to synthesize the compound of Chemical Formula 13 (3.2 g, 36.6%).

Examples 1 to 8

Fabrication of Organic Light-Emitting Diode

An ITO glass substrate was patterned to have a translucent area of 2 mm×2 mm and then cleaned. The ITO glass was mounted in a vacuum chamber that was then set to have a base pressure of $1\times10^{-7}$ torr. On the ITO glass substrate, films were formed of DNTPD (700 Å) and α-NPD (300 Å) in that order. A light-emitting layer (250 Å) was formed of a mixture including [BH1] and 3% of each of the compounds shown in Table 1 according to the present disclosure. Then, [Chemical Formula E-1] and [Chemical Formula E-2] were deposited at a ratio of 1:1 to form an electron transport layer 300 Å thick, on which an electron injection layer of [Chemical Formula E-1] (5 Å thick) was formed and then covered with an Al layer (1000 Å) to fabricate an organic light-emitting diode. The organic light-emitting diodes thus obtained were measured at 0.4 mA for luminescence properties.

[DNTPD]

-continued

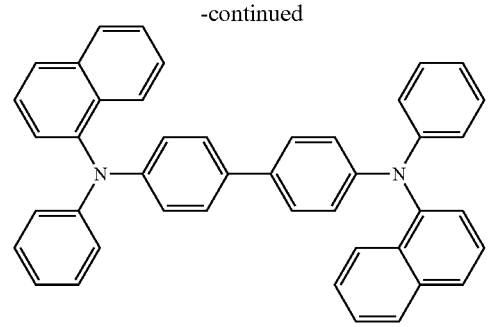

[α-NPD]

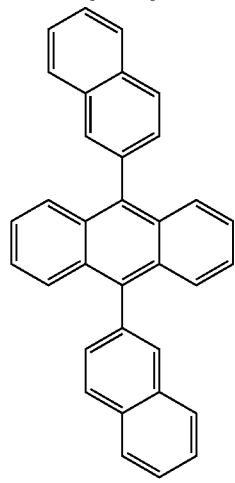

[BH1]

[Chemical FormulaE-1]

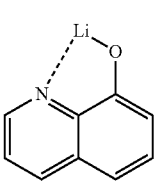

[Chemical FormulaE-2]

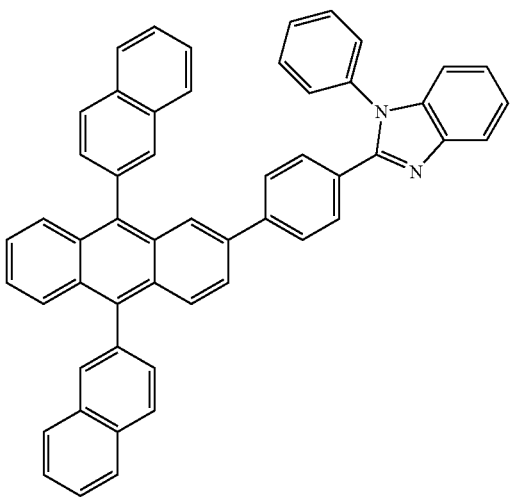

Comparative Examples 1 and 2

Organic light-emitting diodes were fabricated in the same manner as in Examples 1 to 11, with the exception that [BD1] and [BD2] were used, instead of the compounds used in Examples 1 to 11. The luminescence of the organic light-emitting diodes was measured at 0.4 mA. The structures of [BD1] and [BD2] are as follows,

[BD1]

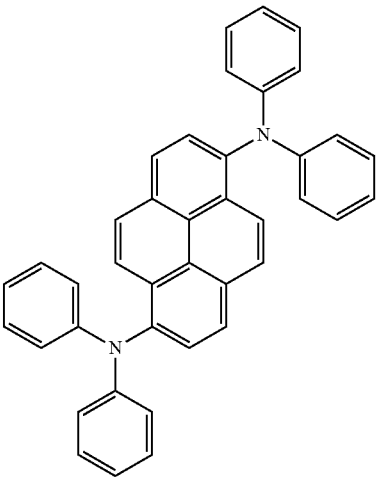

[BD2]

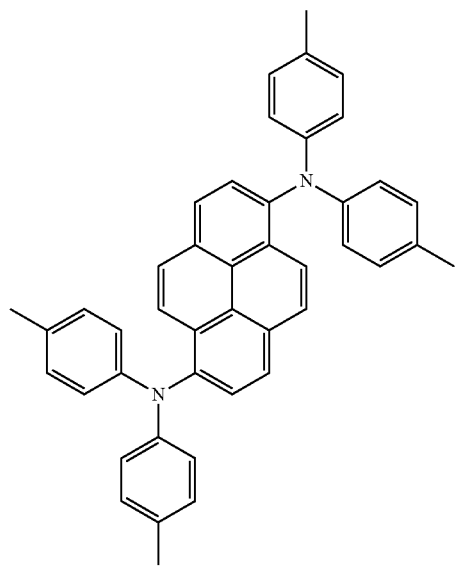

The organic light-emitting diodes fabricated in Examples 1 to 11 and Comparative Examples 1 and 2 were measured for voltage, current, luminance, color coordinates, and lifetime, and the results are summarized in Table 1, below. In Table 1, T97 refers to the time taken for the initial luminance to decrease by 3%.

TABLE 1

| Ex. No. | Volt | Current Density (mA/cm$^2$) | Luminance (cd/m$^2$) | CIEx | CIEy | T97 |
|---|---|---|---|---|---|---|
| C. Ex. 1 [BD1] | 4.1 | 10 | 515 | 0.143 | 0.150 | 42 |
| C. Ex. 2 [BD2] | 4.0 | 10 | 550 | 0.141 | 0.154 | 40 |
| Ex. 1 [Chemical Formula 1] | 3.8 | 10 | 750 | 0.130 | 0.133 | 98 |

TABLE 1-continued

| Ex. No. | Volt | Current Density (mA/cm$^2$) | Luminance (cd/m$^2$) | CIEx | CIEy | T97 |
|---|---|---|---|---|---|---|
| Ex. 2 [Chemical Formula 4] | 3.8 | 10 | 650 | 0.133 | 0.115 | 113 |
| Ex. 3 [Chemical Formula 5] | 3.8 | 10 | 801 | 0.138 | 0.110 | 120 |
| Ex. 4 [Chemical Formula 7] | 3.8 | 10 | 980 | 0.132 | 0.181 | 110 |
| Ex. 5 [Chemical Formula 8] | 3.8 | 10 | 679 | 0.141 | 0.116 | 121 |
| Ex. 6 [Chemical Formula 10] | 3.8 | 10 | 880 | 0.136 | 0.133 | 110 |
| Ex. 7 [Chemical Formula 11] | 3.8 | 10 | 850 | 0.130 | 0.164 | 118 |
| Ex. 8 [Chemical Formula 12] | 3.8 | 10 | 816 | 0.134 | 0.121 | 120 |

As is understood from the data of Table 1, the amine compounds of the present disclosure exhibited far higher luminance and light emission efficiency and a longer lifetime than the compounds of Comparative Examples 1 to 4, thereby demonstrating their high applicability to organic electroluminescence devices.

INDUSTRIAL APPLICABILITY

As described hitherto, the compound represented by Chemical Formula A or B is useful as an intermediate of an organic luminescent material, which exhibits excellent diode properties, including luminance, light emission efficiency and longevity, compared to conventional materials, thus being available for use in organic light-emitting diodes having improved properties.

The invention claimed is:

1. A compound represented by the following [Chemical Formula B]:

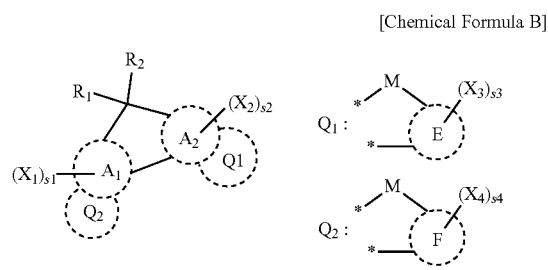

[Chemical Formula B]

wherein, $A_1$, $A_2$, E, and F are the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

M is any one selected from among $CR_4R_5$, O, and S;

$R_1$, $R_2$, $R_4$, and $R_5$ are same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms, a cyano, a nitro, and a halogen, with a proviso that $R_1$ and $R_2$ together may form a mono- or polycyclic aliphatic or aromatic ring in Chemical Formula B;

s1, s3 and s4 are each independently 0 or 1, and s2 is 1, wherein only one of s1, s3 and s4 is 1 and the others are 0; and $X_1$ to $X_4$ are same or different, and are each independently a leaving group selected from the group consisting of an alkyl sulfonate of 1 to 30 carbon atoms, an aryl sulfonate of 6 to 40 carbon atoms, an arylalkyl sulfonate of 7 to 40 carbon atoms, a halogenated alkyl sulfonate of 1 to 30 carbon atoms, and a halogen atom selected from the group consisting of Cl, Br, F, and I; and two adjacent carbon atoms of an $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring, wherein the term 'substituted' in the expression 'substituted or unsubstituted' means having at least one substituent selected from the group consisting of a deuterium, a cyano, a halogen, an alkyl of 1 to 24 carbon atoms, a halogenated alkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkylsilyl of 1 to 24 carbon atoms, and an arylsilyl of 6 to 24 carbon atoms.

2. The compound of claim 1, wherein $A_1$, $A_2$, E, and F, which are same or different, are each independently a substituted or unsubstituted aromatic hydrocarbon ring of 6 to 50 carbon atoms.

3. The compound of claim 2, wherein the aromatic hydrocarbon ring is selected from among [Structural Formula 10] to [Structural Formula 21]:

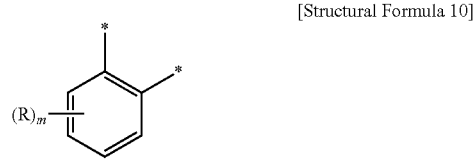

[Structural Formula 10]

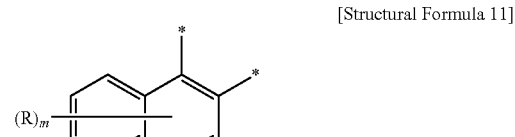

[Structural Formula 11]

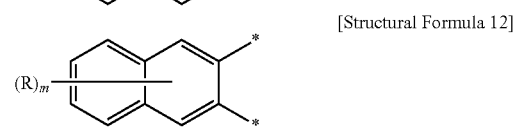

[Structural Formula 12]

[Structural Formula 13]

[Structural Formula 14]

[Structural Formula 15]

[Structural Formula 16]

[Structural Formula 17]

[Structural Formula 18]

[Structural Formula 19]

[Structural Formula 20]

[Structural Formula 21]

wherein,

"-*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are same or different, and are each independently any one selected from among a deuterium, a cyano, a halogen, a nitro, an alkyl of 1 to 24 carbon atoms, a halogenated alkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkylsilyl of 1 to 24 carbon atoms, and an arylsilyl of 6 to 24 carbon atoms; and m is an integer of 1 to 8, with a proviso that when m is 2 or greater or two or more R's exist, corresponding R's are same or different.

4. The compound of claim 1, wherein $X_1$ to $X_4$ of Chemical Formula B are same or different and are each independently selected from the group consisting of Cl, Br, F, and I.

5. The compound of claim 1, wherein the substituents $R_1$ and $R_2$ of Chemical Formula B are same or different, and are each independently a substituted or unsubstituted aryl of 6 to 24 carbon atoms and are connected to each other to form a ring.

6. The compound of claim 1, wherein the substituents $R_1$ and $R_2$ are same or different, and are each independently a substituted or unsubstituted aryl of 6 to 24 carbon atoms and are not connected to each other to thus not form a ring.

7. The compound of claim 1, wherein $R_1$, $R_2$, $R_4$, and $R_5$ are same or different and are each independently any one selected from among hydrogen, deuterium, a substituted or unsubstituted aryl of 6 to 20 carbon atoms, a substituted or unsubstituted cycloalkyl of 3 to 30 carbon atoms, a substituted or unsubstituted heteroaryl of 2 to 20 carbon atoms containing at least one heteroatom selected from among O, N, S, and Si, a cyano, and a halogen.

8. The compound of claim 1, wherein a substituent on each of the substituted $A_1$, $A_2$, E, F, and $R_1$, $R_2$, $R_4$, and $R_5$ is any one selected from the group consisting of a cyano, a halogen, an alkyl of 1 to 6 carbon atoms, an aryl of 6 to 18 carbon atoms, an arylalkyl of 6 to 18 carbon atoms, a heteroaryl of 3 to 18 carbon atoms, an alkylsilyl of 1 to 12 carbon atoms, an arylsilyl of 6 to 18 carbon atoms, and a halogenated alkyl of 1 to 6 carbon atoms.

9. The compound of claim 1, wherein the compound is selected from among [Compounds 21], [Compounds 23],

[Compounds 34] to [Compounds 37], [Compounds 40], [Compound 42], [Compounds 43], [Compounds 45] to [Compounds 46], [Compounds 48], [Compound 68], [Compound 69], [Compound 77] to [Compounds 79], [Compounds 82], [Compound 85], and [Compound 103] to [Compound 108]:
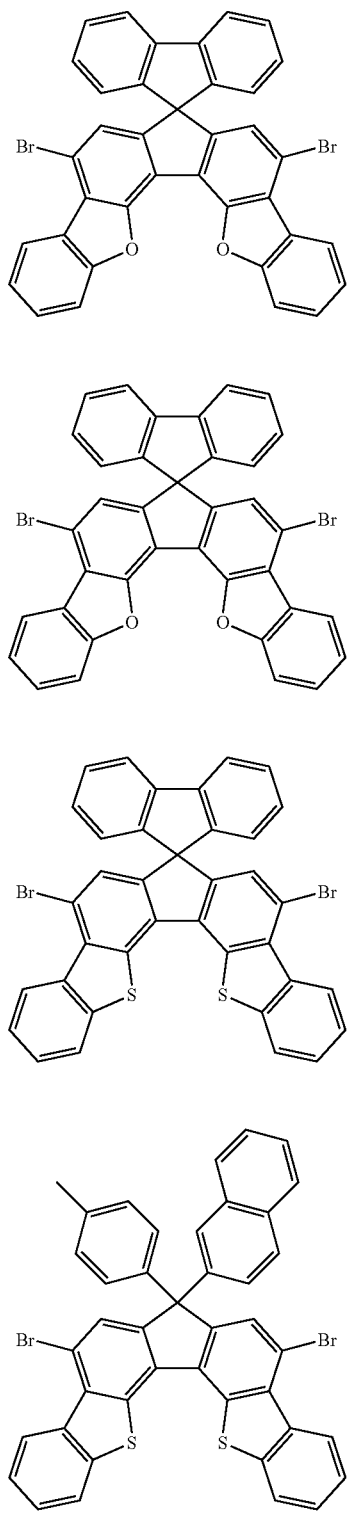
[Compound 21]
[Compound 23]
[Compound 34]
[Compound 35]
-continued
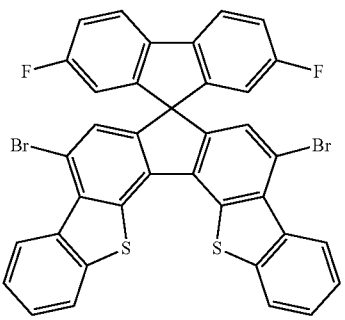
[Compound 36]
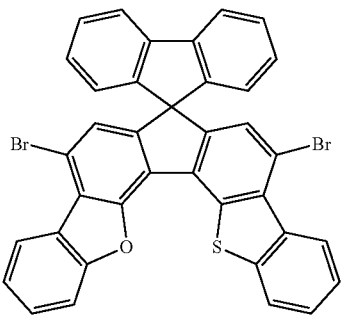
[Compound 37]
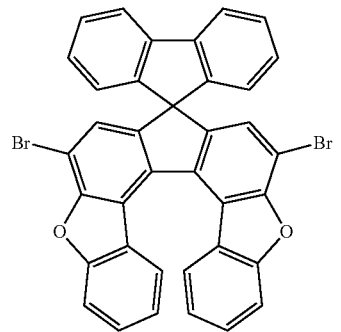
[Compound 40]
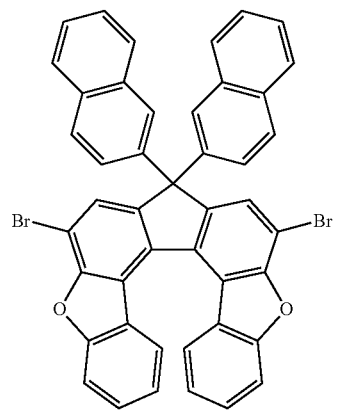
[Compound 42]

[Compound 43]
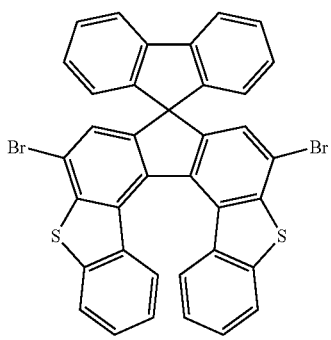
[Compound 68]
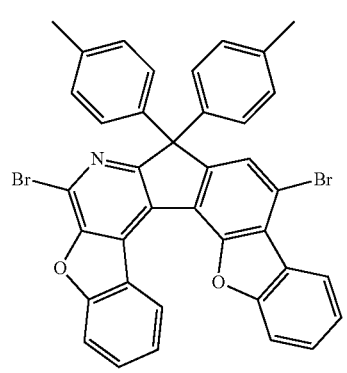
[Compound 45]
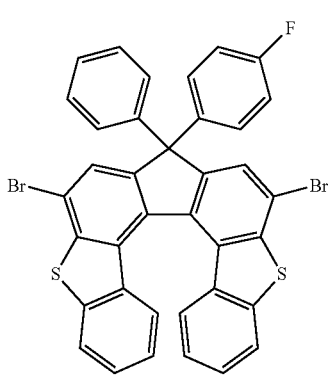
[Compound 69]
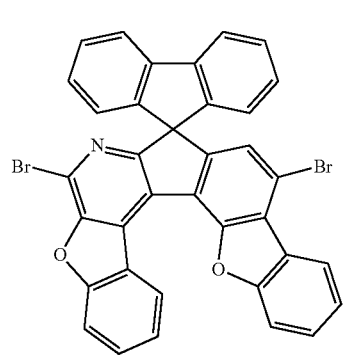
[Compound 46]
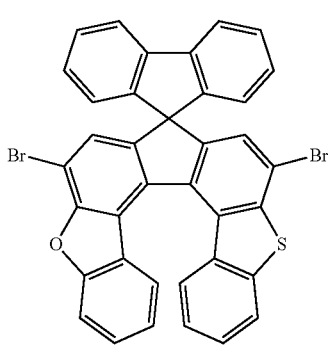
[Compound 77]
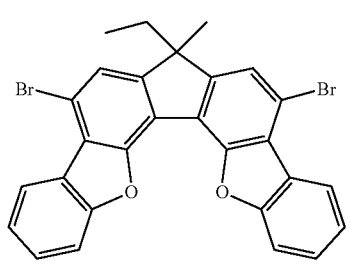
[Compound 78]
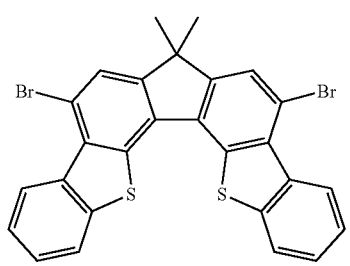
[Compound 48]
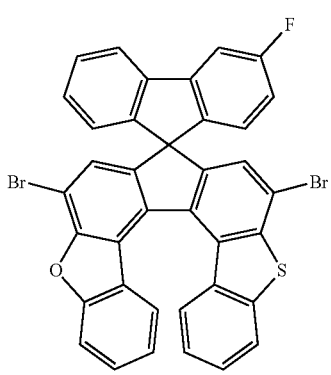
[Compound 79]
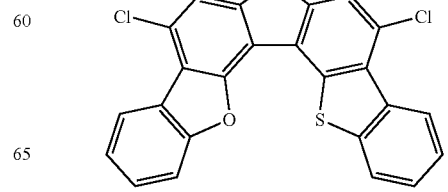

-continued

[Compound 82]
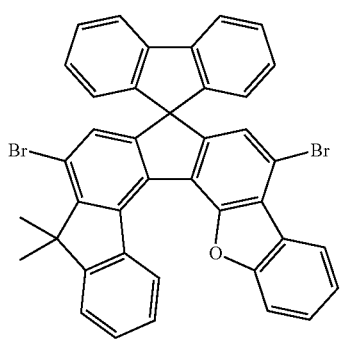

[Compound 85]
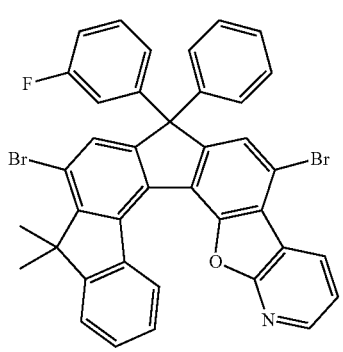

[Compound 103]
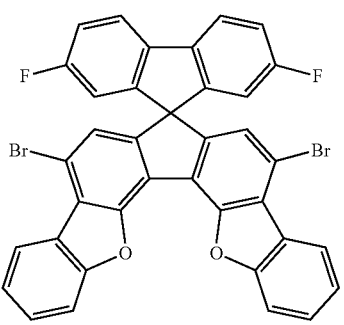

[Compound 104]
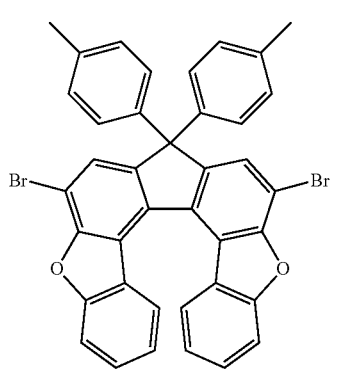

-continued

[Compound 105]
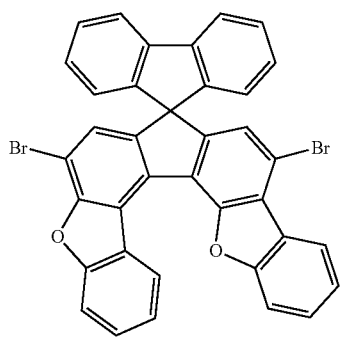

[Compound 106]
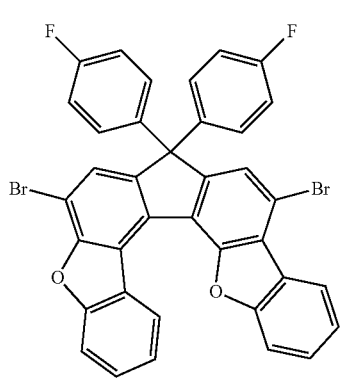

[Compound 107]
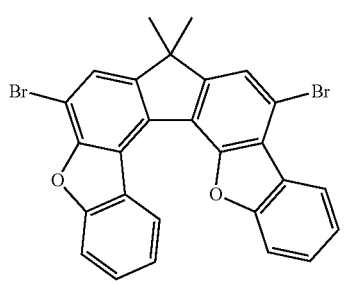

[Compound 108]
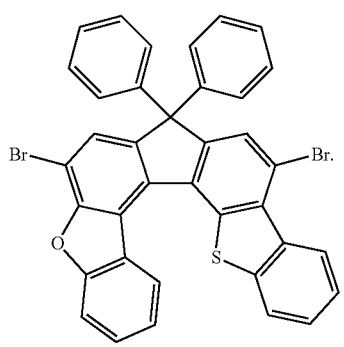

10. A method for preparing an amine derivative, comprising reacting the compound of claim 1 with a primary or secondary amine to afford an amine derivative in which at least one leaving group in the compound represented by Chemical Formula B is substituted by an amine radical resulting from depriving one hydrogen of the primary or secondary amine.

* * * * *